(12) United States Patent
Reilly et al.

(10) Patent No.: US 10,112,999 B2
(45) Date of Patent: Oct. 30, 2018

(54) ANTI-PRLR ANTIBODY-DRUG CONJUGATES (ADC) AND USES THEREOF

(71) Applicant: AbbVie Inc., North Chicago, IL (US)

(72) Inventors: Edward B. Reilly, Libertyville, IL (US); Mark Anderson, Grayslake, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 15/946,774

(22) Filed: Apr. 6, 2018

(65) Prior Publication Data

US 2018/0244789 A1    Aug. 30, 2018

Related U.S. Application Data

(60) Provisional application No. 62/482,640, filed on Apr. 6, 2017.

(51) Int. Cl.
*A61K 47/68* (2017.01)
*A61P 35/00* (2006.01)
*C07K 16/28* (2006.01)

(52) U.S. Cl.
CPC ...... *C07K 16/2866* (2013.01); *A61K 47/6803* (2017.08); *A61K 47/6849* (2017.08); *A61K 47/6889* (2017.08); *A61P 35/00* (2018.01); *C07K 2317/24* (2013.01); *C07K 2317/51* (2013.01); *C07K 2317/515* (2013.01); *C07K 2317/52* (2013.01)

(58) Field of Classification Search
None
See application file for complete search history.

(56) References Cited

U.S. PATENT DOCUMENTS

| | | | |
|---|---|---|---|
| 6,867,187 B2 | 3/2005 | Clevenger et al. |
| 7,422,899 B2 | 9/2008 | Elenbaas et al. |
| 7,507,716 B2 | 3/2009 | Diogenes et al. |
| 7,521,541 B2 | 4/2009 | Eigenbrot et al. |
| 7,741,319 B2 | 6/2010 | Howard et al. |
| 7,855,275 B2 | 12/2010 | Eigenbrot et al. |
| 7,867,493 B2 | 1/2011 | Damiano et al. |
| 7,989,434 B2 | 8/2011 | Feng |
| 8,455,622 B2 | 6/2013 | McDonagh et al. |
| 8,648,046 B2 | 2/2014 | Chen |
| 8,754,035 B2 | 6/2014 | Chen |
| 8,883,979 B2 | 11/2014 | Ma et al. |
| 9,005,614 B2 | 4/2015 | Damiano et al. |
| 9,023,357 B2 | 5/2015 | Ma et al. |
| 9,302,015 B2 | 4/2016 | Papadopoulos et al. |
| 9,545,451 B2 | 1/2017 | Papadopoulos et al. |
| 9,649,374 B2 | 5/2017 | Otto et al. |
| 9,688,764 B2 | 6/2017 | Papadopoulos et al. |
| 9,951,141 B2 | 4/2018 | Nittoli et al. |
| 2005/0123536 A1 | 6/2005 | Law et al. |
| 2005/0180972 A1 | 8/2005 | Wahl et al. |
| 2007/0269438 A1 | 11/2007 | Elenbaas et al. |
| 2007/0280931 A1 | 12/2007 | Chen et al. |
| 2011/0150760 A1 | 6/2011 | Damiano et al. |
| 2011/0280891 A1* | 11/2011 | Liu ............... C07K 16/2875 424/181.1 |
| 2012/0315276 A1 | 12/2012 | Otto et al. |
| 2012/0321632 A1 | 12/2012 | Otto et al. |
| 2013/0022606 A1 | 1/2013 | Otto et al. |
| 2013/0028917 A1 | 1/2013 | Howard et al. |
| 2013/0028919 A1 | 1/2013 | Howard et al. |
| 2013/0129739 A1 | 5/2013 | Ottto et al. |
| 2013/0171147 A1 | 7/2013 | Otto et al. |
| 2013/0272968 A1 | 10/2013 | Otto et al. |
| 2014/0227294 A1 | 8/2014 | Anderson et al. |
| 2016/0030591 A1 | 2/2016 | Nittoli |
| 2016/0130358 A1* | 5/2016 | Bhakta .............. C07K 16/18 530/387.3 |
| 2017/0022281 A1 | 1/2017 | Anderson et al. |
| 2018/0094066 A1 | 4/2018 | Papadopoulos et al. |

FOREIGN PATENT DOCUMENTS

| | | |
|---|---|---|
| CN | 102741291 A | 10/2012 |
| EP | 2530089 A1 | 12/2012 |
| EP | 3148592 A2 | 4/2017 |
| JP | 2010501163 A | 1/2010 |
| WO | WO-8912624 A2 | 12/1989 |
| WO | WO-2005123780 A2 | 12/2005 |
| WO | WO-2006111759 A1 | 10/2006 |
| WO | WO-2008022295 A2 | 2/2008 |
| WO | WO-2011069795 A1 | 6/2011 |
| WO | WO-2011069796 A1 | 6/2011 |
| WO | WO-2011069797 A1 | 6/2011 |
| WO | WO-2011069798 A1 | 6/2011 |
| WO | WO-2011130598 A1 | 10/2011 |
| WO | WO-2011151405 A1 | 12/2011 |
| WO | WO-2012136519 A1 | 10/2012 |
| WO | WO-2012163932 A1 | 12/2012 |
| WO | 2014/105810 * | 7/2014 |
| WO | WO-2014105810 A1 | 7/2014 |

(Continued)

OTHER PUBLICATIONS

Jeffrey et al (Bioconjugate Chemistry, 24:1256-1263, 2013).*
Arden., et al., "The Genes Encoding the Receptors for Prolactin and Growth Hormone Map to Human Chromosome 5," The American Journal of Human Genetics—Cell, 1989, vol. 45, p. A129.
Arden K.C., et al., "The Receptors for Prolactin and Growth Hormone are Localized in the Same Region of Human Chromosome 5," Cytogenetics and cell genetics, 1990, vol. 53 (2-3), pp. 161-165.
Arnon R., et al., "Monoclonal Antibodies for Immunotargeting of Drugs in Cancer Therapy," in: Monoclonal Antibodies and Cancer Therapy, Reisfeld., et al., Eds., Alan R. Liss, Inc., 1985, pp. 243-256.

(Continued)

*Primary Examiner* — Patricia Duffy
(74) *Attorney, Agent, or Firm* — Michael S. Montgomery

(57) ABSTRACT

Provided are antibody drug conjugates that bind PRLR, in particular human PRLR, their methods of making, and uses thereof.

11 Claims, 14 Drawing Sheets

Specification includes a Sequence Listing.

(56) References Cited

FOREIGN PATENT DOCUMENTS

| WO | WO-2015026907 A1 | 2/2015 |
|---|---|---|
| WO | WO-2015187596 A2 | 12/2015 |
| WO | WO-2016201065 A1 | 12/2016 |
| WO | WO-2018102304 A1 | 6/2018 |

OTHER PUBLICATIONS

Axup J.Y., et al., "Synthesis of Site-Specific Antibody-Drug Conjugates Using Unnatural Amino Acids," Proceedings of the National Academy of Sciences of the United States of America, 2012, vol. 109 (40), pp. 16101-16106.
Baldwin., et al., Eds., "Analysis, Results, and Future Prospective of the Therapeutic Use of Radiolabeled Antibody in Cancer Therapy," in: Monoclonal Antibodies for Cancer Detection and Therapy, Academic Press, 1985.
Bauernhofer T., et al., "Prolactin Receptor is a Negative Prognostic Factor in Patients with Squamous Cell Carcinoma of the Head and Neck," British Journal of Cancer, 2011, vol. 104 (10), pp. 1641-1648.
Boutin J.M., et al., "Identification of a CDNA Encoding a Long Form of Prolactin Receptor in Human Hepatoma and Breast Cancer Cells," Molecular endocrinology (Baltimore, Md.), 1989, vol. 3 (9), pp. 1455-1461.
Canfield S.M., et al., "The Binding Affinity of Human IgG for its High Affinity Fc Receptor is Determined by Multiple Amino Acids in the CH2 Domain and is Modulated by the Hinge Region," The Journal of Experimental Medicine, 1991, vol. 173 (6), pp. 1483-1491.
Damiano J.S., et al., "Molecular Pathways: Blockade of the PRLR Signaling Pathway as a Novel Antihormonal Approach for the Treatment of Breast and Prostate Cancer," Clinical Cancer Research, Apr. 2013, vol. 19 (7), pp. 1644-1650.
Damiano J.S., et al., "Neutralization of Prolactin Receptor Function by Monoclonal Antibody Lfa102 a Novel Potential Therapeutic for the Treatment of Breast Cancer," Molecular Cancer Therapeutics, 2013, vol. 12 (3), pp. 295-305.
Doronina S.O., et al., "Novel Peptide Linkers for Highly Potent Antibody-auristatin Conjugate," Bioconjugate Chemistry, Oct. 2008, vol. 19 (10), pp. 1960-1963.
Dubowchik G.M., et al., "Cathepsin B-Sensitive Dipeptide Prodrugs. 1. a Model Study of Structural Requirements for Efficient Release of Doxorubicin," Bioorganic & Medicinal Chemistry Letters, 1998, vol. 8 (23), pp. 3341-3346.
Extended European Search Report EP18152359.8 dated May 24, 2018.
Francisco J.A., et al., "Cac10-Vcmmae, an Anti-Cd30-Monomethyl Auristatin E Conjugate with Potent and Selective Antitumor Activity," Blood, 2003, vol. 102 (4), pp. 1458-1465.
Galsgaard E.D., et al., "Re-evaluation of the Prolactin Receptor Expression in Human Breast Cancer," Journal of Endocrinology, 2009, vol. 201(1), pp. 115-128.
Gill S., et al., "Expression of Prolactin Receptors in Normal, Benign, and Malignant Breast Tissue: an Immunohistological Study," Journal of clinical pathology, 2001, vol. 54 (12), pp. 956-960.
Harbaum L., et al., "Clinicopathological Significance of Prolactin Receptor Expression in Colorectal Carcinoma and Corresponding Metastases," Modern Pathology : An Official Journal of The United States and Canadian Academy of Pathology, Inc, 2010, vol. 23 (7), pp. 961-971.
Hellstrom., et al., "Antibodies for Drug Delivery," in: Controlled Drug Delivery, Robinson., et al., Eds., 2nd Edition., 1987, Marcel Dekker, Inc.
International Search Report and Written Opinion for Application No. PCT/US2018/026381, dated Jul. 4, 2018, 13 pages.
Jeffrey S.C., et al., "Development and Properties of Beta-Glucuronide Linkers for Monoclonal Antibody-Drug Conjugates," Bioconjugate Chemistry, 2006, vol. 17 (3), pp. 831-840.

Jeffrey S.C., et al., "Minor Groove Binder Antibody Conjugates Employing a Water Soluble Beta-Glucuronide Linker," Bioorganic & Medicinal Chemistry Letters, 2007, vol. 17 (8), pp. 2278-2280.
Jiang X., et al., "Synthesis and Complete Stereochemical Assignment of Psymberin/Irciniastatin A," Journal of the American Chemical Society, 2005, vol. 127 (32), pp. 11254-11255.
Jung S., et al., "Improving in Vivo Folding and Stability of a Single-Chain Fv Antibody Fragment by Loop Grafting," Protein Engineering, 1997, vol. 10 (8), pp. 959-966.
Kabat E.A., et al., in: Sequence of Proteins of Immunological Interest, 4th Edition, 1987, Table of Contents.
Leav I., et al., "Prolactin Receptor Expression in the Developing Human Prostate and in Hyperplastic, Dysplastic, and Neoplastic Lesions," The American Journal of Pathology, 1999, vol. 154 (3), pp. 863-870.
Levina V.V., et al., "Biological Significance of Prolactin in Gynecologic Cancers," Cancer Research, 2009, vol. 69 (12), pp. 5226-5233.
Li H., et al., "Activation of Signal Transducer and Activator of Transcription 5 in Human Prostate Cancer is Associated with High Histological Grade," Cancer research, 2004, vol. 64 (14), pp. 4774-4782.
Ling C., et al., "Identification of Functional Prolactin (PRL) Receptor Gene Expression: PRL Inhibits Lipoprotein Lipase Activity in Human White Adipose Tissue," The Journal of Clinical Endocrinology & Metabolism, Apr. 2003, vol. 88 (4), pp. 1804-1808.
Lund J., et al., "Human Fc Gamma RI and Fc Gamma RII Interact with Distinct but Overlapping Sites on Human IgG," Journal of Immunology, 1991, vol. 147 (8), pp. 2657-2662.
Martei Y.M., et al., "Identifying Patients at High Risk of Breast Cancer Recurrence: Strategies to Improve Patient Outcomes," Breast Cancer, Oct. 2015, vol. 7, pp. 337-343.
Nolting B., et al., "Linker Technologies for Antibody-Drug Conjugates," Methods in Molecular Biology (Clifton, N.J.), 2013, vol. 1045, pp. 71-100.
Sambrook, "Molecular Cloning: A Laboratory Manual" Second Edition, Fritsch, eds, Cold Spring Harbor Laboratory, 1989.
Shields R.L., et al., "Lack of Fucose on Human IgG1 N-Linked Oligosaccharide Improves Binding to Human Fcgamma RIII and Antibody-Dependent Cellular Toxicity," The Journal of Biological Chemistry, 2002, vol. 277 (30), pp. 26733-26740.
Shinkawa T., et al., "The Absence of Fucose but Not the Presence of Galactose or Bisecting N-Acetylglucosamine of Human IgG1 Complex-type Oligosaccharides Shows the Critical Role of Enhancing Antibody-dependent Cellular Cytotoxicity," The Journal of Biological Chemistry, 2003, vol. 278 (5), pp. 3466-3473.
Sissom J.F., et al., "Anti-Growth Action on Mouse Mammary and Prostate Glands of a Monoclonal Antibody to Prolactin Receptor," The American journal of pathology, 1988, vol. 133 (3), pp. 589-595.
Stewart, J.M., et al., Solid Phase Peptide Synthesis, 2nd Edition, The Pierce Chemical Co., Rockford, III, 1984.
Thorpe P.E., et al., "The Preparation and Cytotoxic Properties of Antibody-toxin Conjugates," Immunological Reviews, 1982, vol. 62, pp. 119-158.
Thorpe P.E. et al., "Antibody Carriers of Cytotoxic Agents in Cancer Therapy: A Review," in: Monoclonal Antibodies '84: Biological and Clinical Applications, Pinchera., et al., Eds., 1985, pp. 485-512.
Toki B.E.., et al., "Protease-Mediated Fragmentation of p-Amidobenzyl Ethers: A New Strategy for the Activation of Anticancer Prodrugs," The Journal of Organic Chemistry, 2002, vol. 67 (6), pp. 1866-1872.
Touraine P., et al., "Increased Expression of Prolactin Receptor Gene Assessed by Quantitative Polymerase Chain Reaction in Human Breast Tumors Versus Normal Breast Tissues," The Journal of clinical endocrinology and metabolism, 1998, vol. 83 (2), pp. 667-674.
Tworoger S.S., et al., "Association Between Plasma Prolactin Concentrations and Risk of Breast Cancer Among Predominately Premenopausal Women," Cancer research, 2006, vol. 66 (4), pp. 2476-2482.
Tworoger S.S., et al., "Plasma Prolactin Concentrations and Risk of Postmenopausal Breast Cancer," Cancer research, 2004, vol. 64 (18), pp. 6814-6819.

(56) References Cited

OTHER PUBLICATIONS

Van Agthoven J., et al., "Structural Characterization of the Stem-Stem Dimerization Interface between Prolactin Receptor Chains Complexed With the Natural Hormone," Journal of Molecular Biology, 2010, vol. 404 (1), pp. 112-126.
Walker M.A., et al., "Monoclonal Antibody Mediated Intracellular Targeting of Tallysomycin S(10B)," Bioorganic & Medicinal Chemistry Letters, 2004, vol. 14 (16), pp. 4323-4327.
Walker M.A., et al., "Synthesis of an Immunoconjugate of Camptothecin," Bioorganic & Medicinal Chemistry Letters, 2002, vol. 12 (2), pp. 217-219.
Wennbo H., et al., "Activation of the Prolactin Receptor But Not the Growth Hormone Receptor is Important for Induction of Mammary Tumors in Transgenic Mice," The Journal of clinical investigation, 1997, vol. 100 (11), pp. 2744-2751.
Wennbo H., et al., "Transgenic Mice Overexpressing the Prolactin Gene Develop Dramatic Enlargement of the Prostate Gland," Endocrinology, 1997, vol. 138 (10), pp. 4410-4415.
Xu X., et al., "A Molecular Mimic of Phosphorylated Prolactin Markedly Reduced Tumor Incidence and Size When Du145 Human Prostate Cancer Cells Were Grown in Nude Mice," Cancer research, 2001, vol. 61 (16), pp. 6098-6104.
Yazaki P.J., et al., "Humanization of the Anti-Cea T84.66 Antibody Based on Crystal Structure Data," Protein Engineering, Design and Selection, 2004, vol. 17 (5), pp. 481-489.

\* cited by examiner

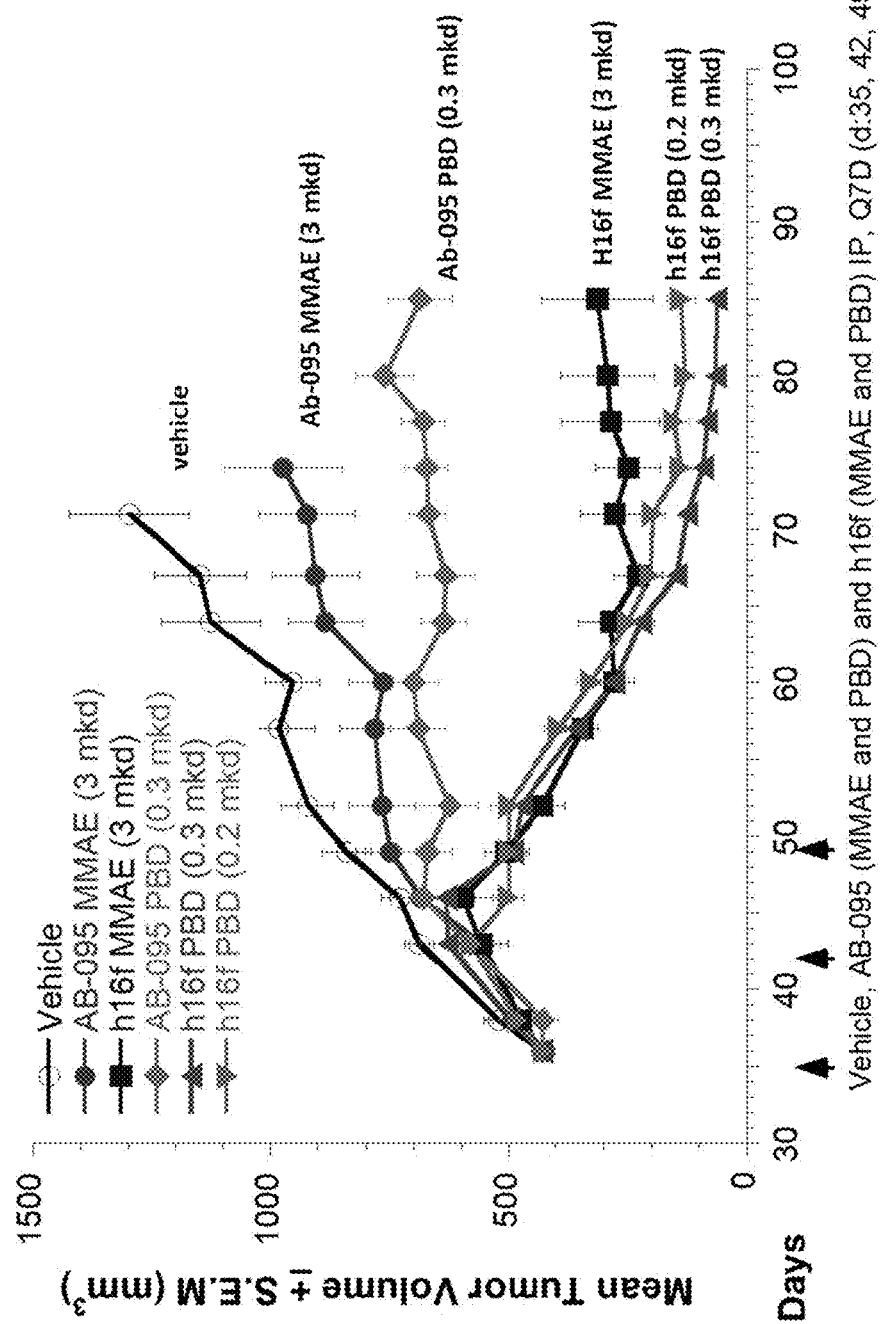

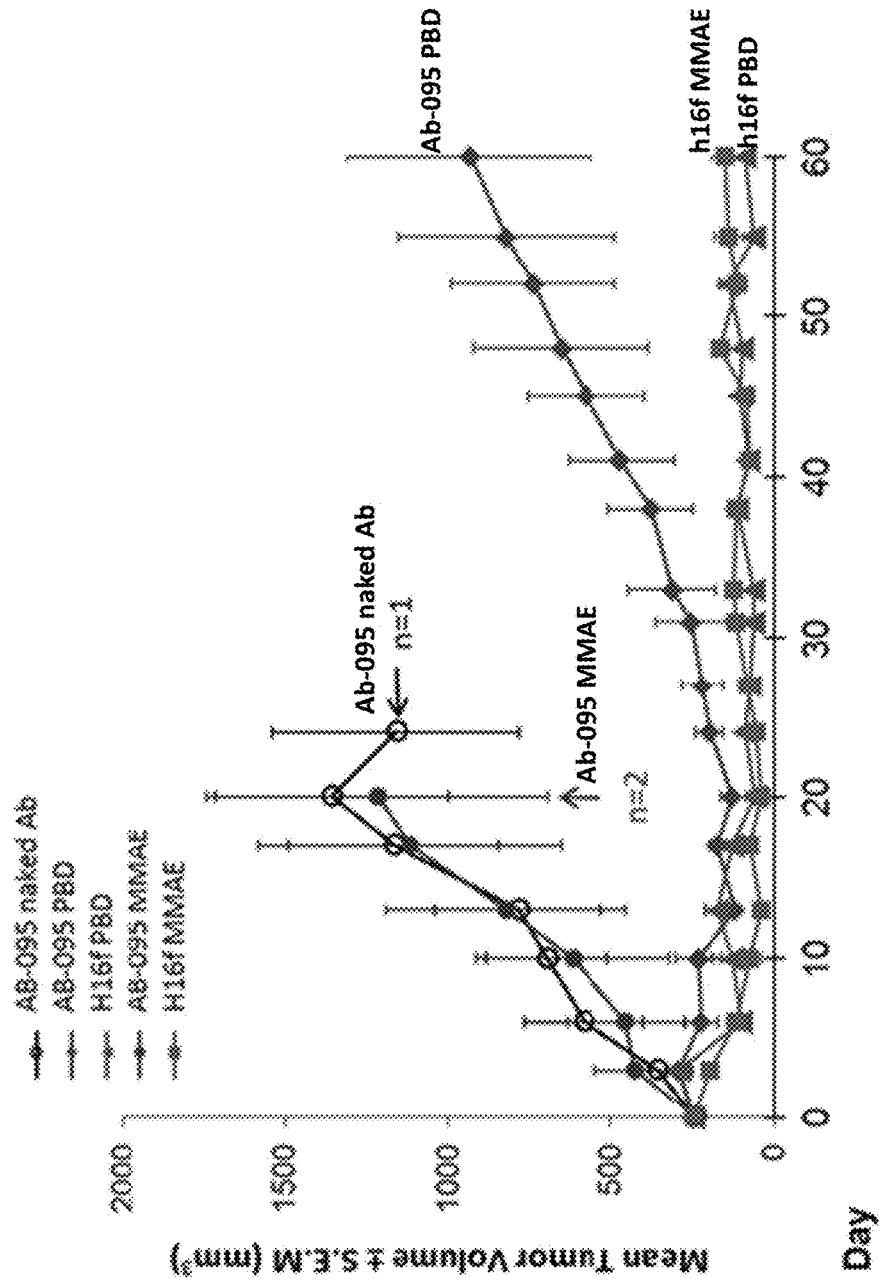

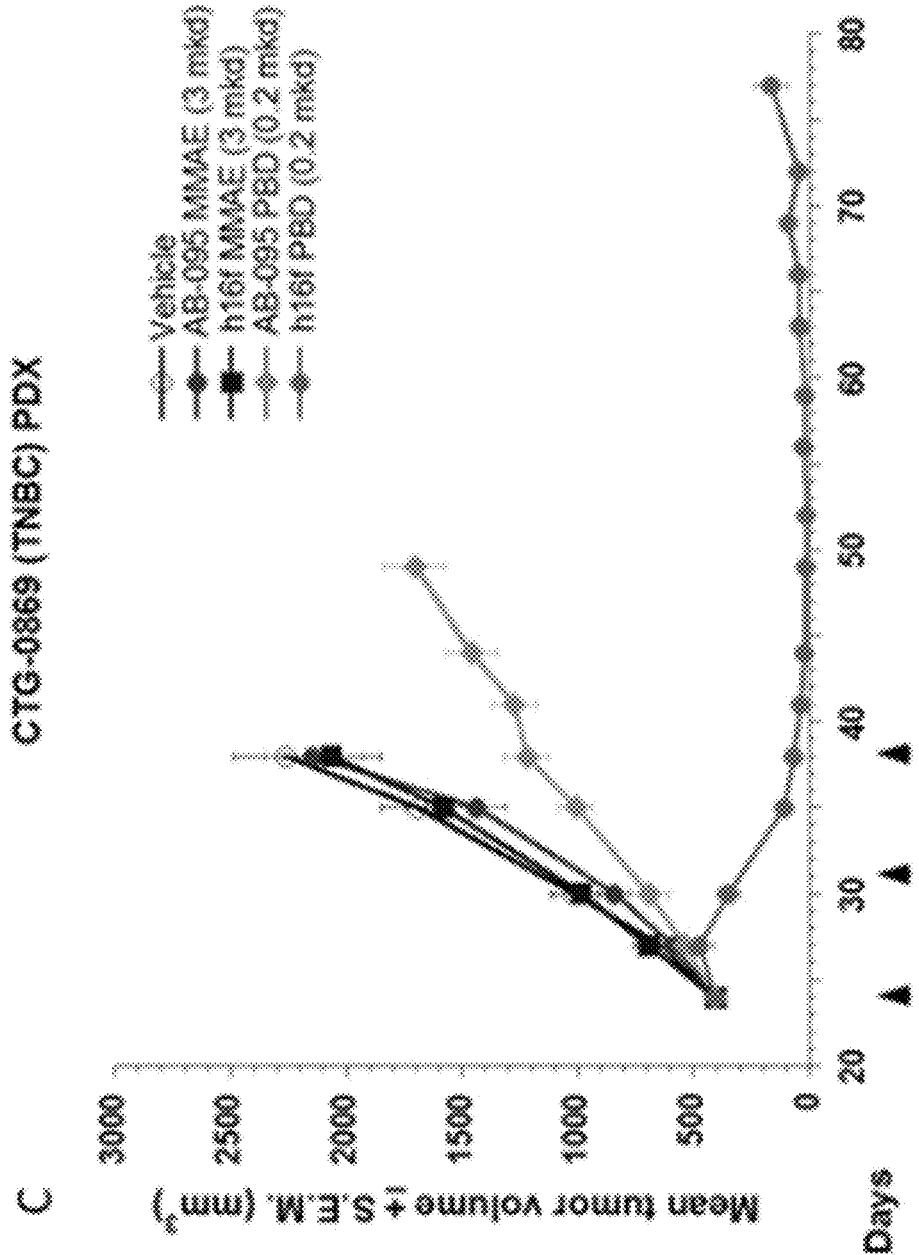

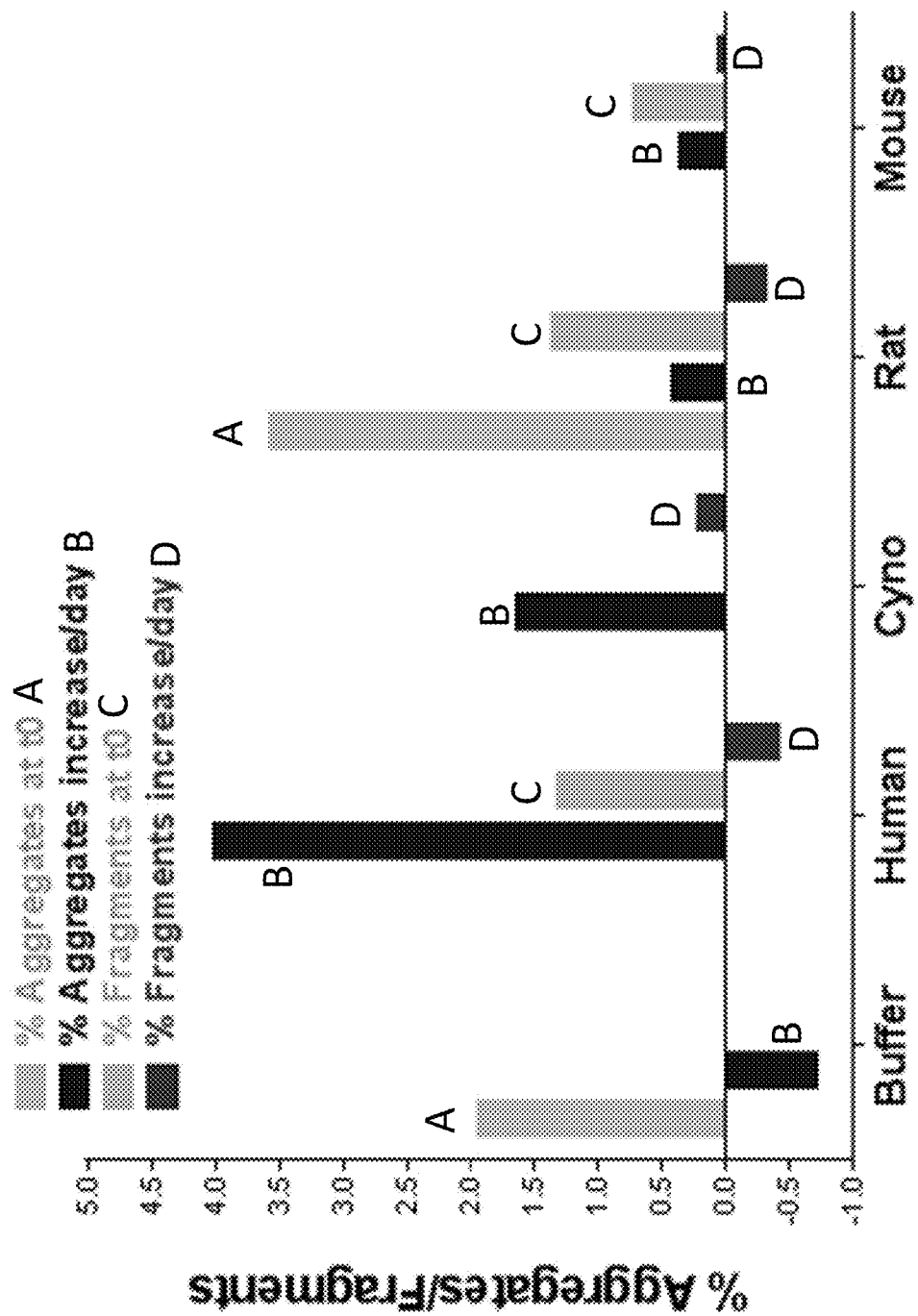

FIG. 6

Inhibition of In Vitro Proliferation of BT-474 Cells with Humanized PRLR ADC Candidates.

| ADC (MMAF DAR8)* | BT-474 IC₅₀ (nM) |
|---|---|
| AB095 | 33.40 |
| h5b** | 0.68 |
| h5d | 0.61 |
| h5e | 0.55 |
| h5f | 0.58 |
| h53e | 0.27 |
| h53f | 0.40 |
| h53b | 0.37 |
| h19e | 1.04 |
| h19f | 1.02 |
| h16a | 0.68 |
| h16c | 0.74 |
| h16f | 0.19 |
| h16g | 0.30 |
| h16h | 0.22 |
| LFA-102 | 1.05 |

* mAbs were conjugated to MMAF with DAR 8.
** Multiple humanized candidates were generated from each starting murine mAb.

FIG. 7

| Cell line (Receptor)** | PRLR RNA*** (Oncomine) | 6-Day Proliferation Assay (IC₅₀ (nM)* | | | | | Increase in PBD Potency**** |
|---|---|---|---|---|---|---|---|
| Breast Cancer Line | | h16f (S239C) PBD | Abogs-PBD | PBD Dimer | h16f MMAE | Abogs-MMAE | |
| T47D (26,000) | 168 | 0.01 | 21.14 | 0.06 | 0.02 | >22 | 21 |
| MDAMB361 | 38 | 0.04 | >22 | 0.21 | 0.06 | 9.7 | 1 |
| HCC1428 | 26 | 0.54 | >22 | 0.33 | 0.05 | 5.43 | 0.4 |
| BT-474.EP2 (10,0800) | 24 | 0.27 | 14.13 | 0.38 | 0.56 | 13.09 | 2 |
| MDAMB134VI | 22 | 0.11 | 26.2 | 0.16 | 0.04 | 11.75 | 4 |
| CAMA1 | 17 | 0.01 | 8.6 | 0.09 | 0.15 | 22.71 | 695 |
| MCF7 (8,0800) | 12 | 0.13 | 14.53 | 0.07 | >22 | >22 | >183 |
| HCC1500 | 8 | 0.28 | 17.43 | 0.1 | 0.97 | >22 | 3 |
| ZR751 | 8 | 0.04 | 11.31 | 0.05 | 4.07 | >22 | 92 |
| MDAMB415 | 4 | 0.9 | 13.44 | 0.06 | >22 | >22 | >24 |
| SKBR3 | 4 | 0.26 | 12.91 | 0.04 | 3.67 | 4.64 | 1.4 |
| HCC70 | 3 | 0.15 | 7.19 | 0.03 | >22 | >22 | >88 |
| MDAMB175VII | 2 | 30 | >22 | 0.08 | >22 | >22 | - |
| HCC38 | 2 | 25.42 | 32.82 | 0.01 | >22 | >22 | - |
| UACC812 | 2 | >22 | >22 | 0.44 | >22 | >22 | - |
| HCC1143 | 2 | 0.78 | 9.88 | 0.42 | 9.28 | 10.73 | 12 |
| MDAMB468 | 1 | 0.08 | 3.78 | 0.01 | 14.29 | 13.97 | 80 |
| BT549 | 1 | 8.26 | 19.49 | 0.02 | >22 | >22 | >3 |
| MDAMB436.FP9 (4,080) | 1 | 2.09 | 3.02 | 0.06 | 19.22 | 20.95 | - |
| MDAMB435SLM | 1 | >22 | >22 | 0.26 | >22 | >22 | N/A |
| MDAMB231LC3.1MC | 1 | 9.76 | 6.42 | 0.16 | >22 | >22 | N/A |
| JIMT-1 | 1 | 0.08 | 8.06 | 0.13 | 17.51 | 17.73 | N/A |
| HCC1187 | 0.7 | 0.19 | 0.18 | 0.05 | 13.93 | 8.06 | 157 |
| BT20 | 0.4 | 9.82 | 12.03 | 0.12 | >22 | >22 | N/A |
| SUM149PT | 0.2 | 9.82 | 12.03 | 0.08 | >22 | >22 | N/A |

FIG. 8

| Cell Line (Receptor #)*** | PRLR RNA*** (Oncomine) | 6-Day Proliferation Assay (IC50, [nM])* | | | | | Increase in PBD Potency**** |
|---|---|---|---|---|---|---|---|
| | | h16f (5228c) PBD | Ab095-PBD | PBD Dimer | h16f-MMAE | Ab095-MMAE | |
| Ovarian Cancer | | | | | | | |
| SMOV2 (2300) | n.d. | 0.16 | 17.44 | 0.02 | >22 | >22 | >138 |
| ES2 LMC | 1 | 1.5 | 21.52 | 0.18 | >22 | >22 | >15 |
| HeyA8 LMC | 0.4 | >22 | >22 | 0.39 | >22 | >22 | N/A |
| Endometrial Cancer | | | | | | | |
| AN3CA | 2 | 0.6 | 4.35 | 0.02 | 21.68 | 23.3 | 36 |
| Prostate Cancer | | | | | | | |
| 22Rv1 | 2 | 0.01 | 7.56 | 0.09 | >22 | >22 | >2200 |
| PC3 | 0.4 | >22 | >22 | 0.09 | >22 | 19.66 | N/A |
| Colon Cancer | | | | | | | |
| SW403 | 3 | 0.11 | 21.94 | 0.06 | 17.46 | 13.78 | 152 |
| LoVo | 2 | >22 | >22 | 0.13 | >22 | 15.54 | N/A |
| LS174T | 0.4 | 0.13 | 2.88 | 0.01 | >22 | >22 | 189 |
| SW48 | 0.4 | 1.97 | 2.24 | 0.02 | 21.82 | 20.37 | N/A |
| Liver Cancer | | | | | | | |
| HepG2 | 3 | 8.69 | 15.97 | 0.06 | >22 | >22 | - |
| HuH7 | 2 | 8.22 | 11.79 | 0.06 | >22 | >22 | 4 |
| Hep3B | 0.3 | 9.69 | 7.71 | 0.05 | >22 | >22 | - |
| Gastric Cancer | | | | | | | |
| IM95 | 2 | 8.60 | 18.18 | 0.17 | 19.85 | 24.15 | 4 |
| Lung Cancer | | | | | | | |
| NCI-H1048 | 2 | 3.09 | 5.32 | 0.03 | >22 | >22 | - |
| NCI-h1395 | 1 | >22 | >22 | 0.63 | >22 | >22 | N/A |
| Recombinant Expression | | | | | | | |
| HEK293/Human PRLR | | 0.01 | 1.92 | 0.02 | 0.15 | 64.72 | >15 |
| HEK293/Vector | 0.2 | 2.74 | 2.77 | 0.02 | >22 | >22 | N/A |

FIG. 9

| Model ID | ER/PR/HER2 Breast Cancer | PRLR density vs. MCF7 | Drug doses Q7Dx3 | Type of Study | PBD vs 10x MMAE ADC |
|---|---|---|---|---|---|
| CTG-0012 | TNBC BRCA deficient | 0.75 | MMAE 5 mkd, PBD 0.5 mkd | N=3 Screen | PBD=MMAE |
| CTG-0019 | HER2+ BRCA n.d. | 0.5 | MMAE 5 mkd, PBD 0.5 mkd | N=3 Screen | PBD > MMAE |
| CTG-0870 | TNBC BRCA deficient | 1.64 | MMAE 5 mkd, PBD 0.5 mkd | N=3 Screen | PBD > MMAE |
| CTG-1018 | ER+ BRCA - WT | 0.67 | MMAE 5 mkd, PBD 0.5 mkd | N=3 Screen | PBD > MMAE |
| CTG-1019 | TNBC BRCA +/- | 0.37 | MMAE 5 mkd, PBD 0.5 mkd | N=3 Screen | PBD > MMAE |
| CTG-1124 | ER+/PR+ BRCA deficient | 0.32 | MMAE 5 mkd, PBD 0.5 mkd | N=3 Screen | PBD > MMAE |
| CTG-1520 | TNBC BRCA - WT | 0.56 | MMAE 5 mkd, PBD 0.5 mkd | N=3 Screen | MMAE > PBD |
| CTG-0869 | TNBC BRCA +/- | 0.83 | MMAE 5 mkd, PBD 0.5 mkd | N=3 Screen | PBD > MMAE |

SEQUENCE LISTING

```
<160> NUMBER OF SEQ ID NOS: 31

<210> SEQ ID NO 1
<211> LENGTH: 450
<212> TYPE: PRT
<213> ORGANISM: Artificial Sequence
<220> FEATURE:
<223> OTHER INFORMATION: Synthetic

<400> SEQUENCE: 1

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Ser Asn Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Gly Gly Leu Gly Pro Ala Trp Phe Ser Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Cys Val Phe Leu Phe Pro Pro Lys Pro Lys Asp Thr Leu Met Ile
                245                 250                 255

Ser Arg Thr Pro Glu Val Thr Cys Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 2
<211> LENGTH: 120
<212> TYPE: PRT
<213> ORGANISM: Artificial Sequence
<220> FEATURE:
<223> OTHER INFORMATION: Synthetic

<400> SEQUENCE: 2

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Asn Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

```
Ala Arg Asn Gly Gly Leu Gly Pro Ala Trp Phe Ser Tyr Trp Gly Gln
            100                 105                 110

Gly Thr Leu Val Thr Val Ser Ser
        115                 120

<210> SEQ ID NO 3
<211> LENGTH: 10
<212> TYPE: PRT
<213> ORGANISM: Artificial Sequence
<220> FEATURE:
<223> OTHER INFORMATION: Synthetic

<400> SEQUENCE: 3

Gly Tyr Thr Phe Thr Thr Tyr Trp Met His
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Synthetic

<400> SEQUENCE: 4

Glu Ile Asp Pro Ser Asp Ser Tyr Ser Asn Tyr Asn Gln Lys Phe Lys
1               5                   10                  15

Asp

<210> SEQ ID NO 5
<211> LENGTH: 11
<212> TYPE: PRT
<213> ORGANISM: Artificial Sequence
<220> FEATURE:
<223> OTHER INFORMATION: Synthetic

<400> SEQUENCE: 5

Asn Gly Gly Leu Gly Pro Ala Trp Phe Ser Tyr
1               5                   10

<210> SEQ ID NO 6
<211> LENGTH: 214
<212> TYPE: PRT
<213> ORGANISM: Artificial Sequence
<220> FEATURE:
<223> OTHER INFORMATION: Synthetic

<400> SEQUENCE: 6

Asp Ile Gln Met Thr Gln Ser Pro Ser Ser Val Ser Ala Ser Val Gly
1               5                   10                  15

Asp Arg Val Thr Ile Thr Cys Lys Ala Ser Gln Tyr Val Gly Thr Ala
            20                  25                  30

Val Ala Trp Tyr Gln Gln Lys Pro Gly Lys Ser Pro Lys Leu Leu Ile
        35                  40                  45

Tyr Ser Ala Ser Asn Arg Tyr Thr Gly Val Pro Ser Arg Phe Ser Asp
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ser Ser Tyr Pro Trp
                85                  90                  95

Thr Phe Gly Gly Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 7
<211> LENGTH: 107
<212> TYPE: PRT
<213> ORGANISM: Artificial Sequence
<220> FEATURE:
<223> OTHER INFORMATION: Synthetic

<400> SEQUENCE: 7

```
Asp Ile Gln Met Thr Gln Ser Pro Ser Ser Val Ser Ala Ser Val Gly
1               5                   10                  15

Asp Arg Val Thr Ile Thr Cys Lys Ala Ser Gln Tyr Val Gly Thr Ala
            20                  25                  30

Val Ala Trp Tyr Gln Gln Lys Pro Gly Lys Ser Pro Lys Leu Leu Ile
        35                  40                  45

Tyr Ser Ala Ser Asn Arg Tyr Thr Gly Val Pro Ser Arg Phe Ser Asp
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Ser Ser Tyr Pro Trp
                85                  90                  95

Thr Phe Gly Gly Gly Thr Lys Val Glu Ile Lys
            100                 105
```

<210> SEQ ID NO 8
<211> LENGTH: 11
<212> TYPE: PRT
<213> ORGANISM: Artificial Sequence
<220> FEATURE:
<223> OTHER INFORMATION: Synthetic

<400> SEQUENCE: 8

```
Lys Ala Ser Gln Tyr Val Gly Thr Ala Val Ala
1               5                   10
```

<210> SEQ ID NO 9
<211> LENGTH: 7
<212> TYPE: PRT
<213> ORGANISM: Artificial Sequence
<220> FEATURE:
<223> OTHER INFORMATION: Synthetic

<400> SEQUENCE: 9

```
Ser Ala Ser Asn Arg Tyr Thr
1               5
```

```
<210> SEQ ID NO 10
<211> LENGTH: 9
<212> TYPE: PRT
<213> ORGANISM: Artificial Sequence
<220> FEATURE:
<223> OTHER INFORMATION: Synthetic

<400> SEQUENCE: 10

Gln Gln Tyr Ser Ser Tyr Pro Trp Thr
1               5

<210> SEQ ID NO 11
<211> LENGTH: 450
<212> TYPE: PRT
<213> ORGANISM: Artificial Sequence
<220> FEATURE:
<223> OTHER INFORMATION: Synthetic

<400> SEQUENCE: 11

Glu Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Thr Tyr
            20                  25                  30

Trp Met His Trp Val Arg Gln Ala Pro Gly Gln Gly Leu Glu Trp Ile
        35                  40                  45

Gly Glu Ile Asp Pro Ser Asp Ser Tyr Ser Asn Tyr Asn Gln Lys Phe
    50                  55                  60

Lys Asp Arg Ala Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Gly Gly Leu Gly Pro Ala Trp Phe Ser Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300
```

```
Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
            355                 360                 365

Thr Cys Leu Val Lys Gly Phe Tyr Pro Ser Asp Ile Ala Val Glu Trp
            370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 12
<211> LENGTH: 622
<212> TYPE: PRT
<213> ORGANISM: Homo sapiens

<400> SEQUENCE: 12

Met Lys Glu Asn Val Ala Ser Ala Thr Val Phe Thr Leu Leu Leu Phe
1               5                   10                  15

Leu Asn Thr Cys Leu Leu Asn Gly Gln Leu Pro Pro Gly Lys Pro Glu
                20                  25                  30

Ile Phe Lys Cys Arg Ser Pro Asn Lys Glu Thr Phe Thr Cys Trp Trp
            35                  40                  45

Arg Pro Gly Thr Asp Gly Gly Leu Pro Thr Asn Tyr Ser Leu Thr Tyr
50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
            100                 105                 110

Phe Ser Asp Glu Leu Tyr Val Asp Val Thr Tyr Ile Val Gln Pro Asp
        115                 120                 125

Pro Pro Leu Glu Leu Ala Val Glu Val Lys Gln Pro Glu Asp Arg Lys
    130                 135                 140

Pro Tyr Leu Trp Ile Lys Trp Ser Pro Pro Thr Leu Ile Asp Leu Lys
145                 150                 155                 160

Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
            180                 185                 190

Ile Leu Ser Leu His Pro Gly Gln Lys Tyr Leu Val Gln Val Arg Cys
        195                 200                 205

Lys Pro Asp His Gly Tyr Trp Ser Ala Trp Ser Pro Ala Thr Phe Ile
    210                 215                 220
```

Gln Ile Pro Ser Asp Phe Thr Met Asn Asp Thr Thr Val Trp Ile Ser
225                 230                 235                 240

Val Ala Val Leu Ser Ala Val Ile Cys Leu Ile Val Trp Ala Val
            245                 250                 255

Ala Leu Lys Gly Tyr Ser Met Val Thr Cys Ile Phe Pro Pro Val Pro
        260                 265                 270

Gly Pro Lys Ile Lys Gly Phe Asp Ala His Leu Leu Glu Lys Gly Lys
    275                 280                 285

Ser Glu Glu Leu Leu Ser Ala Leu Gly Cys Gln Asp Phe Pro Pro Thr
290                 295                 300

Ser Asp Tyr Glu Asp Leu Leu Val Glu Tyr Leu Glu Val Asp Asp Ser
305                 310                 315                 320

Glu Asp Gln His Leu Met Ser Val His Ser Lys Glu His Pro Ser Gln
                325                 330                 335

Gly Met Lys Pro Thr Tyr Leu Asp Pro Asp Thr Asp Ser Gly Arg Gly
            340                 345                 350

Ser Cys Asp Ser Pro Ser Leu Leu Ser Glu Lys Cys Glu Glu Pro Gln
        355                 360                 365

Ala Asn Pro Ser Thr Phe Tyr Asp Pro Glu Val Ile Glu Lys Pro Glu
370                 375                 380

Asn Pro Glu Thr Thr His Thr Trp Asp Pro Gln Cys Ile Ser Met Glu
385                 390                 395                 400

Gly Lys Ile Pro Tyr Phe His Ala Gly Gly Ser Lys Cys Ser Thr Trp
                405                 410                 415

Pro Leu Pro Gln Pro Ser Gln His Asn Pro Arg Ser Ser Tyr His Asn
            420                 425                 430

Ile Thr Asp Val Cys Glu Leu Ala Val Gly Pro Ala Gly Ala Pro Ala
        435                 440                 445

Thr Leu Leu Asn Glu Ala Gly Lys Asp Ala Leu Lys Ser Ser Gln Thr
450                 455                 460

Ile Lys Ser Arg Glu Glu Gly Lys Ala Thr Gln Gln Arg Glu Val Glu
465                 470                 475                 480

Ser Phe His Ser Glu Thr Asp Gln Asp Thr Pro Trp Leu Leu Pro Gln
                485                 490                 495

Glu Lys Thr Pro Phe Gly Ser Ala Lys Pro Leu Asp Tyr Val Glu Ile
            500                 505                 510

His Lys Val Asn Lys Asp Gly Ala Leu Ser Leu Leu Pro Lys Gln Arg
        515                 520                 525

Glu Asn Ser Gly Lys Pro Lys Lys Pro Gly Thr Pro Glu Asn Asn Lys
530                 535                 540

Glu Tyr Ala Lys Val Ser Gly Val Met Asp Asn Asn Ile Leu Val Leu
545                 550                 555                 560

Val Pro Asp Pro His Ala Lys Asn Val Ala Cys Phe Glu Glu Ser Ala
                565                 570                 575

Lys Glu Ala Pro Pro Ser Leu Glu Gln Asn Gln Ala Glu Lys Ala Leu
            580                 585                 590

Ala Asn Phe Thr Ala Thr Ser Ser Lys Cys Arg Leu Gln Leu Gly Gly
        595                 600                 605

Leu Asp Tyr Leu Asp Pro Ala Cys Phe Thr His Ser Phe His
610                 615                 620

<210> SEQ ID NO 13
<211> LENGTH: 209

<212> TYPE: PRT
<213> ORGANISM: Homo sapiens

<400> SEQUENCE: 13

Gln Leu Pro Pro Gly Lys Pro Glu Ile Phe Lys Cys Arg Ser Pro Asn
1               5                   10                  15

Lys Glu Thr Phe Thr Cys Trp Trp Arg Pro Gly Thr Asp Gly Gly Leu
            20                  25                  30

Pro Thr Asn Tyr Ser Leu Thr Tyr His Arg Glu Gly Glu Thr Leu Met
        35                  40                  45

His Glu Cys Pro Asp Tyr Ile Thr Gly Gly Pro Asn Ser Cys His Phe
    50                  55                  60

Gly Lys Gln Tyr Thr Ser Met Trp Arg Thr Tyr Ile Met Met Val Asn
65                  70                  75                  80

Ala Thr Asn Gln Met Gly Ser Ser Phe Ser Asp Glu Leu Tyr Val Asp
                85                  90                  95

Val Thr Tyr Ile Val Gln Pro Asp Pro Pro Leu Glu Leu Ala Val Glu
            100                 105                 110

Val Lys Gln Pro Glu Asp Arg Lys Pro Tyr Leu Trp Ile Lys Trp Ser
        115                 120                 125

Pro Pro Thr Leu Ile Asp Leu Lys Thr Gly Trp Phe Thr Leu Leu Tyr
    130                 135                 140

Glu Ile Arg Leu Lys Pro Glu Lys Ala Ala Glu Trp Glu Ile His Phe
145                 150                 155                 160

Ala Gly Gln Gln Thr Glu Phe Lys Ile Leu Ser Leu His Pro Gly Gln
                165                 170                 175

Lys Tyr Leu Val Gln Val Arg Cys Lys Pro Asp His Gly Tyr Trp Ser
            180                 185                 190

Ala Trp Ser Pro Ala Thr Phe Ile Gln Ile Pro Ser Asp Phe Thr Met
        195                 200                 205

Asn

<210> SEQ ID NO 14
<211> LENGTH: 521
<212> TYPE: PRT
<213> ORGANISM: Homo sapiens

<400> SEQUENCE: 14

Met Lys Glu Asn Val Ala Ser Ala Thr Val Phe Thr Leu Leu Leu Phe
1               5                   10                  15

Leu Asn Thr Cys Leu Leu Asn Val Gln Pro Asp Pro Pro Leu Glu Leu
            20                  25                  30

Ala Val Glu Val Lys Gln Pro Glu Asp Arg Lys Pro Tyr Leu Trp Ile
        35                  40                  45

Lys Trp Ser Pro Pro Thr Leu Ile Asp Leu Lys Thr Gly Trp Phe Thr
    50                  55                  60

Leu Leu Tyr Glu Ile Arg Leu Lys Pro Glu Lys Ala Ala Glu Trp Glu
65                  70                  75                  80

Ile His Phe Ala Gly Gln Gln Thr Glu Phe Lys Ile Leu Ser Leu His
                85                  90                  95

Pro Gly Gln Lys Tyr Leu Val Gln Val Arg Cys Lys Pro Asp His Gly
            100                 105                 110

Tyr Trp Ser Ala Trp Ser Pro Ala Thr Phe Ile Gln Ile Pro Ser Asp
        115                 120                 125

Phe Thr Met Asn Asp Thr Thr Val Trp Ile Ser Val Ala Val Leu Ser

```
                130             135             140
Ala Val Ile Cys Leu Ile Ile Val Trp Ala Val Ala Leu Lys Gly Tyr
145                 150                 155                 160

Ser Met Val Thr Cys Ile Phe Pro Pro Val Pro Gly Pro Lys Ile Lys
                165                 170                 175

Gly Phe Asp Ala His Leu Leu Glu Lys Gly Lys Ser Glu Glu Leu Leu
            180                 185                 190

Ser Ala Leu Gly Cys Gln Asp Phe Pro Pro Thr Ser Asp Tyr Glu Asp
        195                 200                 205

Leu Leu Val Glu Tyr Leu Glu Val Asp Asp Ser Glu Asp Gln His Leu
    210                 215                 220

Met Ser Val His Ser Lys Glu His Pro Ser Gln Gly Met Lys Pro Thr
225                 230                 235                 240

Tyr Leu Asp Pro Asp Thr Asp Ser Gly Arg Gly Ser Cys Asp Ser Pro
                245                 250                 255

Ser Leu Leu Ser Glu Lys Cys Glu Glu Pro Gln Ala Asn Pro Ser Thr
            260                 265                 270

Phe Tyr Asp Pro Glu Val Ile Glu Lys Pro Glu Asn Pro Glu Thr Thr
        275                 280                 285

His Thr Trp Asp Pro Gln Cys Ile Ser Met Glu Gly Lys Ile Pro Tyr
    290                 295                 300

Phe His Ala Gly Gly Ser Lys Cys Ser Thr Trp Pro Leu Pro Gln Pro
305                 310                 315                 320

Ser Gln His Asn Pro Arg Ser Ser Tyr His Asn Ile Thr Asp Val Cys
                325                 330                 335

Glu Leu Ala Val Gly Pro Ala Gly Ala Pro Ala Thr Leu Leu Asn Glu
            340                 345                 350

Ala Gly Lys Asp Ala Leu Lys Ser Ser Gln Thr Ile Lys Ser Arg Glu
        355                 360                 365

Glu Gly Lys Ala Thr Gln Gln Arg Glu Val Glu Ser Phe His Ser Glu
    370                 375                 380

Thr Asp Gln Asp Thr Pro Trp Leu Leu Pro Gln Glu Lys Thr Pro Phe
385                 390                 395                 400

Gly Ser Ala Lys Pro Leu Asp Tyr Val Glu Ile His Lys Val Asn Lys
                405                 410                 415

Asp Gly Ala Leu Ser Leu Leu Pro Lys Gln Arg Glu Asn Ser Gly Lys
            420                 425                 430

Pro Lys Lys Pro Gly Thr Pro Glu Asn Asn Lys Glu Tyr Ala Lys Val
        435                 440                 445

Ser Gly Val Met Asp Asn Asn Ile Leu Val Leu Val Pro Asp Pro His
    450                 455                 460

Ala Lys Asn Val Ala Cys Phe Glu Glu Ser Lys Glu Ala Pro Pro
465                 470                 475                 480

Ser Leu Glu Gln Asn Gln Ala Glu Lys Ala Leu Ala Asn Phe Thr Ala
                485                 490                 495

Thr Ser Ser Lys Cys Arg Leu Gln Leu Gly Gly Leu Asp Tyr Leu Asp
            500                 505                 510

Pro Ala Cys Phe Thr His Ser Phe His
        515                 520

<210> SEQ ID NO 15
<211> LENGTH: 230
<212> TYPE: PRT
<213> ORGANISM: Homo sapiens
```

<400> SEQUENCE: 15

```
Met Lys Glu Asn Val Ala Ser Ala Thr Val Phe Thr Leu Leu Leu Phe
1               5                   10                  15

Leu Asn Thr Cys Leu Leu Asn Gly Gln Leu Pro Pro Gly Lys Pro Glu
            20                  25                  30

Ile Phe Lys Cys Arg Ser Pro Asn Lys Glu Thr Phe Thr Cys Trp Trp
        35                  40                  45

Arg Pro Gly Thr Asp Gly Gly Leu Pro Thr Asn Tyr Ser Leu Thr Tyr
    50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
            100                 105                 110

Phe Ser Asp Glu Leu Tyr Val Asp Val Thr Tyr Ile Val Gln Pro Asp
        115                 120                 125

Pro Pro Leu Glu Leu Ala Val Glu Val Lys Gln Pro Glu Asp Arg Lys
    130                 135                 140

Pro Tyr Leu Trp Ile Lys Trp Ser Pro Pro Thr Leu Ile Asp Leu Lys
145                 150                 155                 160

Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
            180                 185                 190

Ile Leu Ser Leu His Pro Gly Gln Lys Tyr Leu Val Gln Val Arg Cys
        195                 200                 205

Lys Pro Asp His Gly Tyr Trp Ser Ala Trp Ser Pro Ala Thr Phe Ile
    210                 215                 220

Gln Ile Pro Ser Ala Trp
225                 230
```

<210> SEQ ID NO 16
<211> LENGTH: 376
<212> TYPE: PRT
<213> ORGANISM: Homo sapiens

<400> SEQUENCE: 16

```
Met Lys Glu Asn Val Ala Ser Ala Thr Val Phe Thr Leu Leu Leu Phe
1               5                   10                  15

Leu Asn Thr Cys Leu Leu Asn Gly Gln Leu Pro Pro Gly Lys Pro Glu
            20                  25                  30

Ile Phe Lys Cys Arg Ser Pro Asn Lys Glu Thr Phe Thr Cys Trp Trp
        35                  40                  45

Arg Pro Gly Thr Asp Gly Gly Leu Pro Thr Asn Tyr Ser Leu Thr Tyr
    50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
            100                 105                 110

Phe Ser Asp Glu Leu Tyr Val Asp Val Thr Tyr Ile Val Gln Pro Asp
        115                 120                 125
```

Pro Pro Leu Glu Leu Ala Val Glu Val Lys Gln Pro Glu Asp Arg Lys
    130                 135                 140

Pro Tyr Leu Trp Ile Lys Trp Ser Pro Pro Thr Leu Ile Asp Leu Lys
145                 150                 155                 160

Thr Gly Trp Phe Thr Leu Leu Tyr Glu Ile Arg Leu Lys Pro Glu Lys
                    165                 170                 175

Ala Ala Glu Trp Glu Ile His Phe Ala Gly Gln Gln Thr Glu Phe Lys
                180                 185                 190

Ile Leu Ser Leu His Pro Gly Gln Lys Tyr Leu Val Gln Val Arg Cys
            195                 200                 205

Lys Pro Asp His Gly Tyr Trp Ser Ala Trp Ser Pro Ala Thr Phe Ile
        210                 215                 220

Gln Ile Pro Ser Asp Phe Thr Met Asn Asp Thr Thr Val Trp Ile Ser
225                 230                 235                 240

Val Ala Val Leu Ser Ala Val Ile Cys Leu Ile Ile Val Trp Ala Val
                    245                 250                 255

Ala Leu Lys Gly Tyr Ser Met Val Thr Cys Ile Phe Pro Pro Val Pro
                260                 265                 270

Gly Pro Lys Ile Lys Gly Phe Asp Ala His Leu Leu Glu Lys Gly Lys
            275                 280                 285

Ser Glu Glu Leu Leu Ser Ala Leu Gly Cys Gln Asp Phe Pro Pro Thr
        290                 295                 300

Ser Asp Tyr Glu Asp Leu Leu Val Glu Tyr Leu Glu Val Asp Asp Ser
305                 310                 315                 320

Glu Asp Gln His Leu Met Ser Val His Ser Lys Glu His Pro Ser Gln
                    325                 330                 335

Gly Asp Pro Leu Met Leu Gly Ala Ser His Tyr Lys Asn Leu Lys Ser
                340                 345                 350

Tyr Arg Pro Arg Lys Ile Ser Ser Gln Gly Arg Leu Ala Val Phe Thr
            355                 360                 365

Lys Ala Thr Leu Thr Thr Val Gln
        370                 375

<210> SEQ ID NO 17
<211> LENGTH: 349
<212> TYPE: PRT
<213> ORGANISM: Homo sapiens

<400> SEQUENCE: 17

Met Lys Glu Asn Val Ala Ser Ala Thr Val Phe Thr Leu Leu Leu Phe
1               5                   10                  15

Leu Asn Thr Cys Leu Leu Asn Gly Gln Leu Pro Pro Gly Lys Pro Glu
            20                  25                  30

Ile Phe Lys Cys Arg Ser Pro Asn Lys Glu Thr Phe Thr Cys Trp Trp
        35                  40                  45

Arg Pro Gly Thr Asp Gly Gly Leu Pro Thr Asn Tyr Ser Leu Thr Tyr
    50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
            100                 105                 110

Phe Ser Asp Glu Leu Tyr Val Asp Val Thr Tyr Ile Val Gln Pro Asp

```
            115                 120                 125
Pro Pro Leu Glu Leu Ala Val Glu Val Lys Gln Pro Glu Asp Arg Lys
    130                 135                 140

Pro Tyr Leu Trp Ile Lys Trp Ser Pro Thr Leu Ile Asp Leu Lys
145                 150                 155                 160

Thr Gly Trp Phe Thr Leu Leu Tyr Glu Ile Arg Leu Lys Pro Glu Lys
                    165                 170                 175

Ala Ala Glu Trp Glu Ile His Phe Ala Gly Gln Gln Thr Glu Phe Lys
                180                 185                 190

Ile Leu Ser Leu His Pro Gly Gln Lys Tyr Leu Val Gln Val Arg Cys
                195                 200                 205

Lys Pro Asp His Gly Tyr Trp Ser Ala Trp Ser Pro Ala Thr Phe Ile
        210                 215                 220

Gln Ile Pro Ser Asp Phe Thr Met Asn Asp Thr Thr Val Trp Ile Ser
225                 230                 235                 240

Val Ala Val Leu Ser Ala Val Ile Cys Leu Ile Ile Val Trp Ala Val
                    245                 250                 255

Ala Leu Lys Gly Tyr Ser Met Val Thr Cys Ile Phe Pro Pro Val Pro
                260                 265                 270

Gly Pro Lys Ile Lys Gly Phe Asp Ala His Leu Leu Glu Lys Gly Lys
            275                 280                 285

Ser Glu Glu Leu Leu Ser Ala Leu Gly Cys Gln Asp Phe Pro Pro Thr
    290                 295                 300

Ser Asp Tyr Glu Asp Leu Leu Val Glu Tyr Leu Glu Val Asp Asp Ser
305                 310                 315                 320

Glu Asp Gln His Leu Met Ser Val His Ser Lys Glu His Pro Ser Gln
                    325                 330                 335

Glu Arg Glu Gln Arg Gln Ala Gln Glu Ala Arg Asp Ser
                340                 345

<210> SEQ ID NO 18
<211> LENGTH: 288
<212> TYPE: PRT
<213> ORGANISM: Homo sapiens

<400> SEQUENCE: 18

Met Lys Glu Asn Val Ala Ser Ala Thr Val Phe Thr Leu Leu Leu Phe
1               5                   10                  15

Leu Asn Thr Cys Leu Leu Asn Gly Gln Leu Pro Pro Gly Lys Pro Glu
                20                  25                  30

Ile Phe Lys Cys Arg Ser Pro Asn Lys Glu Thr Phe Thr Cys Trp Trp
            35                  40                  45

Arg Pro Gly Thr Asp Gly Gly Leu Pro Thr Asn Tyr Ser Leu Thr Tyr
50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
                100                 105                 110

Phe Ser Asp Glu Leu Tyr Val Asp Val Thr Tyr Ile Val Gln Pro Asp
            115                 120                 125

Pro Pro Leu Glu Leu Ala Val Glu Val Lys Gln Pro Glu Asp Arg Lys
    130                 135                 140
```

```
Pro Tyr Leu Trp Ile Lys Trp Ser Pro Pro Thr Leu Ile Asp Leu Lys
145                 150                 155                 160

Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
            180                 185                 190

Ile Leu Ser Leu His Pro Gly Gln Lys Tyr Leu Val Gln Val Arg Cys
        195                 200                 205

Lys Pro Asp His Gly Tyr Trp Ser Ala Trp Ser Pro Ala Thr Phe Ile
    210                 215                 220

Gln Ile Pro Ser Asp Phe Thr Met Asn Asp Thr Thr Val Trp Ile Ser
225                 230                 235                 240

Val Ala Val Leu Ser Ala Val Ile Cys Leu Ile Ile Val Trp Ala Val
                245                 250                 255

Ala Leu Lys Gly Tyr Ser Met Val Thr Cys Ile Phe Pro Pro Val Pro
            260                 265                 270

Gly Pro Lys Ile Lys Gly Phe Asp Ala His Leu Leu Glu Val Thr Pro
        275                 280                 285

<210> SEQ ID NO 19
<211> LENGTH: 268
<212> TYPE: PRT
<213> ORGANISM: Homo sapiens

<400> SEQUENCE: 19

Met Lys Glu Asn Val Ala Ser Ala Thr Val Phe Thr Leu Leu Leu Phe
1               5                   10                  15

Leu Asn Thr Cys Leu Leu Asn Gly Gln Leu Pro Pro Gly Lys Pro Glu
                20                  25                  30

Ile Phe Lys Cys Arg Ser Pro Asn Lys Glu Thr Phe Thr Cys Trp Trp
            35                  40                  45

Arg Pro Gly Thr Asp Gly Gly Leu Pro Thr Asn Tyr Ser Leu Thr Tyr
        50                  55                  60

His Arg Glu Gly Glu Thr Leu Met His Glu Cys Pro Asp Tyr Ile Thr
65                  70                  75                  80

Gly Gly Pro Asn Ser Cys His Phe Gly Lys Gln Tyr Thr Ser Met Trp
                85                  90                  95

Arg Thr Tyr Ile Met Met Val Asn Ala Thr Asn Gln Met Gly Ser Ser
            100                 105                 110

Phe Ser Asp Glu Leu Tyr Val Asp Val Thr Tyr Ile Val Gln Pro Asp
        115                 120                 125

Pro Pro Leu Glu Leu Ala Val Glu Val Lys Gln Pro Glu Asp Arg Lys
    130                 135                 140

Pro Tyr Leu Trp Ile Lys Trp Ser Pro Pro Thr Leu Ile Asp Leu Lys
145                 150                 155                 160

Thr Gly Trp Phe Thr Leu Leu Tyr Glu Ile Arg Leu Lys Pro Glu Lys
                165                 170                 175

Ala Ala Glu Trp Glu Ile His Phe Ala Gly Gln Gln Thr Glu Phe Lys
            180                 185                 190

Ile Leu Ser Leu His Pro Gly Gln Lys Tyr Leu Val Gln Val Arg Cys
        195                 200                 205

Lys Pro Asp His Gly Tyr Trp Ser Ala Trp Ser Pro Ala Thr Phe Ile
    210                 215                 220

Gln Ile Pro Ser Gly Asp Pro Leu Met Leu Gly Ala Ser His Tyr Lys
225                 230                 235                 240
```

Asn Leu Lys Ser Tyr Arg Pro Arg Lys Ile Ser Ser Gln Gly Arg Leu
            245                 250                 255

Ala Val Phe Thr Lys Ala Thr Leu Thr Thr Val Gln
            260                 265

<210> SEQ ID NO 20
<211> LENGTH: 217
<212> TYPE: PRT
<213> ORGANISM: Homo sapiens

<400> SEQUENCE: 20

Met His Glu Cys Pro Asp Tyr Ile Thr Gly Gly Pro Asn Ser Cys His
1               5                   10                  15

Phe Gly Lys Gln Tyr Thr Ser Met Trp Arg Thr Tyr Ile Met Met Val
            20                  25                  30

Asn Ala Thr Asn Gln Met Gly Ser Ser Phe Ser Asp Glu Leu Tyr Val
        35                  40                  45

Asp Val Thr Tyr Ile Val Gln Pro Asp Pro Pro Leu Glu Leu Ala Val
    50                  55                  60

Glu Val Lys Gln Pro Glu Asp Arg Lys Pro Tyr Leu Trp Ile Lys Trp
65                  70                  75                  80

Ser Pro Pro Thr Leu Ile Asp Leu Lys Thr Gly Trp Phe Thr Leu Leu
                85                  90                  95

Tyr Glu Ile Arg Leu Lys Pro Glu Lys Ala Ala Glu Trp Glu Ile His
            100                 105                 110

Phe Ala Gly Gln Gln Thr Glu Phe Lys Ile Leu Ser Leu His Pro Gly
        115                 120                 125

Gln Lys Tyr Leu Val Gln Val Arg Cys Lys Pro Asp His Gly Tyr Trp
    130                 135                 140

Ser Ala Trp Ser Pro Ala Thr Phe Ile Gln Ile Pro Ser Asp Phe Thr
145                 150                 155                 160

Met Asn Asp Thr Thr Val Trp Ile Ser Val Ala Val Leu Ser Ala Val
                165                 170                 175

Ile Cys Leu Ile Ile Val Trp Ala Val Ala Leu Lys Gly Tyr Ser Met
            180                 185                 190

Val Thr Cys Ile Phe Pro Pro Val Pro Gly Pro Lys Ile Lys Gly Phe
        195                 200                 205

Asp Ala His Leu Leu Glu Val Thr Pro
    210                 215

<210> SEQ ID NO 21
<211> LENGTH: 450
<212> TYPE: PRT
<213> ORGANISM: artificial
<220> FEATURE:
<223> OTHER INFORMATION: Synthetic

<400> SEQUENCE: 21

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Ile His Trp Val Arg Gln Ala Pro Gly Gln Gly Leu Glu Trp Ile
        35                  40                  45

Gly Tyr Ile Tyr Pro Asn Asn Asp Gly Thr Gly Tyr Asn Gln Lys Phe
    50                  55                  60

-continued

```
Lys Ser Arg Ala Thr Leu Thr Val Asp Asn Ser Thr Ser Thr Ala Tyr
 65                  70                  75                  80

Met Glu Leu Arg Ser Leu Arg Ser Asp Asp Thr Ala Val Tyr Tyr Cys
                 85                  90                  95

Ala Arg Gly Asp Gly Asn Tyr Val Gly Asp Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Leu Leu Gly Gly
225                 230                 235                 240

Pro Cys Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 22
<211> LENGTH: 120
<212> TYPE: PRT
```

<213> ORGANISM: Artificial Sequence
<220> FEATURE:
<223> OTHER INFORMATION: Synthetic

<400> SEQUENCE: 22

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Ile His Trp Val Arg Gln Ala Pro Gly Gln Gly Leu Glu Trp Ile
        35                  40                  45

Gly Tyr Ile Tyr Pro Asn Asn Asp Gly Thr Gly Tyr Asn Gln Lys Phe
    50                  55                  60

Lys Ser Arg Ala Thr Leu Thr Val Asp Asn Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Asp Gly Asn Tyr Val Gly Asp Met Asp Tyr Trp Gly Gln
            100                 105                 110

Gly Thr Thr Val Thr Val Ser Ser
        115                 120

<210> SEQ ID NO 23
<211> LENGTH: 10
<212> TYPE: PRT
<213> ORGANISM: Artificial Sequence
<220> FEATURE:
<223> OTHER INFORMATION: Synthetic

<400> SEQUENCE: 23

Gly Tyr Thr Phe Thr Asp Tyr Asn Ile His
1               5                   10

<210> SEQ ID NO 24
<211> LENGTH: 17
<212> TYPE: PRT
<213> ORGANISM: Artificial Sequence
<220> FEATURE:
<223> OTHER INFORMATION: Synthetic

<400> SEQUENCE: 24

Tyr Ile Tyr Pro Asn Asn Asp Gly Thr Gly Tyr Asn Gln Lys Phe Lys
1               5                   10                  15

Ser

<210> SEQ ID NO 25
<211> LENGTH: 11
<212> TYPE: PRT
<213> ORGANISM: Artificial Sequence
<220> FEATURE:
<223> OTHER INFORMATION: Synthetic

<400> SEQUENCE: 25

Gly Asp Gly Asn Tyr Val Gly Asp Met Asp Tyr
1               5                   10

<210> SEQ ID NO 26
<211> LENGTH: 214
<212> TYPE: PRT
<213> ORGANISM: Artificial Sequence
<220> FEATURE:
<223> OTHER INFORMATION: Synthetic

```
<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Pro Lys Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ala Thr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
        210

<210> SEQ ID NO 27
<211> LENGTH: 107
<212> TYPE: PRT
<213> ORGANISM: Artificial Sequence
<220> FEATURE:
<223> OTHER INFORMATION: Synthetic

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Asn Ile Tyr Ser Tyr
            20                  25                  30

Leu Ala Trp Tyr Gln Gln Lys Pro Gly Lys Pro Pro Lys Leu Leu Val
        35                  40                  45

Tyr Asn Ala Lys Thr Leu Ala Glu Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His His Tyr Ala Thr Pro Phe
                85                  90                  95

Thr Phe Gly Gln Gly Thr Lys Leu Glu Ile Lys
            100                 105

<210> SEQ ID NO 28
<211> LENGTH: 11
<212> TYPE: PRT
```

```
<213> ORGANISM: Artificial Sequence
<220> FEATURE:
<223> OTHER INFORMATION: Synthetic

<400> SEQUENCE: 28

Arg Ala Ser Glu Asn Ile Tyr Ser Tyr Leu Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Synthetic

<400> SEQUENCE: 29

Asn Ala Lys Thr Leu Ala Glu
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic

<400> SEQUENCE: 30

Gln His His Tyr Ala Thr Pro Phe Thr
1               5

<210> SEQ ID NO 31
<211> LENGTH: 450
<212> TYPE: PRT
<213> ORGANISM: Artificial Sequence
<220> FEATURE:
<223> OTHER INFORMATION: Synthetic

<400> SEQUENCE: 31

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Ile His Trp Val Arg Gln Ala Pro Gly Gln Gly Leu Glu Trp Ile
        35                  40                  45

Gly Tyr Ile Tyr Pro Asn Asn Asp Gly Thr Gly Tyr Asn Gln Lys Phe
    50                  55                  60

Lys Ser Arg Ala Thr Leu Thr Val Asp Asn Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Asp Gly Asn Tyr Val Gly Asp Met Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

|      | 180 |     |     |     | 185 |     |     |     | 190 |     |     |     |
| ---- | --- | --- | --- | --- | --- | --- | --- | --- | --- | --- | --- | --- |
| Ser | Ser | Ser | Leu | Gly | Thr | Gln | Thr | Tyr | Ile | Cys | Asn | Val | Asn | His | Lys |
|     | 195 |     |     |     |     | 200 |     |     |     |     | 205 |

```
              180                 185                 190
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
        210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Glu Glu Met Thr Lys Asn Gln Val Ser Leu
                355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
        435                 440                 445

Gly Lys
450
```

ANTI-PRLR ANTIBODY-DRUG CONJUGATES (ADC) AND USES THEREOF

CROSS-REFERENCE TO RELATED APPLICATIONS

The present application claims priority to U.S. Provisional Patent Application Ser. No. 62/482,640, filed Apr. 6, 2017, the disclosure of which is hereby incorporated by reference in its entirety.

FIELD OF THE INVENTION

The present application pertains to, among other things, anti-prolactin receptor (PRLR) antibody drug conjugates (ADCs), compositions including ADCs, methods of making ADCs, and uses thereof.

BACKGROUND

Cancer therapies comprise a wide range of therapeutic approaches, including surgery, radiation, and chemotherapy. While the often complementary approaches allow a broad selection to be available to the medical practitioner to treat the cancer, existing therapeutics suffer from a number of disadvantages, such as a lack of selectivity of targeting cancer cells over normal, healthy cells, and the development of resistance by the cancer to the treatment.

Recent approaches to treating cancer based on targeted therapeutics, such as antibodies, have led to chemotherapeutic regimens with fewer side effects as compared to non-targeted therapies such as radiation treatment. One effective approach for enhancing the anti-tumor-potency of antibodies involves linking cytotoxic drugs or toxins to monoclonal antibodies that are capable of being internalized by a target cell. These agents are termed antibody-drug conjugates (ADCs). Upon administration to a patient, ADCs bind to target cells via their antibody portions and become internalized, allowing the drugs or toxins to exert their effect (see, e.g., U.S. Patent Appl. Publ. Nos. US2005/0180972 and US2005/0123536).

Prolactin receptor (PRLR) is a single membrane-spanning class 1 cytokine receptor that is homologous to receptors for members of the cytokine superfamily, such as the receptors for IL2, IL3, IL4, IL6, IL7, erythropoietin, and GM-CSF. PRLR is involved in multiple biological functions, including cell growth, differentiation, development, lactation and reproduction. It has no intrinsic tyrosine kinase activity; however, ligand binding has been shown to lead to receptor dimerization, cross-phosphorylation of Jak2 and downstream signaling. Human prolactin receptor cDNA was originally isolated from hepatoma and breast cancer libraries (Boutin et al., Molec. Endocr. 3: 1455-1461, 1989). The nucleotide sequence predicted a mature protein of 598 amino acids with a much longer cytoplasmic domain than the rat liver PRL receptor. The prolactin receptor gene resides in the same chromosomal region as the growth hormone receptor gene, which has been mapped to 5;13-p 12 (Arden, K. C. et al. Cytogenet. Cell Gene 53: 161-165, 1990; Arden, K. C. et al., (Abstract) AM. J. Hum. Genet. 45 (suppl.): A129 only, 1989). Growth hormone also binds to the prolactin receptor and activates the receptor.

PRLR exists in a number of different isoforms that differ in the length of their cytoplasmic domains. Four PRLR mRNA isoforms (L, I, S1a, and S1b) have been identified in human subcutaneous abdominal adipose tissue and breast adipose tissue (Ling, C. et al., J. Clin. Endocr. Metab. 88: 1804-1808, 2003). In addition, expression of both L-PRLR and I-PRLR has been detected in human subcutaneous abdominal adipose tissue and breast adipose tissue using immunoblot analysis. Recent reports have suggested PRLR is expressed and activated in human breast cancer and prostate cancer tissues (Li et al., Cancer Res., 64:4774-4782, 2004; Gill et al., J Clin Pathol., 54:956-960, 2001; Touraine et al., J Clin Endocrinol Metab., 83:667-674, 1998). Reportedly, Stat5 activation and PRLR expression is associated with high histological grade in 54% of prostate cancer specimens (Li et al., supra). Other reports suggest primary breast cancer specimens are responsive to PRL in colony formation assays, and that plasma PRL concentrations correlate with breast cancer risk (Tworoger et al., Cancer Res., 64:6814-6819, 2004; Tworoger et al., Cancer Res., 66:2476-2482, 2006). In another report, PRL transgenic mice developed malignant mammary carcinomas or prostate hyperplasia (Wennbo et al., J Clin Invest., 100:2744-2751, 1997; Wennbo et al., Endocrinology, 138:4410-4415, 1997). Blockade of PRLR signaling may be a means for treating breast and prostate cancer. (See, e.g., Damiano and Wasserman, April 2013, Clin. Cancer Res. 19(7):1644-1650).

Thus, there is a need in the art for novel PRLR antagonists for the treatment of cancer and other disorders associated with detrimental PRLR activity.

SUMMARY OF THE INVENTION

The present invention provides antibody drug conjugates (ADCs) comprising a cytotoxic and/or cytostatic agent linked to an anti-PRLR antibody by way of a linker, compositions comprising the ADCs of the invention, methods of making the ADCs of the invention and methods of treating a cancer comprising administering to a subject having cancer the ADCs of the invention. As described in more detail in the Examples, and while not intending to be bound by any particular theory of operation, data included herein demonstrate anti-PRLR ADCs comprising specific linkers and specific cytotoxic and/or cytostatic agents (i.e., a pyrrolobenzodiazepine (PBD) warhead), exert potent anti-tumor activities. Moreover, the anti-PRLR ADCs of the present invention are characterized by a low drug to antibody ratio (DAR), where low drug loading surprisingly provides a highly efficacious ADC.

Accordingly, in one aspect, the present disclosure provides ADCs that specifically bind PRLR, and in particular human PRLR (huPRLR).

In one aspect, the invention provides an antibody drug conjugate (ADC) comprising a cytotoxic and/or cytostatic agent linked to an antibody by way of a linker, wherein the antibody drug conjugate is a compound according to structural Formula (I):

[D-L-XY]$n$-Ab         (I), or a salt thereof, wherein D comprises a pyrrolobenzodiazepine (PBD) dimer; L is a linker; Ab is an anti-prolactin receptor (PRLR) antibody comprising (i.) a heavy chain variable region comprising a CDRH1 sequence comprising SEQ ID NO: 3, a CDRH2 sequence comprising SEQ ID NO: 4, and a CDRH3 sequence comprising SEQ ID NO: 5; (ii.) a light chain variable region comprising a CDRL1 sequence comprising SEQ ID NO: 8, a CDRL2 sequence comprising SEQ ID NO: 9, and a CDRL3 sequence comprising SEQ ID NO: 10; and (iii.) a mutation comprising S239C in a heavy chain constant region, wherein the numbering is in accordance with Kabat; XY represents a covalent linkage linking linker L to antibody Ab; and n is any integer. In one embodiment, n is 2 or 4. In one embodiment, n is 2. In preferred embodiments, n is about 2. In certain embodiments, XY is a linkage formed with a sulfhydryl group on antibody Ab. In one embodiment, XY is a maleimide-sulfhydryl linkage. In certain embodiments, L comprises the linker as described in Formula III, IV, V, VI, VII, VIII, or IX. In preferred embodiments, L comprises the linker as described in Formula IX. In certain embodiments, the anti-PRLR antibody comprises an IgG1 isotype. In certain embodiments, the heavy chain constant region of the anti-PRLR antibody either lacks a C-terminal lysine or comprises an amino acid other than lysine at a C-terminus of the heavy chain constant region. In exemplary embodiments, the anti-PRLR antibody is a humanized antibody.

In another aspect, the invention provides an antibody drug conjugate (ADC) comprising a cytotoxic and/or cytostatic agent linked to an antibody by way of a linker, wherein the antibody drug conjugate is a compound according to structural Formula (I):

[D-L-XY]$n$-Ab (I), or a salt thereof, wherein D comprises a pyrrolobenzodiazepine (PBD) dimer; L is a linker; Ab is an anti-prolactin receptor (PRLR) antibody comprising (i.) a heavy chain variable region comprising SEQ ID NO: 2; (ii.) a light chain variable region comprising SEQ ID NO: 7; and (iii.) a mutation comprising S239C in a heavy chain constant region, wherein the numbering is in accordance with Kabat; XY represents a covalent linkage linking linker L to antibody Ab; and n is any integer. In one embodiment, n is 2 or 4. In one embodiment, n is 2. In preferred embodiments, n is about 2. In certain embodiments, XY is a linkage formed with a sulfhydryl group on antibody Ab. In one embodiment, XY is a maleimide-sulfhydryl linkage. In certain embodiments, L comprises the linker as described in Formula III, IV, V, VI, VII, VIII, or IX. In preferred embodiments, L comprises the linker as described in Formula IX. In certain embodiments, the anti-PRLR antibody comprises an IgG1 isotype. In certain embodiments, the heavy chain constant region of the anti-PRLR antibody either lacks a C-terminal lysine or comprises an amino acid other than lysine at a C-terminus of the heavy chain constant region. In exemplary embodiments, the anti-PRLR antibody is a humanized antibody.

In another aspect, the invention provides an antibody drug conjugate (ADC) comprising a cytotoxic and/or cytostatic agent linked to an antibody by way of a linker, wherein the antibody drug conjugate is a compound according to structural Formula (I):

[D-L-XY]$n$-Ab (I), or a salt thereof, wherein D comprises a pyrrolobenzodiazepine (PBD) dimer; L is a linker; Ab is an anti-prolactin receptor (PRLR) antibody comprising (i.) a heavy chain comprising the amino acid sequence set forth in SEQ ID NO: 1, (ii.) a light chain comprising the amino acid sequence set forth in SEQ ID NO: 6; XY represents a covalent linkage linking linker L to antibody Ab; and n is any integer. In one embodiment, n is 2 or 4. In one embodiment, n is 2. In preferred embodiments, n is about 2. In certain embodiments, XY is a linkage formed with a sulfhydryl group on antibody Ab. In one embodiment, XY is a maleimide-sulfhydryl linkage. In certain embodiments, L comprises the linker as described in Formula III, IV, V, VI, VII, VIII, or IX. In preferred embodiments, L comprises the linker as described in Formula IX. In one embodiment, the anti-PRLR antibody comprises an IgG isotype. In certain embodiments, the anti-PRLR antibody comprises an IgG1 isotype. In certain embodiments, the heavy chain constant region of the anti-PRLR antibody either lacks a C-terminal lysine or comprises an amino acid other than lysine at a C-terminus of the heavy chain constant region. In exemplary embodiments, the anti-PRLR antibody is a humanized antibody.

In another aspect, the invention features an ADC comprising the structure of Formula (X)

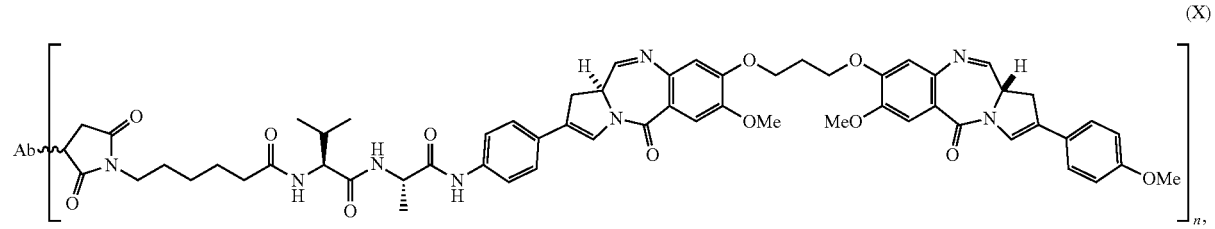

or a salt thereof, wherein Ab comprises an anti-PRLR antibody comprising: (i.) a heavy chain variable region comprising a CDRH1 sequence comprising SEQ ID NO: 3, a CDRH2 sequence comprising SEQ ID NO: 4, and a CDRH3 sequence comprising SEQ ID NO: 5; (ii.) a light chain variable region comprising a CDRL1 sequence comprising SEQ ID NO: 8, a CDRL2 sequence comprising SEQ ID NO: 9, and a CDRL3 sequence comprising SEQ ID NO: 10; (iii.) a mutation comprising S239C in a heavy chain constant region, wherein the numbering is in accordance with Kabat; and (iv.) wherein n is 2 or about 2. In one embodiment, the heavy chain variable region comprises SEQ ID NO: 2 and the light chain variable region comprises SEQ ID NO: 7. In one embodiment, the ADC comprises a full heavy chain comprising SEQ ID NO: 1, and a full light chain comprising SEQ ID NO: 6. In certain embodiments, the anti-PRLR antibody comprises an IgG1 isotype. In certain embodiments, the heavy chain constant region of the anti-PRLR antibody either lacks a C-terminal lysine or comprises an amino acid other than lysine at a C-terminus of the heavy chain constant region. In exemplary embodiments, the anti-PRLR antibody is a humanized antibody.

In another aspect, the invention the invention features an ADC comprising the structure of Formula (X)

(X)

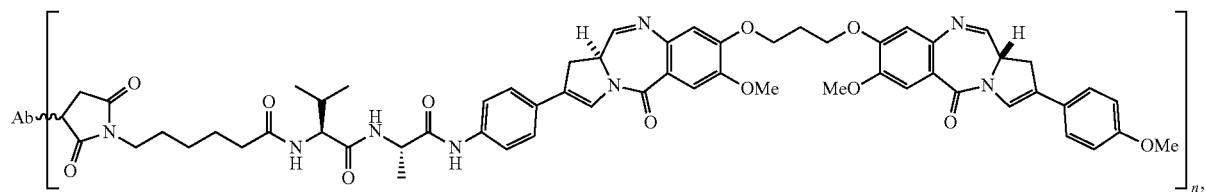

or a salt thereof, wherein Ab comprises an anti-PRLR antibody comprising: (i.) a heavy chain variable region comprising SEQ ID NO: 2; (ii.) a light chain variable region comprising SEQ ID NO: 7; (iii.) a mutation comprising S239C in a heavy chain constant region, wherein the numbering is in accordance with Kabat; and (iv.) wherein n is 2 or about 2. In one embodiment, the ADC comprises a full heavy chain comprising SEQ ID NO: 1, and a full light chain comprising SEQ ID NO: 6. In certain embodiments, the anti-PRLR antibody comprises an IgG1 isotype. In certain embodiments, the heavy chain constant region of the anti-PRLR antibody either lacks a C-terminal lysine or comprises an amino acid other than lysine at a C-terminus of the heavy chain constant region. In exemplary embodiments, the anti-PRLR antibody is a humanized antibody.

In another aspect, the invention features an ADC comprising the structure of Formula (X)

and wherein the antibody comprises a heavy chain comprising the amino acid sequence set forth in SEQ ID NO: 1, and a light chain comprising the amino acid sequence set forth in SEQ ID NO: 6.

In an even further aspect, the invention provides a method of making an ADC, comprising contacting an anti-PRLR antibody with a synthon according to structural Formula (Ia) D-L-R$^x$, wherein D is a cytotoxic and/or cytostatic agent capable of crossing a cell membrane, L is a linker capable of being cleaved by a lysosomal enzyme, and R$^x$ comprises a functional group capable of linking the synthon to the antibody, under conditions in which the synthon covalently links the synthon to the antibody, wherein D is a PBD dimer, and wherein the antibody comprises (i.) a heavy chain variable region comprising a CDRH1 sequence comprising SEQ ID NO: 3, a CDRH2 sequence comprising SEQ ID NO: 4, and a CDRH3 sequence comprising SEQ ID NO: 5; (ii.)

(X)

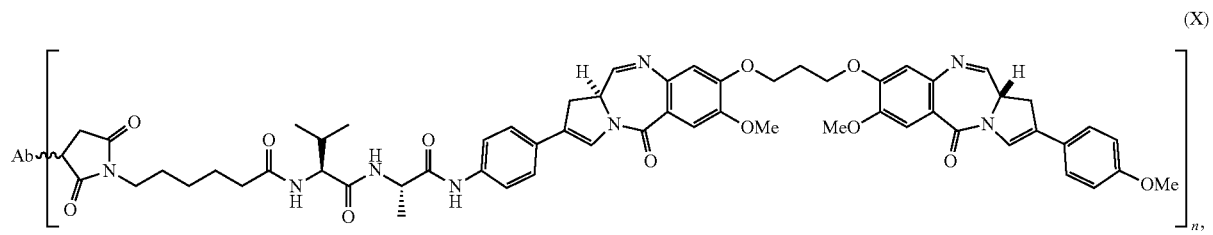

or a salt thereof, wherein Ab comprises an anti-PRLR antibody comprising a heavy chain comprising SEQ ID NO: 1 and a light chain comprising SEQ ID NO: 6, wherein n is 2 or about 2.

In one aspect, the invention provides a composition comprising an ADC described herein and an excipient, a carrier, and/or a diluent. In one embodiment, the composition is a pharmaceutical composition. In one embodiment, the composition of the invention is formulated for pharmaceutical use in humans.

In a further aspect, the invention provides for a kit comprising at least one dose of an ADC according to any aspect of the present disclosure and at least one dose of at least one additional therapeutic, wherein the at least one additional therapeutic is optionally combined with the pharmaceutical composition.

In an even further aspect, the invention provides a method of making an ADC, comprising contacting an anti-PRLR antibody with a synthon according to structural Formula (Ia) D-L-R$^x$, wherein D is a cytotoxic and/or cytostatic agent capable of crossing a cell membrane, L is a linker capable of being cleaved by a lysosomal enzyme, and R$^x$ comprises a functional group capable of linking the synthon to the antibody, under conditions in which the synthon covalently links the synthon to the antibody, wherein D is a PBD dimer, a light chain variable region comprising a CDRL1 sequence comprising SEQ ID NO: 8, a CDRL2 sequence comprising SEQ ID NO: 9, and a CDRL3 sequence comprising SEQ ID NO: 10; and (iii.) a mutation comprising S239C in a heavy chain constant region, wherein the numbering is in accordance with Kabat. In certain embodiments, the anti-PRLR antibody comprises an IgG1 isotype. In certain embodiments, the heavy chain constant region of the anti-PRLR antibody either lacks a C-terminal lysine or comprises an amino acid other than lysine at a C-terminus of the heavy chain constant region. In exemplary embodiments, the anti-PRLR antibody is a humanized antibody.

In an even further aspect, the invention provides a method of making an ADC, comprising contacting an anti-PRLR antibody with a synthon according to structural Formula (Ia) D-L-R$^x$, wherein D is a cytotoxic and/or cytostatic agent capable of crossing a cell membrane, L is a linker capable of being cleaved by a lysosomal enzyme, and R$^x$ comprises a functional group capable of linking the synthon to the antibody, under conditions in which the synthon covalently links the synthon to the antibody, wherein D is a PBD dimer, and wherein the antibody comprises (i.) a heavy chain variable region comprising a CDRH1 sequence comprising SEQ ID NO: 3, a CDRH2 sequence comprising SEQ ID NO: 4, and a CDRH3 sequence comprising SEQ ID NO: 5; (ii.)

a light chain variable region comprising a CDRL1 sequence comprising SEQ ID NO: 8, a CDRL2 sequence comprising SEQ ID NO: 9, and a CDRL3 sequence comprising SEQ ID NO: 10; and (iii.) a mutation comprising S239C in a heavy chain constant region, wherein the numbering is in accordance with Kabat; and wherein $R^x$ is a sulfhydryl group or a maleimide-sulfhydryl group. In certain embodiments, the anti-PRLR antibody comprises an IgG1 isotype. In certain embodiments, the heavy chain constant region of the anti-PRLR antibody either lacks a C-terminal lysine or comprises an amino acid other than lysine at a C-terminus of the heavy chain constant region. In exemplary embodiments, the anti-PRLR antibody is a humanized antibody.

In an even further aspect, the invention provides a method of making an ADC, comprising contacting an anti-PRLR antibody with a synthon according to structural Formula (Ia) D-L-$R^x$, wherein D is a cytotoxic and/or cytostatic agent capable of crossing a cell membrane, L is a linker capable of being cleaved by a lysosomal enzyme, and $R^x$ comprises a functional group capable of linking the synthon to the antibody, under conditions in which the synthon covalently links the synthon to the antibody, wherein D is a PBD dimer; wherein L comprises the linker as described in Formula III, IV, V, VI, VII, VIII, or IX; and wherein the antibody comprises (i.) a heavy chain variable region comprising a CDRH1 sequence comprising SEQ ID NO: 3, a CDRH2 sequence comprising SEQ ID NO: 4, and a CDRH3 sequence comprising SEQ ID NO: 5; (ii.) a light chain variable region comprising a CDRL1 sequence comprising SEQ ID NO: 8, a CDRL2 sequence comprising SEQ ID NO: 9, and a CDRL3 sequence comprising SEQ ID NO: 10; and (iii.) a mutation comprising S239C in a heavy chain constant region, wherein the numbering is in accordance with Kabat; and wherein $R^x$ is a sulfhydryl group or a maleimide-sulfhydryl group. In certain embodiments, the anti-PRLR antibody comprises an IgG1 isotype. In certain embodiments, the heavy chain constant region of the anti-PRLR antibody either lacks a C-terminal lysine or comprises an amino acid other than lysine at a C-terminus of the heavy chain constant region. In exemplary embodiments, the anti-PRLR antibody is a humanized antibody.

In an even further aspect, the invention provides a method of making an ADC, comprising contacting an anti-PRLR antibody with a synthon according to structural Formula (Ia) D-L-$R^x$, wherein D is a cytotoxic and/or cytostatic agent capable of crossing a cell membrane, L is a linker capable of being cleaved by a lysosomal enzyme, and $R^x$ comprises a functional group capable of linking the synthon to the antibody, under conditions in which the synthon covalently links the synthon to the antibody, wherein D is a PBD dimer; wherein L comprises the linker as described in Formula IX; and wherein the antibody comprises (i.) a heavy chain variable region comprising a CDRH1 sequence comprising SEQ ID NO: 3, a CDRH2 sequence comprising SEQ ID NO: 4, and a CDRH3 sequence comprising SEQ ID NO: 5; (ii.) a light chain variable region comprising a CDRL1 sequence comprising SEQ ID NO: 8, a CDRL2 sequence comprising SEQ ID NO: 9, and a CDRL3 sequence comprising SEQ ID NO: 10; and (iii.) a mutation comprising S239C in a heavy chain constant region, wherein the numbering is in accordance with Kabat; and wherein $R^x$ is a sulfhydryl group or a maleimide-sulfhydryl group. In certain embodiments, the anti-PRLR antibody comprises an IgG1 isotype. In certain embodiments, the heavy chain constant region of the anti-PRLR antibody either lacks a C-terminal lysine or comprises an amino acid other than lysine at a C-terminus of the heavy chain constant region. In exemplary embodiments, the anti-PRLR antibody is a humanized antibody.

BRIEF DESCRIPTION OF THE DRAWINGS

FIG. 3B is a graph that shows the comparison of in vivo efficacy of h16f (S239C)-PBD and h16f-MMAE dosed QD7x3 (B) in the BT-474 xenograft model. Mice were dosed with either vehicle only, Ab-095 MMAE (3 mkd (mg/kg/day)), h16f MMAE (3 mkd), Ab-095 PBD (0.3 mkd), h16f PBD (0.3 mkd) or h16f PBD (0.2 mkd). Mean tumor volume was measured in $mm^3$. As shown and described in Example 4, 0.3 mg/kg and 0.2 mg/kg dosing of h16f (S239C)-PBD was superior to 3 mg/kg dosing of h16f-MMAE.

FIG. 4A is a graph that shows in vivo efficacy of h16f (S239C)-PBD in a patient-derived xenograft (PDX) screen with a triple negative breast cancer (TNB) CTG-0012 tumor model. Mice were dosed with either Ab-095 naked antibody, Ab-095 PBD, h16f PBD, Ab-095 MMAE, or h16f MMAE. As shown and described in Example 4, h16f (S239C)-PBD is a more potent ADC conjugate than auristatin-based ADCs and its activity can extend to lower PRLR-expressing tumors.

FIG. 4C is a graph that shows in vivo efficacy of h16f (S239C)-PBD with a TNBC CTG-0869 model. Mice were administered either Ab-095 naked antibody, Ab-095 PBD, h16f PBD, Ab-095 MMAE, or h16f MMAE. Note that for FIG. 4A, FIG. 4B, and FIG. 4C, the term "h16f-PBD" refers to h16f (S239C)-PBD. As shown and described in Example 4, h16f (S239C)-PBD is a more potent ADC conjugate than auristatin-based ADCs and its activity can extend to lower PRLR-expressing tumors.

FIG. 5B is a graph that shows protein aggregation and fragmentation for h16f (S239C)-PBD DAR2. Percent (%) aggregates and % fragments are shown at time "0" (t0) and as percent fragment increase per day and percent aggregate increase per day. As shown and described in Example 5, the in vitro plasma stability of the h16f (S239C) mAb and h16f (S239C)-PBD DAR2 was similar to, if not better than, h16f and h16f-vcMMAE DAR3p.

FIG. 6 provides a table describing the inhibition of in vitro proliferation of BT-474 cells with humanized PRLR ADC candidates. As shown and described in Example 1, among different ADCs containing anti-PRLR antibodies, ADCs utilizing h16f exhibited the most potent inhibitory activity in vitro.

FIG. 7 provides a table describing breast cancer cell line PRLR expression and proliferation assay summary with h16f (S239C)-PBD, h16f-MMAE and control Ab095 ADCs. An exemplary dark pink value is shown with the arrow. Light pink is denoted with a "^". As shown and described in Example 3, the PBD conjugates showed an increase in potency compared to MMAE conjugates of antibody h16f.

FIG. 8 provides a table describing PRLR expression and proliferation assay data with h16f-PBD, h16f-MMAE and control (Ab095) ADCs. An exemplary dark pink value is shown with the arrow. Light pink is denoted with a "^". As shown and described in Example 3, h16f (S239C)-PBD conjugates showed an increase in potency compared to MMAE conjugates of h16f.

DETAILED DESCRIPTION OF THE INVENTION

The present invention relates to antibody-drug conjugates (ADCs) that target prolactin receptor (PRLR) and uses thereof. The ADCs of the present invention possess favorable attributes that provide a distinct advantage over ADCs disclosed in the prior art. For example, the ADCs of the present invention (1) are stable under a variety of conditions (see, e.g. Example 5 infra); (2) are considerably more potent than auristatin-based ADCs using essentially the same antibody backbone (see, e.g. Examples 3-4 infra); (3) display little to no reduced binding affinity to PRLR relative to a parent antibody, unlike similar antibodies also bearing an S239C mutation (see, e.g. Example 6 infra and FIG. 10); and (4) have a surprisingly low drug to antibody ratio (DAR) of about 2, e.g. 1.89, 1.96 (see Example 3 infra). Such ADCs of the present invention contain a pyrrolobenzodiazepine (PBD) warhead that is attached to an anti-PRLR antibody through a linker described in, e.g., Formula (IX) as disclosed herein. Exemplary embodiments include ADCs comprising Formula (X) as disclosed herein. Exemplary anti-PRLR antibodies include, for example, h16f (S239C).

Accordingly, the present invention pertains to antibody drug conjugates (ADCs) comprising a cytotoxic and/or cytostatic agent (e.g., PBD) linked to an anti-prolactin receptor (PRLR) antibody by way of a linker; compositions comprising the ADCs of the invention; methods of making the ADCs of the invention; and methods of using the ADCs to treat cancer associated with abnormal expression of PRLR, e.g. breast cancer.

In certain embodiments, the invention features an ADC comprising the structure of Formula (X)

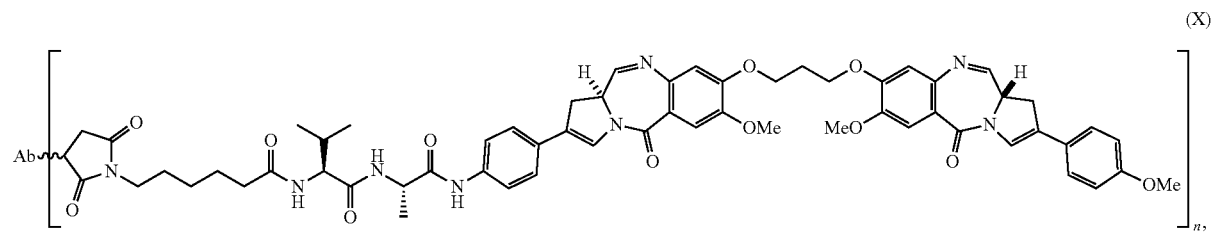

(X)

FIG. 9 provides a table describing human breast cancer PDX models with h16f ADCs. As shown and described in Example 4, h16f (S239C)-PBD is more active than h16f-MMAE in most of the PDX models evaluated.

Figure 10:
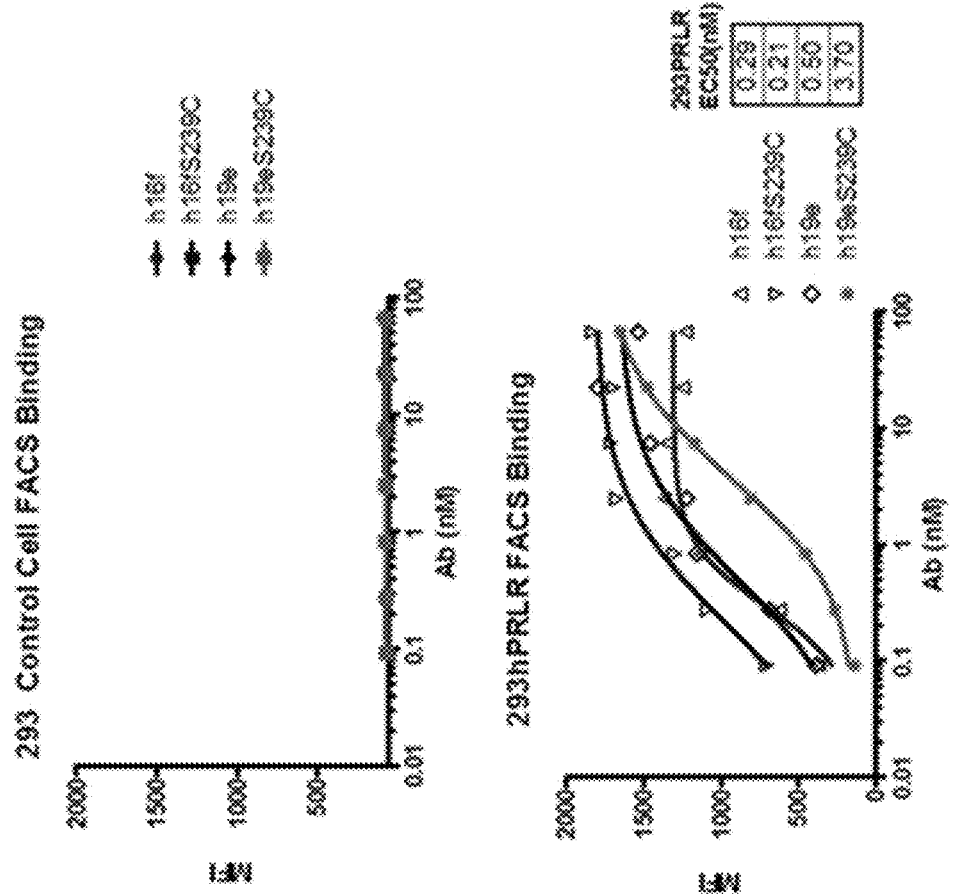

FIG. 10 provides a comparison of specific binding (nM) to control (left) and PRLR-expressing HEK-293 cells (right) between h16f, h16f (S239C) mutant, h19e, and h19e (S239C) mutant. As shown and described in Example 6, the results demonstrate that that the h19e-S239C mutant had a 7-fold decrease in affinity to PRLR compared to h16f-S239C, whereas the h16f-S239C mutant had similar affinity as the parental h16f antibody to PRLR. Calculated EC50 (nM) values are shown on the far righthand side.

or a salt thereof, wherein Ab comprises an anti-PRLR antibody comprising: (i.) a heavy chain variable region comprising a CDRH1 sequence comprising SEQ ID NO: 3, a CDRH2 sequence comprising SEQ ID NO: 4, and a CDRH3 sequence comprising SEQ ID NO: 5; (ii.) a light chain variable region comprising a CDRL1 sequence comprising SEQ ID NO: 8, a CDRL2 sequence comprising SEQ ID NO: 9, and a CDRL3 sequence comprising SEQ ID NO: 10; (iii.) a mutation comprising S239C in a heavy chain constant region, wherein the numbering is in accordance with Kabat; and (iv.) wherein n is 2 or about 2.

In certain embodiments, the invention the invention features an ADC comprising the structure of Formula (X)

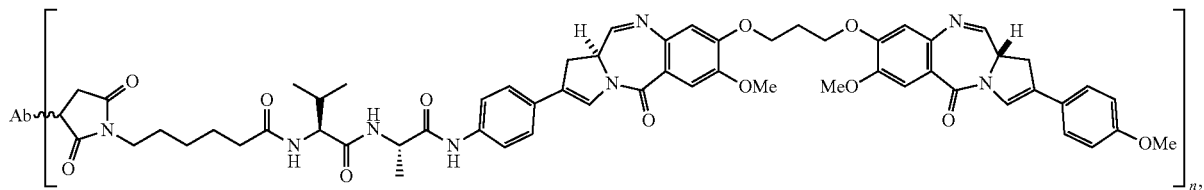

(X)

or a salt thereof, wherein Ab comprises an anti-PRLR antibody comprising: (i.) a heavy chain variable region comprising SEQ ID NO: 2; (ii.) a light chain variable region comprising SEQ ID NO: 7; (iii.) a mutation comprising S239C in a heavy chain constant region, wherein the numbering is in accordance with Kabat; and (iv.) wherein n is 2 or about 2.

In certain embodiments, the invention the invention features an ADC comprising the structure of Formula (X)

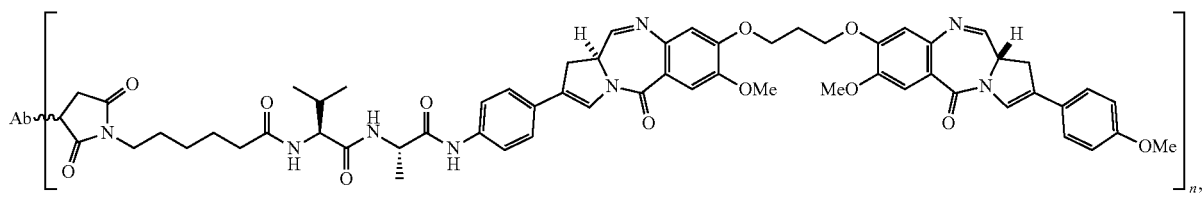

(X)

or a salt thereof, wherein Ab comprises an anti-PRLR antibody comprising a heavy chain comprising SEQ ID NO: 1 and a light chain comprising SEQ ID NO: 6, wherein n is 2 or about 2.

In certain embodiments, the invention features an ADC comprising a cytotoxic and/or cytostatic agent linked to an anti-PRLR antibody by way of a linker, wherein the ADC is a compound according to the structural Formula (I):

[D-L-XY]$_n$Ab    (I), or a salt thereof, wherein D comprises a pyrrolobenzodiazepine (PBD) dimer; L is a linker; Ab is an anti-PRLR antibody comprising a heavy chain comprising SEQ ID NO: 1 and a light chain comprising SEQ ID NO: 6; XY represents a covalent linkage linking linker L to antibody Ab; and n is any integer. In particular, the anti-PRLR ADCs comprising specific linkers and specific cytotoxic and/or cytostatic agents (e.g. a pyrrolobenzodiazepine (PBD) dimer), described herein, exert surprisingly potent anti-tumor activities, in particular when compared to ADCs comprising essentially the same antibody liked to an auristatin. Moreover, the anti-PRLR ADCs of the present invention are characterized by a low drug to antibody ratio (DAR), where low drug loading surprisingly results in a highly efficacious ADC in, for example, treating cancer associated with abnormal levels of PRLR expression. As described in the Examples herein, h16f (S239C)-PBD is a more potent ADC conjugate than an h16f-auristatin ADC, and retains binding specificity to PRLR similar to non-mutated h16f. The present disclosure concerns antibody drug conjugates that specifically bind human PRLR, compositions comprising the ADCs, anti-huPRLR antibodies that can compose the ADCs; polynucleotides encoding anti-huPRLR antibodies that compose the ADCs; host cells capable of producing the antibodies and; methods and compositions useful for making the antibodies; and various methods of using the ADCs.

As will be appreciated by skilled artisans, antibodies are "modular" in nature. Throughout the disclosure, various specific embodiments of the various "modules" comprising the antibodies are described. As specific non-limiting examples, various specific embodiments of variable heavy chain ($V_H$) CDRs, $V_H$ chains, variable light chain ($V_L$) CDRs and $V_L$ chains are described.

The ADCs disclosed herein are also "modular" in nature. Throughout the disclosure, various specific embodiments of the various "modules" comprising the ADCs are described. As specific non-limiting examples, specific embodiments of antibodies, linkers, and cytotoxic and/or cytostatic agents that may compose the ADCs are described.

The ADCs disclosed herein may be in the form of salts, and in some specific embodiments, pharmaceutically acceptable salts. The ADCs of the present invention that possess a sufficiently acidic, sufficiently basic, or both functional groups, can react with any number of acids or bases, organic or inorganic, to form a salt.

Unless otherwise defined herein, scientific and technical terms used in connection with the present disclosure shall have the meanings that are commonly understood by those of ordinary skill in the art.

The terms "human PRLR" and "human PRLR wild type" (abbreviated herein as hPRLR, hPRLRwt), as used herein, refer to a single membrane spanning class 1 cytokine receptor. Human PRLR includes an extracellular region that binds prolactin, a transmembrane region, and a cytoplasmic region. The term human PRLR is intended to include recombinant human PRLR (rhPRLR), which can be prepared by standard recombinant expression methods. Table 1 provides the amino acid sequence of human PRLR (i.e., SEQ ID NO: 12), and the extracellular domain thereof (i.e., SEQ ID NO: 13), which are known in the art. In addition, various isoforms of hPRLR are known in the art and are set forth in Table 1 below.

TABLE 1

Amino acid sequences of human PRLR

| Protein | Sequence Identifier | Sequence |
| --- | --- | --- |
| Human PRLR | SEQ ID NO.: 12 | MKENVASATVFTLLLFLNTCLLNGQLP PGKPEIFKCRSPNKETFTCWWRPGTDG GLPTNYSLTYHREGETLMHECPDYITG GPNSCHFGKQYTSMWRTYIMMVNATNQ MGSSFSDELYVDVTYIVQPDPPLELAV EVKQPEDRKPYLWIKWSPPTLIDLKTG WFTLLYEIRLKPEKAAEWEIHFAGQQT EFKILSLHPGQKYLVQVRCKPDHGYWS AWSPATFIQIPSDFTMNDTTVWISVAV LSAVICLIIVWAVALKGYSMVTCIFPP VPGPKIKGFDAHLLEKGKSEELLSALG CQDFPPTSDYEDLLVEYLEVDDSEDQH LMSVHSKEHPSQGMKPTYLDPDTDSGR GSCDSPSLLSEKCEEPQANPSTFYDPE VIEKPENPETTHTWDPQCISMEGKIPY FHAGGSKCSTWPLPQPSQHNPRSSYHN ITDVCELAVGPAGAPATLLNEAGKDAL KSSQTIKSREEGKATQQREVESFHSET DQDTPWLLPQEKTPFGSAKPLDYVEIH KVNKDGALSLLPKQRENSGKPKKPGTP ENNKEYAKVSGVMDNNILVLVPDPHAK NVACFEESAKEAPPSLEQNQAEKALAN FTATSSKCRLQLGGLDYLDPACFTHSF H (SEQ ID NO: 12) |
| Human PRLR Extracellular Domain | SEQ ID NO: 13 | QLPPGKPEIFKCRSPNKETFTCWWRPG TDGGLPTNYSLTYHREGETLMHECPDY ITGGPNSCHFGKQYTSMWRTYIMMVNA TNQMGSSFSDELYVDVTYIVQPDPPLE LAVEVKQPEDRKPYLWIKWSPPTLIDL KTGWFTLLYEIRLKPEKAAEWEIHFAG QQTEFKILSLHPGQKYLVQVRCKPDHG YWSAWSPATFIQIPSDFTMN (SEQ ID NO: 13) |
| Human PRLR Isoform 2 | SEQ ID NO: 14 | MKENVASATVFTLLLFLNTCLLNVQPD PPLELAVEVKQPEDRKPYLWIKWSPPT LIDLKTGWFTLLYEIRLKPEKAAEWEI HFAGQQTEFKILSLHPGQKYLVQVRCK PDHGYWSAWSPATFIQIPSDFTMNDTT VWISVAVLSAVICLIIVWAVALKGYSM VTCIFPPVPGPKIKGFDAHLLEKGKSE ELLSALGCQDFPPTSDYEDLLVEYLEV DDSEDQHLMSVHSKEHPSQGMKPTYLD PDTDSGRGSCDSPSLLSEKCEEPQANP STFYDPEVIEKPENPETTHTWDPQCIS MEGKIPYFHAGGSKCSTWPLPQPSQHN PRSSYHNITDVCELAVGPAGAPATLLN EAGKDALKSSQTIKSREEGKATQQREV ESFHSETDQDTPWLLPQEKTPFGSAKP LDYVEIHKVNKDGALSLLPKQRENSGK PKKPGTPENNKEYAKVSGVMDNNILVL VPDPHAKNVACFEESAKEAPPSLEQNQ AEKALANFTATSSKCRLQLGGLDYLDP ACFTHSFH (SEQ ID NO: 14) |
| Human PRLR Isoform 3 | SEQ ID NO: 15 | MKENVASATVFTLLLFLNTCLLNGQLP PGKPEIFKCRSPNKETFTCWWRPGTDG GLPTNYSLTYHREGETLMHECPDYITG GPNSCHFGKQYTSMWRTYIMMVNATNQ MGSSFSDELYVDVTYIVQPDPPLELAV EVKQPEDRKPYLWIKWSPPTLIDLKTG WFTLLYEIRLKPEKAAEWEIHFAGQQT EFKILSLHPGQKYLVQVRCKPDHGYWS AWSPATFIQIPSAW (SEQ ID NO: 15) |
| Human PRLR Isoform 4 | SEQ ID NO: 16 | MKENVASATVFTLLLFLNTCLLNGQLP PGKPEIFKCRSPNKETFTCWWRPGTDG GLPTNYSLTYHREGETLMHECPDYITG GPNSCHFGKQYTSMWRTYIMMVNATNQ MGSSFSDELYVDVTYIVQPDPPLELAV EVKQPEDRKPYLWIKWSPPTLIDLKTG WFTLLYEIRLKPEKAAEWEIHFAGQQT EFKILSLHPGQKYLVQVRCKPDHGYWS AWSPATFIQIPSDFTMNDTTVWISVAV |

TABLE 1-continued

Amino acid sequences of human PRLR

| Protein | Sequence Identifier | Sequence |
|---|---|---|
| | | LSAVICLIIVWAVALKGYSMVTCIFPP<br>VPGPKIKGFDAHLLEKGKSEELLSALG<br>CQDFPPTSDYEDLLVEYLEVDDSEDQH<br>LMSVHSKEHPSQGDPLMLGASHYKNLK<br>SYRPRKISSQGRLAVFTKATLTTVQ<br>(SEQ ID NO: 16) |
| Human PRLR Isoform 5 | SEQ ID NO: 17 | MKENVASATVFTLLLFLNTCLLNGQLP<br>PGKPEIFKCRSPNKETFTCWWRPGTDG<br>GLPTNYSLTYHREGETLMHECPDYITG<br>GPNSCHFGKQYTSMWRTYIMMVNATNQ<br>MGSSFSDELYVDVTYIVQPDPPLELAV<br>EVKQPEDRKPYLWIKWSPPTLIDLKTG<br>WFTLLYEIRLKPEKAAEWEIHFAGQQT<br>EFKILSLHPGQKYLVQVRCKPDHGYWS<br>AWSPATFIQIPSDFTMNDTTVWISVAV<br>LSAVICLIIVWAVALKGYSMVTCIFPP<br>VPGPKIKGFDAHLLEKGKSEELLSALG<br>CQDFPPTSDYEDLLVEYLEVDDSEDQH<br>LMSVHSKEHPSQEREQRQAQEARDS<br>(SEQ ID NO: 17) |
| Human PRLR Isoform 6 | SEQ ID NO: 18 | MKENVASATVFTLLLFLNTCLLNGQLP<br>PGKPEIFKCRSPNKETFTCWWRPGTDG<br>GLPTNYSLTYHREGETLMHECPDYITG<br>GPNSCHFGKQYTSMWRTYIMMVNATNQ<br>MGSSFSDELYVDVTYIVQPDPPLELAV<br>EVKQPEDRKPYLWIKWSPPTLIDLKTG<br>WFTLLYEIRLKPEKAAEWEIHFAGQQT<br>EFKILSLHPGQKYLVQVRCKPDHGYWS<br>AWSPATFIQIPSDFTMNDTTVWISVAV<br>LSAVICLIIVWAVALKGYSMVTCIFPP<br>VPGPKIKGFDAHLLEVTP (SEQ ID NO: 18) |
| Human PRLR Isoform 7 | SEQ ID NO: 19 | MKENVASATVFTLLLFLNTCLLNGQLP<br>PGKPEIFKCRSPNKETFTCWWRPGTDG<br>GLPTNYSLTYHREGETLMHECPDYITG<br>GPNSCHFGKQYTSMWRTYIMMVNATNQ<br>MGSSFSDELYVDVTYIVQPDPPLELAV<br>EVKQPEDRKPYLWIKWSPPTLIDLKTG<br>WFTLLYEIRLKPEKAAEWEIHFAGQQT<br>EFKILSLHPGQKYLVQVRCKPDHGYWS<br>AWSPATFIQIPSGDPLMLGASHYKNLK<br>SYRPRKISSQGRLAVFTKATLTTVQ<br>(SEQ ID NO: 19) |
| Human PRLR Isoform 8 | SEQ ID NO: 20 | MHECPDYITGGPNSCHFGKQYTSMWRT<br>YIMMVNATNQMGSSFSDELYVDVTYIV<br>QPDPPLELAVEVKQPEDRKPYLWIKWS<br>PPTLIDLKTGWFTLLYEIRLKPEKAAE<br>WEIHFAGQQTEFKILSLHPGQKYLVQV<br>RCKPDHGYWSAWSPATFIQIPSDFTMN<br>DTTVWISVAVLSAVICLIIVWAVALKG<br>YSMVTCIFPPVPGPKIKGFDAHLLEVT<br>P (SEQ ID NO: 20) |

As used herein, the term "antibody" (Ab) refers to an immunoglobulin molecule that specifically binds to, or is immunologically reactive with, a particular antigen, i.e., hPRLR. Antibodies comprise complementarity determining regions (CDRs), also known as hypervariable regions, in both the light chain and heavy chain variable domains. The more highly conserved portions of the variable domains are called the framework (FR). As is known in the art, the amino acid position/boundary delineating a hypervariable region of an antibody can vary, depending on the context and the various definitions known in the art. Some positions within a variable domain may be viewed as hybrid hypervariable positions in that these positions can be deemed to be within a hypervariable region under one set of criteria, while being deemed to be outside a hypervariable region under a different set of criteria. One or more of these positions can also be found in extended hypervariable regions. The variable domains of native heavy and light chains each comprise four FR regions, largely by adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen binding site of antibodies. See Kabat et al., Sequences of Proteins of Immunological Interest (National Institute of Health, Bethesda, Md. 1987). As used herein, numbering of immunoglobulin amino acid residues is done according to the immunoglobulin amino acid residue numbering system of Kabat et al. unless otherwise indicated.

The term "monoclonal antibody" as used herein is not limited to antibodies produced through hybridoma technology. A monoclonal antibody is derived from a single clone, including any eukaryotic, prokaryotic, or phage clone, by any means available or known in the art. Monoclonal antibodies useful with the present disclosure can be prepared using a wide variety of techniques known in the art including the use of hybridoma, recombinant, and phage display technologies, or a combination thereof. In many uses of the present disclosure, including in vivo use of ADCs including anti-huPRLR antibodies in humans, chimeric, primatized, humanized, or human antibodies can suitably be used. In exemplary embodiments, the anti-huPRLR antibodies of the present invention are humanized, e.g. h16f (S239C).

"Humanized" forms of non-human (e.g., murine) antibodies are chimeric immunoglobulins that contain minimal sequences derived from non-human immunoglobulin. In general, a humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. An exemplary humanized antibody of the present invention is h16f (S239C). The humanized antibody can also comprise at least a portion of an immunoglobulin constant region (Fc), typically that of a human immunoglobulin consensus sequence. Methods of antibody humanization are known in the art.

Anti-hPRLR ADCs of the invention may comprise full-length (intact) antibody molecules that are capable of specifically binding huPRLR In one embodiment, the ADC of the invention comprises a full-length h16f (S239C) antibody.

The term "cytotoxic and/or cytostatic agent", as used herein, is meant to refer to any agent or drug known to inhibit the growth and/or replication of, and/or kill cells. In one embodiment, the cytotoxic and/or cytostatic agent is a cell-permeating DNA minor groove-binding agent such as a pyrrolobenzodiazepine ("PBD") and PBD dimers.

The term "antibody-drug-conjugate" or "ADC" refers to an antibody chemically linked to one or more cytotoxic and/or cytostatic agents. In one embodiment, an ADC includes an antibody, cytotoxic and/or cytostatic agent, and a linker that enables attachment or conjugation of the drug to the antibody. An ADC of the present invention typically has anywhere from 1 to 3 cytotoxic and/or cytostatic agents conjugated to the antibody, including a drug loaded species of 1, 2, or 3.

The term "drug-to-antibody ratio" or "DAR" refers to the number of drugs (cytotoxic and/or cytostatic agents), e.g., PBD, attached to the antibody of the ADC. The DAR of an ADC can range from 1 to 3, although higher loads are also possible depending on the number of linkage site on an antibody. The term DAR may be used in reference to the number of drugs loaded onto an individual antibody, or, alternatively, may be used in reference to the average or mean DAR of a group of ADCs. In one embodiment, the ADC of the invention has a DAR of about 2. In this context, the term "about", means an amount within ±7.5% of the actual value. i.e. "about 2" means 1.85, 1.86, 1.87, 1.88, 1.89, 1.90, 1.91, 1.92, 1.93, 1.94, 1.95, 1.96, 1.97, 1.98, 1.99, 2.00, 2.01, 2.02, 2.03, 2.04, 2.05, 2.06, 2.07, 2.08, 2.09, 2.10, 2.11, 2.12, 2.13, 2.14, 2.15, and any intervening ranges.

In specific exemplary embodiments, the ADCs of the invention comprise an anti-PRLR antibody, e.g., an h16f (S239C) anti-PRLR antibody having a DAR of about 2.

In one aspect, the ADCs of the invention comprise an anti-PRLR antibody comprising a heavy chain variable region comprising a CDR set (CDRH1, CDRH2, and CDRH3) as set forth in SEQ ID NOS: 3, 4, and 5, and a light chain variable region comprising a CDR set as set forth in SEQ ID NOS: 8, 9, and 10 (CDRL1, CDRL2, and CDRL3). Preferably, the anti-PRLR antibody is an IgG1 isotype having a heavy chain constant region with a cysteine mutation engineered to provide a conjugation site for a PBD. In one embodiment, the cysteine mutation is at position 239 of the heavy chain. Preferably, the mutation is S239C, numbered according to Kabat. The anti-PRLR antibody "h16f (S239C)" as described herein has a heavy chain variable region comprising CDRH1, CDRH2, and CDRH3 as set forth in SEQ ID NOS: 3, 4, and 5 respectively, and a light chain variable region comprising CDRL1, CDRL2, and CDRL3 as set forth in SEQ ID NOS: 8, 9, and 10 respectively. In some embodiments, the anti-PRLR antibody either lacks a C-terminal lysine or comprises an amino acid other than lysine at a C-terminus of the heavy chain constant region.

In another aspect, the ADCs of the invention comprise an anti-PRLR antibody comprising a heavy chain variable region comprising SEQ ID NO: 2, and a light chain variable region comprising SEQ ID NO: 7. Preferably, the anti-PRLR antibody is an IgG1 isotype having a heavy chain constant region with a cysteine mutation engineered to provide a conjugation site for a PBD. In one embodiment, the cysteine mutation is at position 239 of the heavy chain. Preferably, the mutation is S239C, numbered according to Kabat. The anti-PRLR antibody "h16f (S239C)" as described herein has a heavy chain variable region comprising SEQ ID NO: 2, and a light chain variable region comprising SEQ ID NO: 7. In some embodiments, the anti-PRLR antibody either lacks a C-terminal lysine or comprises an amino acid other than lysine at a C-terminus of the heavy chain constant region.

In another aspect, the ADCs of the invention comprise an anti-PRLR antibody comprising a heavy chain comprising SEQ ID NO: 1, and a light chain comprising SEQ ID NO: 6. The anti-PRLR antibody "h16f (S239C)" as described herein has a heavy chain comprising the amino acid sequence set forth in SEQ ID NO: 1 and a light chain comprising the amino acid sequence set forth in SEQ ID NO: 6. SEQ ID NO: 1 differs from SEQ ID NO: 11 only in that SEQ ID NO: 1 contains the S239C mutation; see Table 9 infra. As described herein, the S239C mutation corresponds to amino acid residue number 242 of SEQ ID NO: 1. In some embodiments, the anti-PRLR antibody either lacks a C-terminal lysine or comprises an amino acid other than lysine at a C-terminus of the heavy chain constant region.

Antibodies of the anti-PRLR ADCs described herein may be antibodies whose sequences have been modified to alter at least one constant region-mediated biological effector function. For example, in some embodiments, an anti-PRLR antibody may be modified to reduce at least one constant region-mediated biological effector function relative to the unmodified antibody, e.g., reduced binding to the Fc receptor (FcγR). FcγR binding may be reduced by mutating the immunoglobulin constant region segment of the antibody at particular regions necessary for FcγR interactions (See, e.g., Canfield and Morrison, 1991, J. Exp. Med. 173:1483-1491; and Lund et al., 1991, J. Immunol. 147:2657-2662). Reducing FcγR binding may also reduce other effector functions which rely on FcγR interactions, such as opsonization, phagocytosis and antigen-dependent cellular cytotoxicity ("ADCC").

Antibodies included in anti-PRLR ADCs may have low levels of, or lack, fucose. Antibodies lacking fucose have been correlated with enhanced ADCC activity, especially at low doses of antibody. See Shields et al., 2002, J. Biol. Chem. 277:26733-26740; Shinkawa et al., 2003, J. Biol. Chem. 278:3466-73. Methods of preparing fucose-less antibodies include growth in rat myeloma YB2/0 cells (ATCC CRL 1662). YB2/0 cells express low levels of FUT8 mRNA, which encodes α-1,6-fucosyltransferase, an enzyme necessary for fucosylation of polypeptides.

Antibodies included in anti-PRLR ADCs may include modifications that increase or decrease their binding affinities to the neonatal Fc receptor, FcRn, for example, by mutating the immunoglobulin constant region segment at particular regions involved in FcRn interactions (see, e.g., WO 2005/123780). An anti-PRLR antibody may have one or more amino acids inserted into one or more of its hypervariable regions, for example as described in Jung & Plückthun, 1997, Protein Engineering 10:9, 959-966; Yazaki et al., 2004, Protein Eng. Des Sel. 17(5):481-9; and U.S. Pat. App. No. 2007/0280931.

Antibodies may be produced by any of a number of techniques, as described for example in International Publication No. WO2014/105810, incorporated by reference in its entirety herein.

Anti-PRLR antibodies with high affinity for PRLR, e.g., human PRLR, may be desirable for therapeutic uses. Accordingly, the present disclosure contemplates ADCs comprising anti-PRLR antibodies having a high binding affinity to PRLR, and in particular human PRLR. In specific embodiments, the antibodies bind PRLR with an affinity of at least about 100 nM, but may exhibit higher affinity, for example, at least about 90 nM, 80 nM, 70 nM, 60 nM, 50 nM, 40 nM, 30 nM, 25 nM, 20 nM, 15 nM, 10 nM, 7 nM, 6 nM, 5 nM, 4 nM, 3 nM, 2 nM, 1 nM, 0.1 nM, 0.01 nM, or even higher. In some embodiments, the antibodies bind PRLR with an affinity in the range of about 1 pM to about 100 nM, or an affinity ranging between any of the foregoing values.

Affinity of antibodies for PRLR can be determined using techniques well known in the art or described herein, such as for example, but not by way of limitation, ELISA, isothermal titration calorimetry (ITC), surface plasmon resonance, flow cytometry or fluorescent polarization assays.

Anti-PRLR antibodies can be prepared by recombinant expression of immunoglobulin light and heavy chain genes in a host cell using standard recombinant DNA methodologies known in the art, such as those described in Molecular Cloning; A Laboratory Manual, Second Edition (Sambrook, Fritsch and Maniatis (eds), Cold Spring Harbor, N.Y., 1989). For example, DNAs encoding partial or full-length light and heavy chains are inserted into expression vectors such that the genes are operatively linked to transcriptional and translational control sequences and transformed into a host cell. The antibody light chain gene and the antibody heavy chain gene can be inserted into separate vectors or, more typically, both genes are inserted into the same expression vector, accomplished by methods known in the art. Antibodies can also be produced by chemical synthesis (e.g., by the methods described in Solid Phase Peptide Synthesis, 2$^{nd}$ ed., 1984 The Pierce Chemical Co., Rockford, Ill.).

Anti-PRLR ADCs of the invention generally comprise an anti-PRLR antibody (e.g., h16f(S239C)) having one or more cytotoxic and/or cytostatic agents, which may be the same or different, linked thereto by way of one or more linkers, which may also be the same or different. In specific embodiments, the anti-PRLR ADCs are compounds according to structural formula (I):

[D-L-XY]$_n$-Ab (I)

or salts thereof, where each "D" represents, independently of the others, a cytotoxic and/or cytostatic agent ("drug", e.g. PBD dimer); each "L" represents, independently of the others, a linker; "Ab" represents an anti-PRLR antibody; each "XY" represents a linkage formed between a functional group $R^x$ on the linker and a "complementary" functional group $R^y$ on the antigen binding moiety; and n represents the number of drugs linked to Ab, or the drug-to-antibody ratio (DAR), of the ADC. Specific embodiments of various anti-PRLR antibodies that may compose ADCs according to structural formula (I) are described above.

In some specific embodiments of the ADCs or salts of structural formula (I), each D is the same and/or each L is the same.

Specific embodiments of cytotoxic and/or cytostatic agents (D) and linkers (L) that may compose the anti-PRLR ADCs, as well as the number of cytotoxic and/or cytostatic agents linked to the anti-PRLR ADCs, are described in more detail below.

In certain embodiments, the ADC has the structure of Formula (I), or a salt thereof, wherein D comprises a pyrrolobenzodiazepine (PBD) dimer; L is a linker; Ab is an antibody comprising SEQ ID NO: 1; XY represents a covalent linkage linking linker L to antibody Ab; and n is any integer. The DAR of an ADC is equivalent to the "n" referred to in Formula I. In one embodiment, n is 2 or 4. In preferred embodiments, n is about 2. In this context, the term "about", means an amount within ±7.5% of the actual value. i.e. "about 2" means 1.85, 1.86, 1.87, 1.88, 1.89, 1.90, 1.91, 1.92, 1.93, 1.94, 1.95, 1.96, 1.97, 1.98, 1.99, 2.00, 2.01, 2.02, 2.03, 2.04, 2.05, 2.06, 2.07, 2.08, 2.09, 2.10, 2.11, 2.12, 2.13, 2.14, 2.15, and any intervening ranges. In exemplary embodiments, n is about 1.89 or about 1.96. Additional details regarding drugs (D of Formula I) and linkers (L of Formula I) that may be used in the ADCs of the invention, as well as alternative ADC structures, are described below. In one embodiment, the cytotoxic and/or cytostatic agent is a pyrrolobenzodiazepine (PBD), e.g., a PBD dimer.

The structures of PBDs can be found, for example, in U.S. Patent Application Pub. Nos. 2013/0028917 and 2013/0028919, and in WO 2011/130598 A1, each of which are incorporated herein by reference in their entirety. The generic structure of a PBD is provided below as Formula (II).

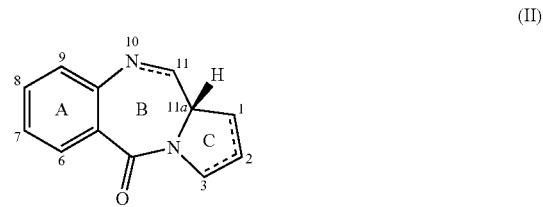

(II)

PBDs differ in the number, type and position of substituents, in both their aromatic A rings and pyrrolo C rings, and in the degree of saturation of the C ring. In the B-ring, there is generally an imine (N=C), a carbinolamine (NH—CH(OH)), or a carbinolamine methyl ether (NH—CH(OMe)) at the N10-C11 position which is the electrophilic centre responsible for alkylating DNA. All of the known natural products have an (S)-configuration at the chiral C11a position that provides a right-handed twist when viewed from the C ring towards the A ring. The PBD examples provided herein may be conjugated to the anti-PRLR antibodies of the invention. Further examples of PBDs that may be conjugated to the anti-PRLR antibodies of the invention can be found, for example, in U.S. Patent Application Publication Nos. 2013/0028917 A1 and 2013/0028919 A1, in U.S. Pat. No. 7,741,319 B2, and in WO 2011/130598 A1 and WO 2006/111759 A1, each of which are incorporated herein by reference in their entirety.

In the anti-huPRLR ADCs described herein, the cytotoxic and/or cytostatic agents are linked to the antibody by way of linkers. The linkers may be short, long, hydrophobic, hydrophilic, flexible or rigid, or may be composed of segments that each independently have one or more of the abovementioned properties such that the linker may include segments having different properties. The linkers may be polyvalent such that they covalently link more than one agent to a single site on the antibody, or monovalent such that covalently they link a single agent to a single site on the antibody.

In certain embodiments, the linker selected is cleavable in vivo. Cleavable linkers may include chemically or enzymatically unstable or degradable linkages. Cleavable linkers generally rely on processes inside the cell to liberate the drug, such as reduction in the cytoplasm, exposure to acidic conditions in the lysosome, or cleavage by specific proteases or other enzymes within the cell. Cleavable linkers generally incorporate one or more chemical bonds that are either chemically or enzymatically cleavable while the remainder of the linker is noncleavable. In certain embodiments, a linker comprises a chemically labile group such as hydrazone and/or disulfide groups. Linkers comprising chemically labile groups exploit differential properties between the plasma and some cytoplasmic compartments. The intracellular conditions to facilitate drug release for hydrazone containing linkers are the acidic environment of endosomes and lysosomes, while the disulfide containing linkers are reduced in the cytosol, which contains high thiol concentrations, e.g., glutathione. In certain embodiments, the plasma stability of a linker comprising a chemically labile group may be increased by introducing steric hindrance using substituents near the chemically labile group.

Acid-labile groups, such as hydrazone, remain intact during systemic circulation in the blood's neutral pH environment (pH 7.3-7.5) and undergo hydrolysis and release the drug once the ADC is internalized into mildly acidic endosomal (pH 5.0-6.5) and lysosomal (pH 4.5-5.0) compartments of the cell. This pH dependent release mechanism has been associated with nonspecific release of the drug. To increase the stability of the hydrazone group of the linker, the linker may be varied by chemical modification, e.g., substitution, allowing tuning to achieve more efficient release in the lysosome with a minimized loss in circulation.

Hydrazone-containing linkers may contain additional cleavage sites, such as additional acid-labile cleavage sites and/or enzymatically labile cleavage sites. ADCs including exemplary hydrazone-containing linkers include the following structures of Formulas (III), (IV), and (V):

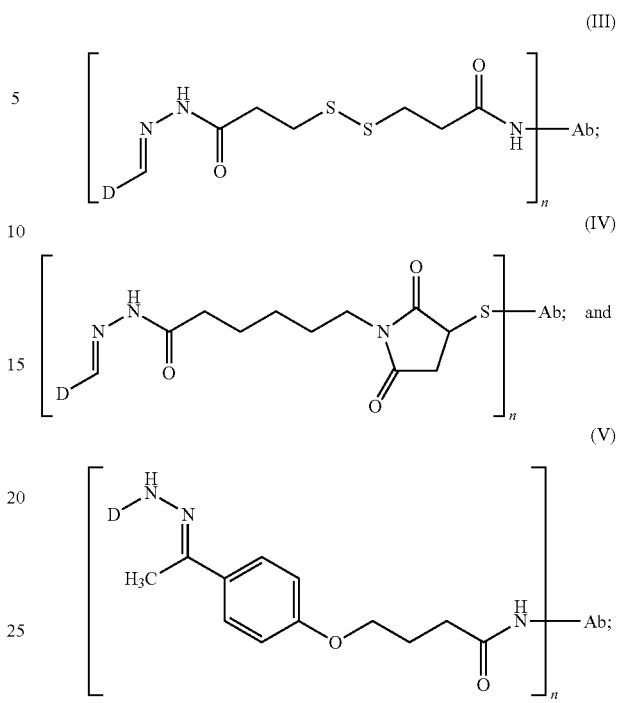

or a salt thereof, wherein D and Ab represent the cytotoxic and/or cytostatic agent (drug) and antibody, respectively, and n represents the number of drug-linkers linked to the antibody. In certain linkers such as that of (Formula (III)), the linker comprises two cleavable groups—a disulfide and a hydrazone moiety. For such linkers, effective release of the unmodified free drug requires acidic pH or disulfide reduction and acidic pH. Linkers such as those of Formula (IV) and (V) have been shown to be effective with a single hydrazone cleavage site.

Other acid-labile groups that may be included in linkers include cis-aconityl-containing linkers. cis-Aconityl chemistry uses a carboxylic acid juxtaposed to an amide bond to accelerate amide hydrolysis under acidic conditions.

Cleavable linkers may also include a disulfide group. Disulfides are thermodynamically stable at physiological pH and are designed to release the drug upon internalization inside cells, wherein the cytosol provides a significantly more reducing environment compared to the extracellular environment. Scission of disulfide bonds generally requires the presence of a cytoplasmic thiol cofactor, such as (reduced) glutathione (GSH), such that disulfide-containing linkers are reasonably stable in circulation, selectively releasing the drug in the cytosol. The intracellular enzyme protein disulfide isomerase, or similar enzymes capable of cleaving disulfide bonds, may also contribute to the preferential cleavage of disulfide bonds inside cells. GSH is reported to be present in cells in the concentration range of 0.5-10 mM compared with a significantly lower concentration of GSH or cysteine, the most abundant low-molecular weight thiol, in circulation at approximately 5 µM. Tumor cells, where irregular blood flow leads to a hypoxic state, result in enhanced activity of reductive enzymes and therefore even higher glutathione concentrations. In certain embodiments, the in vivo stability of a disulfide-containing linker may be enhanced by chemical modification of the linker, e.g., use of steric hinderance adjacent to the disulfide bond.

ADCs including exemplary disulfide-containing linkers include the following structures of Formulas (VI), (VII), and (VIII):

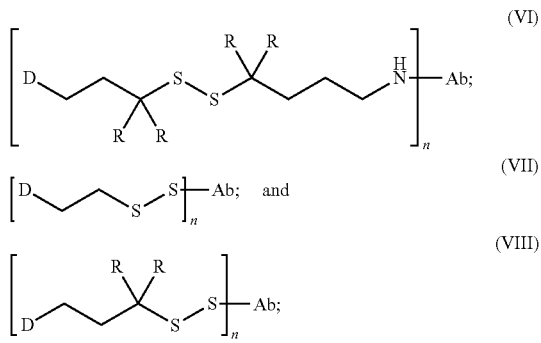

or a salt thereof, wherein D and Ab represent the drug and antibody, respectively, n represents the number of drug-linkers linked to the antibody, and R is independently selected at each occurrence from hydrogen or alkyl, for example. In certain embodiments, increasing steric hinderance adjacent to the disulfide bond increases the stability of the linker. Structures such as (VI) and (VIII) show increased in vivo stability when one or more R groups is selected from a lower alkyl such as methyl.

Another type of cleavable linker that may be used is a linker that is specifically cleaved by an enzyme. Such linkers are typically peptide-based or include peptidic regions that act as substrates for enzymes. Peptide based linkers tend to be more stable in plasma and extracellular milieu than chemically labile linkers. Peptide bonds generally have good serum stability, as lysosomal proteolytic enzymes have very low activity in blood due to endogenous inhibitors and the unfavorably high pH value of blood compared to lysosomes. Release of a drug from an antibody occurs specifically due to the action of lysosomal proteases, e.g., cathepsin and plasmin. These proteases may be present at elevated levels in certain tumor cells.

In exemplary embodiments, the cleavable peptide is selected from tetrapeptides such as Gly-Phe-Leu-Gly, Ala-Leu-Ala-Leu, or dipeptides such as Val-Cit, Val-Ala, Met-(D)Lys, Asn-(D)Lys, Val-(D)Asp, Phe-Lys, Ile-Val, Asp-Val, His-Val, NorVal-(D)Asp, Ala-(D)Asp, Met-Lys, Asn-Lys, Ile-Pro, Me3Lys-Pro, PhenylGly-(D)Lys, Met-(D)Lys, Asn-(D)Lys, Pro-(D)Lys, Met-(D)Lys, Asn-(D)Lys, Met-(D)Lys, Asn-(D)Lys. In certain embodiments, dipeptides are preferred over longer polypeptides due to hydrophobicity of the longer peptides.

A variety of dipeptide-based cleavable linkers useful for linking drugs such as doxorubicin, mitomycin, campotothecin, tallysomycin and auristatin/auristatin family members to antibodies have been described (see, Dubowchik et al., 1998, *J Org. Chem.* 67:1866-1872; Dubowchik et al., 1998, *Bioorg. Med. Chem. Lett.* 8(21):3341-3346; Walker et al., 2002, *Bioorg. Med. Chem. Lett.* 12:217-219; Walker et al., 2004, *Bioorg. Med. Chem. Lett.* 14:4323-4327; and Francisco et al., 2003, *Blood* 102:1458-1465, Dornina et al., 2008, Bioconjugate Chemistry 19:1960-1963, of each of which is incorporated herein by reference). All of these dipeptide linkers, or modified versions of these dipeptide linkers, may be used in the ADCs described herein. Other dipeptide linkers that may be used include those found in ADCs such as Seattle Genetics' Brentuximab Vendotin SGN-35 (Adcetris™), Seattle Genetics SGN-75 (anti-CD-70, Val-Cit-MMAF), Celldex Therapeutics glembatumumab (CDX-011) (anti-NMB, Val-Cit-MMAE), and Cytogen PSMA-ADC (PSMA-ADC-1301) (anti-PSMA, Val-Cit-MMAE).

Enzymatically cleavable linkers may include a self-immolative spacer to spatially separate the drug from the site of enzymatic cleavage. The direct attachment of a drug to a peptide linker can result in proteolytic release of an amino acid adduct of the drug, thereby impairing its activity. The use of a self-immolative spacer allows for the elimination of the fully active, chemically unmodified drug upon amide bond hydrolysis.

One self-immolative spacer is the bifunctional para-aminobenzyl alcohol group, which is linked to the peptide through the amino group, forming an amide bond, while amine containing drugs may be attached through carbamate functionalities to the benzylic hydroxyl group of the linker (PABC). The resulting prodrugs are activated upon protease-mediated cleavage, leading to a 1,6-elimination reaction releasing the unmodified drug, carbon dioxide, and remnants of the linker group. The following scheme depicts the fragmentation of p-aminobenzyl ether and release of the drug:

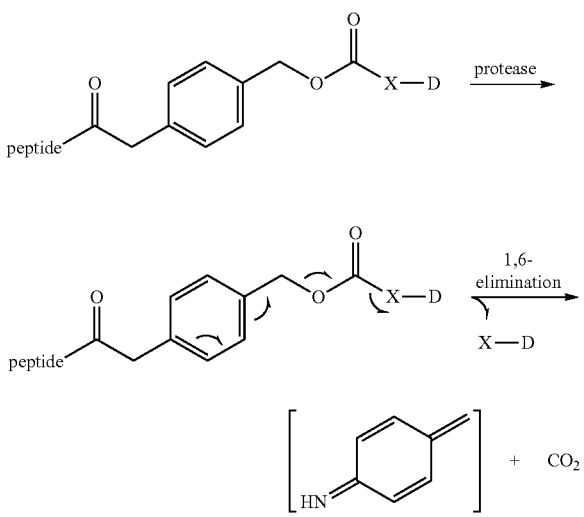

wherein X-D represents the unmodified drug.

Heterocyclic variants of this self-immolative group have also been described. See for example, U.S. Pat. No. 7,989,434, incorporated herein by reference.

In some embodiments, the enzymatically cleavable linker is a ß-glucuronic acid-based linker. Facile release of the drug may be realized through cleavage of the ß-glucuronide glycosidic bond by the lysosomal enzyme ß-glucuronidase. This enzyme is present abundantly within lysosomes and is overexpressed in some tumor types, while the enzyme activity outside cells is low. ß-Glucuronic acid-based linkers may be used to circumvent the tendency of an ADC to undergo aggregation due to the hydrophilic nature of ß-glucuronides. In some embodiments, ß-glucuronic acid-based linkers are preferred as linkers for ADCs linked to hydrophobic drugs. The following scheme depicts the release of the drug from and ADC containing a ß-glucuronic acid-based linker:

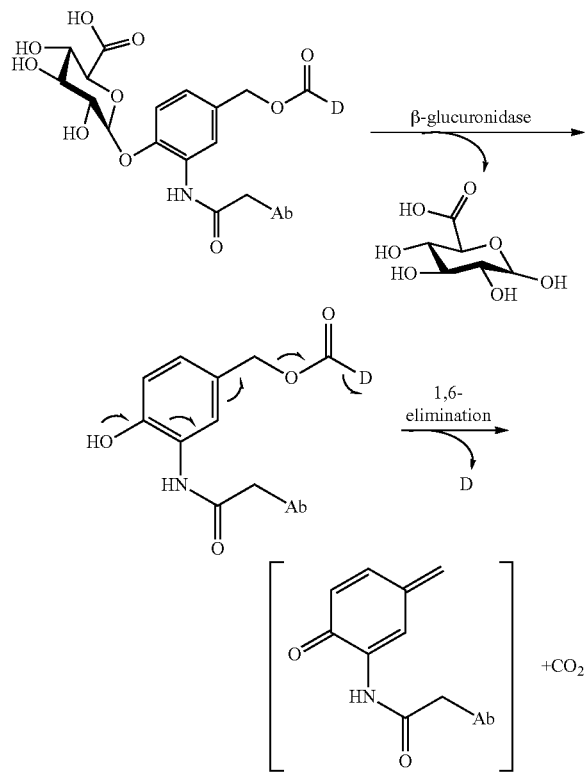

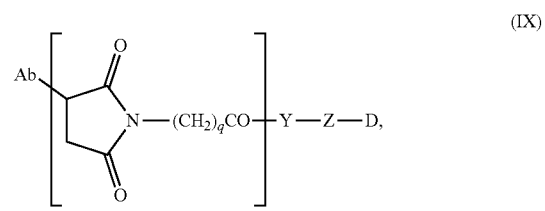

or a salt thereof. In exemplary embodiments, q is 5.

In one aspect, the present invention describes an ADC comprising a cytotoxic and/or cytostatic agent linked to an antibody by way of a linker, wherein the antibody drug conjugate is a compound according to the structural Formula (I), or a salt thereof, wherein D comprises a pyrrolobenzodiazepine (PBD) dimer; L is a linker; Ab is an antibody comprising SEQ ID NO: 1; XY represents a covalent linkage linking linker L to antibody Ab; and n is any integer. In one embodiment, XY represents a covalent linkage linking linker L to antibody Ab, where the XY is a linkage formed with a sulfhydryl group on antibody Ab. In another embodiment, XY is a maleimide-sulfhydryl linkage.

In certain embodiments, the ADC of the present invention comprises the structure of Formula (X):

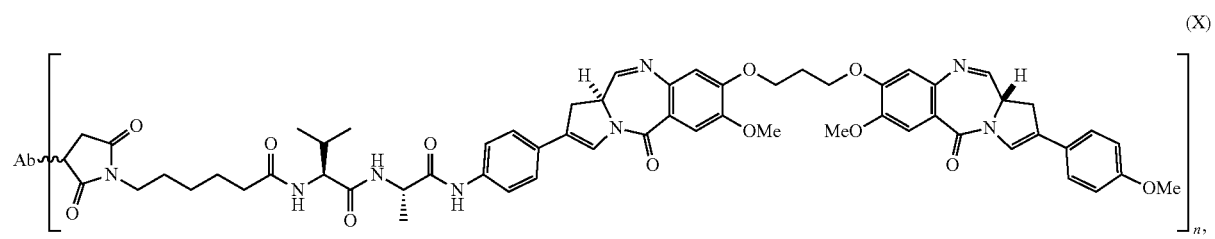

A variety of cleavable ß-glucuronic acid-based linkers useful for linking drugs such as auristatins, camptothecin and doxorubicin analogues, CBI minor-groove binders, and psymberin to antibodies have been described (see, e.g. Nolting, Chapter 5 "Linker Technology in Antibody-Drug Conjugates," In: *Antibody-Drug Conjugates: Methods in Molecular Biology*, vol. 1045, pp. 71-100, Laurent Ducry (Ed.), Springer Science & Business Medica, LLC, 2013; Jeffrey et al., 2006, *Bioconjug. Chem.* 17:831-840; Jeffrey et al., 2007, *Bioorg. Med. Chem. Lett.* 17:2278-2280; and Jiang et al., 2005, *J. Am. Chem. Soc.* 127:11254-11255, each of which is incorporated herein by reference). All of these ß-glucuronic acid-based linkers may be used in the anti-PRLR ADCs described herein.

In a one embodiment, the linker used in the ADCs of the invention is shown in Formula (IX), wherein Y is Val, Z is Ala, D is the drug (e.g. PBD dimer), and q is 1, 2, 3, 4, 5, 6, 7, or 8:

or a salt thereof, wherein Ab is an antibody comprising a heavy chain variable region comprising a CDR set (CDRH1, CDRH2, and CDRH3) as set forth in SEQ ID NOS: 3, 4, and 5 respectively, and a light chain variable region comprising a CDR set (CDRL1, CDRL2, and CDRL3) as set forth in SEQ ID NOS: 8, 9, and 10 respectively, and n is about 2 to about 4. Preferably, the anti-PRLR antibody is an IgG1 isotype having a constant region with cysteine mutation engineered to provide a conjugation site for a PBD. In one embodiment, the cysteine mutation is at position 239 of the heavy chain. Preferably, the mutation is S239C, wherein the numbering is in accordance with Kabat. In one embodiment, n is about 2 or about 4. In a preferred embodiment, n is about 2. In one embodiment, the heavy chain constant region of the anti-PRLR antibody either lacks a C-terminal lysine or comprises an amino acid other than lysine at a C-terminus of the heavy chain constant region.

In certain embodiments, the ADC of the present invention comprises the structure of Formula (X):

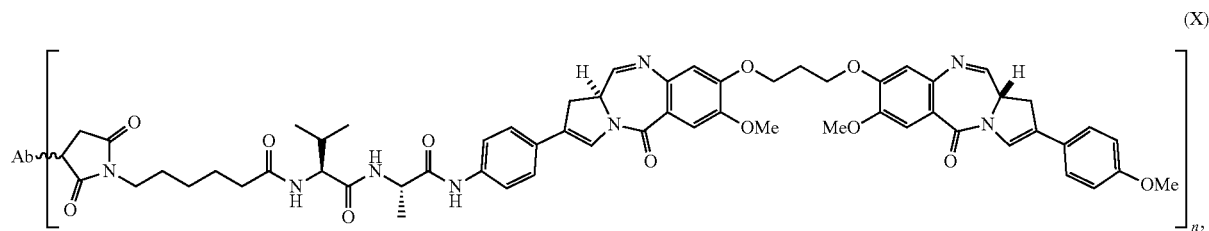

(X)

or a salt thereof, wherein Ab is an antibody comprising a heavy chain variable region comprising SEQ ID NO: 2, and a light chain variable region comprising SEQ ID NO: 7, and n is about 2 to about 4. Preferably, the anti-PRLR antibody is an IgG1 isotype having a constant region with cysteine mutation engineered to provide a conjugation site for a PBD. In one embodiment, the cysteine mutation is at position 239 of the heavy chain. Preferably, the mutation is S239C, wherein the numbering is in accordance with Kabat. In one embodiment, n is about 2 or about 4. In a preferred embodiment, n is about 2. In one embodiment, the heavy chain constant region of the anti-PRLR antibody either lacks a C-terminal lysine or comprises an amino acid other than lysine at a C-terminus of the heavy chain constant region.

In certain embodiments, the ADC of the present invention comprises the structure of Formula (X):

of the antibody, for example its ability to bind its target. Preferably, the binding properties of the conjugated antibody will closely resemble those of the unconjugated antibody. A variety of chemistries and techniques for conjugating molecules to biological molecules such as antibodies are known in the art and in particular to antibodies, are well-known. See, e.g., Amon et al., "Monoclonal Antibodies For Immunotargeting Of Drugs In Cancer Therapy," in: *Monoclonal Antibodies And Cancer Therapy*, Reisfeld et al. Eds., Alan R. Liss, Inc., 1985; Hellstrom et al., "Antibodies For Drug Delivery," in: *Controlled Drug Delivery*, Robinson et al. Eds., Marcel Dekker, Inc., 2nd Ed. 1987; Thorpe, "Antibody Carriers Of Cytotoxic Agents In Cancer Therapy: A Review," in: *Monoclonal Antibodies '84: Biological And Clinical Applications*, Pinchera et al., Eds., 1985; "Analysis, Results, and Future Prospective of the Therapeutic Use of

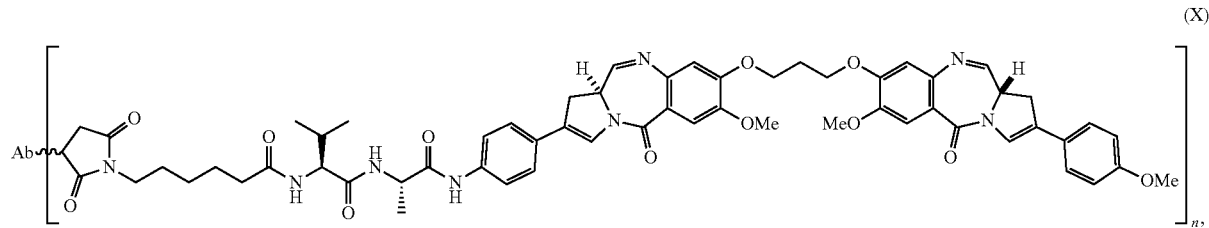

(X)

or a salt thereof, wherein Ab is an antibody comprising a heavy chain comprising the amino acid sequence set forth in SEQ ID NO: 1 and a light chain comprising the amino acid sequence set forth in SEQ ID NO: 6. In one embodiment, n is about 2 to about 4. In one embodiment, n is about 2 or about 4. In a preferred embodiment, n is about 2.

The ADCs described herein may be synthesized using chemistries that are well-known in the art. The chemistries selected will depend upon, among other things, the identity of the cytotoxic and/or cytostatic agent(s), the linker and the groups used to attach linker to the antibody. Generally, ADCs according to Formula (I) may be prepared according to the following scheme:

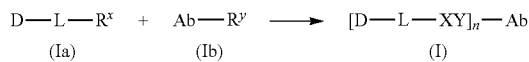

where D, L, Ab, XY and n are as previously defined above, and $R^x$ and $R^y$ represent complementary groups capable of forming covalent linkages with one another, as discussed above.

The identities of groups $R^x$ and $R^y$ will depend upon the chemistry used to link synthon D-L-$R^x$ to the antibody. Generally, the chemistry used should not alter the integrity Radiolabeled Antibody In Cancer Therapy," in: *Monoclonal Antibodies For Cancer Detection And Therapy*, Baldwin et al., Eds., Academic Press, 1985; Thorpe et al., 1982, *Immunol. Rev.* 62:119-58; PCT publication WO 89/12624. Any of these chemistries may be used to link the synthons to an antibody.

A number of functional groups $R^x$ and chemistries useful for linking synthons to accessible lysine residues are known, and include by way of example and not limitation NHS-esters and isothiocyanates.

A number of functional groups $R^x$ and chemistries useful for linking synthons to accessible free sulfhydryl groups of cysteine residues are known, and include by way of example and not limitation haloacetyls and maleimides.

However, conjugation chemistries are not limited to available side chain groups. Side chains such as amines may be converted to other useful groups, such as hydroxyls, by linking an appropriate small molecule to the amine. This strategy can be used to increase the number of available linking sites on the antibody by conjugating multifunctional small molecules to side chains of accessible amino acid residues of the antibody. Functional groups $R^x$ suitable for covalently linking the synthons to these "converted" functional groups are then included in the synthons.

An antibody may also be engineered to include amino acid residues for conjugation. An approach for engineering antibodies to include non-genetically encoded amino acid residues useful for conjugating drugs in the context of ADCs is described by Axup et al., 2012, *Proc Natl Acad Sci USA*. 109(40):16101-16106, as are chemistries and functional groups useful for linking synthons to the non-encoded amino acids.

Typically, the synthons are linked to the side chains of amino acid residues of the antibody, including, for example, the primary amino group of accessible lysine residues or the sulfhydryl group of accessible cysteine residues. Free sulfhydryl groups may be obtained by reducing interchain disulfide bonds.

For linkages where $R^y$ is a sulfhydryl group (for example, when $R^x$ is a maleimide), the antibody is generally first fully or partially reduced to disrupt interchain disulfide bridges between cysteine residues. Specific cysteine residues and interchain disulfide bridges, if present in the antibody heavy chain, may be reduced for attachment of drug-linker synthons including a group suitable for conjugation to a sulfhydryl group, and include by way of example and not limitation: residues C233, C239, and C242 (Kabat numbering system; corresponding to residues C220, C226, and C229 Eu numbering) on the human $IgG_1$ heavy chain, and residue C214 (Kabat numbering system) on the human Ig kappa light chain. In instances where an antibody heavy chain does not contain a cysteine residue at an attachment site, however, the antibody can be engineered to contain a cysteine at a given position, e.g., position 239.

Cysteine residues for synthon attachment that do not participate in disulfide bridges may be engineered into an antibody by mutation of one or more codons. Reducing these unpaired cysteines yields a sulfhydryl group suitable for conjugation. Preferred positions for incorporating engineered cysteines include, by way of example and not limitation, positions S112C, S113C, A114C, S115C, A176C, 5180C, S239C, S252C, V286C, V292C, S357C, A359C, S398C, S428C (Kabat numbering) on the human $IgG_1$ heavy chain and positions V110C, S114C, S121C, S127C, S168C, V205C (Kabat numbering) on the human Ig kappa light chain (see, e.g., U.S. Pat. No. 7,521,541, U.S. Pat. No. 7,855,275 and U.S. Pat. No. 8,455,622). In one embodiment, residue S239 (Kabat numbering system) is mutated to a cysteine to allow conjugation of a PBD warhead to an anti-PRLR antibody, e.g. antibody h16f. This mutation is referred to herein as "S239C".

In certain embodiments, the ADCs of the invention have a DAR of about 2, via the engineered cysteines. In this context, the term "about", means an amount within ±7.5% of the actual value. i.e. "about 2" means 1.85, 1.86, 1.87, 1.88, 1.89, 1.90, 1.91, 1.92, 1.93, 1.94, 1.95, 1.96, 1.97, 1.98, 1.99, 2.00, 2.01, 2.02, 2.03, 2.04, 2.05, 2.06, 2.07, 2.08, 2.09, 2.10, 2.11, 2.12, 2.13, 2.14, 2.15, and any intervening ranges. For example, in certain exemplary embodiments, the ADCs of the invention have a DAR of 1.89 or 1.96, via the engineered cysteines.

In certain embodiments, the invention features a method of making an ADC, comprising contacting an antibody heavy and light chains set forth in SEQ ID NOS: 1 and 6, respectively, with a synthon according to structural Formula (Ia), wherein D is cytotoxic and/or cytostatic agent capable of crossing a cell membrane, L is a linker capable of being cleaved by a lysosomal enzyme, and $R^x$ comprises a functional group capable of covalently linking the synthon to the antibody, under conditions in which the synthon covalently links the synthon to the antibody, wherein D is, e.g., a PBD dimer.

As will be appreciated by skilled artisans, the number of cytotoxic and/or cytostatic agents linked to an antibody molecule may vary, such that an ADC preparation may be heterogeneous in nature, where some antibodies in the preparation contain one linked agent, some two, some three, etc. (and some none). The degree of heterogeneity will depend upon, among other things, the chemistries used for linking the cytotoxic and/or cytostatic agents. For example, where the antibodies are reduced to yield sulfhydryl groups for attachment, heterogenous mixtures of antibodies having zero, 2, 4, 6 or 8 linked agents per molecule are often produced. Furthermore, by limiting the molar ratio of attachment compound, antibodies having zero, 1, 2, 3, 4, 5, 6, 7 or 8 linked agents per molecule are often produced. Thus, it will be understood that depending upon context, stated drug antibody ratios (DARs) may be averages for a collection of antibodies. For example, "DAR4" refers to an ADC preparation that has not been subjected to purification to isolate specific DAR peaks and comprises a heterogeneous mixture of ADC molecules having different numbers of cytostatic and/or cytotoxic agents attached per antibody (e.g., 0, 2, 4, 6, 8 agents per antibody), but has an average drug-to-antibody ratio of 4.

Heterogeneous ADC preparations may be processed, for example, by hydrophobic interaction chromatography ("HIC") to yield preparations enriched in an ADC having a specified DAR of interest (or a mixture of two or more specified DARS). Such enriched preparations are designed herein as "EX," where "E" indicates the ADC preparation has been processed and is enriched in an ADC having a specific DAR and "X" represents the number of cytostatic and/or cytotoxic agents linked per ADC molecule. Preparations enriched in a mixture of ADCs having two specific DARS are designated "EX/EY," three specific DARs "EX/EY/EZ" etc., where "E" indicates the ADC preparation has been processed to enrich the specified DARs and "X," "Y" and "Z" represent the DARS enriched. As specific examples, "E2" refers to an ADC preparation that has been enriched to contain primarily ADCs having two cytostatic and/or cytotoxic agents linked per ADC molecule. "E4" refers to an ADC preparation that has been enriched to contain primarily ADCs having four cytostatic and/or cytotoxic agents linked per ADC molecule. "E2/E4" refers to an ADC preparation that has been enriched to contain primarily two ADC populations, one having two cytostatic and/or cytotoxic agents linked per ADC molecule and another having four cytostatic and/or cytotoxic agents linked per ADC molecule.

As used herein, enriched "E" preparations will generally be at least about 80% pure in the stated DAR ADCs, although higher levels of purity, such as purities of at least about 85%, 90%, 95%, 98%, or even higher, may be obtainable and desirable. For example, an "EX" preparation will generally be at least about 80% pure in ADCs having X cytostatic and/or cytotoxic agents linked per ADC molecule. For "higher order" enriched preparations, such as, for example, "EX/EY" preparations, the sum total of ADCs having X and Y cytostatic and/or cytotoxic agents linked per ADC molecule will generally comprise at least about 80% of the total ADCs in the preparation. Similarly, in an enriched "EX/EY/EZ" preparation, the sum total of ADCs having X, Y and Z cytostatic and/or cytotoxic agents linked per ADC molecule will comprise at least about 80% of the total ADCs in the preparation.

Purity may be assessed by a variety of methods, as is known in the art. As a specific example, an ADC preparation may be analyzed via HPLC or other chromatography and the purity assessed by analyzing areas under the curves of the resultant peaks.

In one embodiment, the invention comprises a heterogenous composition comprising h16f (S239C)-PBD ADCs having a DAR of 2 (DAR E2), wherein the DAR E2 species is present at >80 percent (>80, 81, 82, 83, 84, 85, 86, 87, 88, 89, 90, 91, 92, 93, 94, 95, 96, 97, 98, 99 percent) of all ADCs in the composition. In one embodiment, the invention comprises a heterogenous composition comprising h16f (S239C)-PBD ADCs having a DAR of 2 (DAR E2), wherein the DAR E2 species is present at >90 percent (>90, 91, 92, 93, 94, 95, 96, 97, 98, 99 percent) of the population of all ADCs in the composition.

In certain embodiments, the DAR of the ADC of the invention is about 2 or about 4. In further embodiments, the DAR of the ADC of the invention is 2.

The ADCs described herein may be in the form of pharmaceutical compositions comprising the ADC and one or more carriers, excipients and/or diluents. The compositions may be formulated for specific uses, such as for veterinary uses or pharmaceutical uses in humans.

BRIEF DESCRIPTION OF THE SEQUENCES

Incorporated by reference herein in its entirety is a Sequence Listing entitled Sequence_Listing_12367, comprising SEQ ID NO: 1 through SEQ ID NO: 31, which includes the nucleic acid and/or amino acid sequences disclosed herein. The sequence listing has been submitted herewith in ASCII text format. This sequence listing was first created on Mar. 26, 2018 and is 56 kilobytes in size.

EXAMPLES

The following Examples, which highlight certain features and properties of exemplary embodiments of anti-PRLR ADCs are provided for purposes of illustration, and not limitation.

It should be noted that, unless otherwise described, the approximate DAR of the PBD ADCs described in the examples below is about 2; see, e.g. Example 3 (DAR of 1.89 and 1.96, considered to be about 2).

Example 1. Generation of Anti-PRLR h16f (S239C)

Antibody h16f is a humanized antibody that was initially generated from a murine parent anti-PRLR antibody that was identified from a screen of anti-PRLR antibodies having inhibitory activity in, for example, a cell proliferation assay. The light chain amino acid sequence of h16f is described in SEQ ID NO: 6, the variable region is described in SEQ ID NO: 7, and the 3 CDRs are described in SEQ ID NOS: 8 to 10. The heavy chain amino acid sequence of h16f is described in SEQ ID NO: 11, the variable region is described in SEQ ID NO: 2, and the 3 CDRs are described in SEQ ID NOs: 3 to 5.

Antibody h16f was determined to have distinct properties from anti-PRLR antibody LFA-102 (Novartis). For example, antibody h16f was determined to have slower off rates to PRLR relative to antibody LFA-102, i.e., a $k_d$ of $6.23 \times 10^{-4}$ s$^{-1}$ and a $K_d$ of $4.6 \times 10^{-10}$ M (h16f) vs. $1.10 \times 10^{-3}$ s$^{-1}$ and a $K_d$ of $1.3 \times 10^{-9}$ M (LFA-102). Further, the structure of h16f and LFA-102 anti-PRLR antibody Fab fragments bound to PRLR was determined using X-ray crystallography to determine the epitope of each. The close contact regions for antibody h16f and LFA-102 were compared and it was determined that antibody h16f binds to the PRL ligand-binding domain, a largely non-overlapping epitope from LFA-102. Thus, antibodies h16f and LFA-102 do not have the same epitope A number of humanized anti-PRLR antibodies, including antibody h16f, were conjugated to an auristatin to form ADCs and evaluated for their ability to inhibit the growth of multiple breast cancer cell lines expressing different levels of PRLR. The most potent ADC candidates were then evaluated for antitumor activity against the BT-474 human breast tumor cell line. BT-474 has ~10,000 PRLR receptors per cell, which is lower than the number typically necessary to mediate effective ADC killing, suggesting that efficient internalization may be a critical component for activity of a PRLR ADC. This tumor cell line, therefore, served as a surrogate measure of ADC internalization properties. Based on the results, the h16f antibody was identified as having the most potent inhibitory activity. The IC$_{50}$ values of the anti-PRLR ADCs is described below in Table 2 and FIG. 6. Ab-05 is a human IgG$_1$ control that recognizes tetanus toxin, which is not present in the models used.

TABLE 2

Inhibition of In Vitro Proliferation of BT-474 Cells with Humanized Anti-PRLR ADCs.

| ADC (MMAF DAR8)* | BT-474 IC$_{50}$ (nM) |
| --- | --- |
| AB095 | 33.40 |
| h5b** | 0.68 |
| h5d | 0.61 |
| h5e | 0.55 |
| h5f | 0.58 |
| h53e | 0.27 |
| h53f | 0.40 |
| h53b | 0.37 |
| h19e | 1.04 |
| h19f | 1.02 |
| h16a | 0.68 |
| h16c | 0.74 |
| h16f | 0.19 |
| h16g | 0.30 |
| h16h | 0.22 |
| LFA-102 | 1.05 |

*mAbs were conjugated to MMAF with DAR 8.
**Multiple humanized candidates were generated from each starting murine mAb.

PRLR sequence homology is well conserved between human and primates (>95%) and is poor between human and rat or mouse (<85%). The h16f antibody binds with similar affinity to human and cynomolgus monkey. Binding of the h16f antibody to either rat or mouse PRLR is significantly lower (>1,000 fold) than to human PRLR as described in Table 3.

TABLE 3

Species Cross-Reactivity: Homology and Biacore.

| PRLR Species | Percent Homology to Human | Affinity ($K_D$, nM) | |
| --- | --- | --- | --- |
| | | h16f-(S239C) | h16f (S239C)- PBD |
| Human PRLR ECD | 100 | 1.0 | 0.99 |
| Cynomolgus PRLR ECD | 98 | 0.72 | 0.71 |

TABLE 3-continued

Species Cross-Reactivity: Homology and Biacore.

| PRLR Species | Percent Homology to Human | Affinity ($K_D$, nM) | |
|---|---|---|---|
| | | h16f-(S239C) | h16f (S239C)- PBD |
| Rat PRLR ECD | 72 | 1,400 | 1,600 |
| Mouse PRLR ECD | 71 | 400 | 370 |

Note:
ECD = extracellular domain;
$K_D$ = dissociation constant;
PRLR = prolactin receptor Following identification of anti-PRLR antibody h16f, the antibody was modified in order to engineer site-specific conjugation sites of the warhead PBD. Specifically, an engineered cysteine antibody (C239) was generated in order to permit site-specific conjugation of the PBD dimer with a DAR of about 2. This mutated antibody is referred to herein as h16f (S239C) and includes an h16f light chain and a modified h16f (C239) heavy chain sequence. The heavy chain amino acid sequence of h16f (S239C) is described below in SEQ ID NO: 1. The CDRS (CDR1, CDR2, and CDR3) (SEQ ID Nos: 3 to 5) are underlined, and the variable region (SEQ ID NO: 2) is italicized.

```
                                         (SEQ ID NO: 1)
EVQLVQSGAEVKKPGSSVKVSCKASGYTFTTYWMHWVRQAPGQGLEWIGE

IDPSDSYSNYNQKFKDRATLTVDKSTSTAYMELSSLRSEDTAVYYCARNG

GLGPAWFSYWGQGTLVTVSSASTKGPSVFPLAPSSKSTSGGTAALGCLVK

DYFPEPVTVSWNSGALTSGVHTFPAVLQSSGLYSLSSVVIVPSSSLGTQT

YICNVNHKPSNTKVDKKVEPKSCDKTHTCPPCPAPELLGGPCVFLFPPKP

KDTLMISRTPEVTCVVVDVSHEDPEVKFNWYVDGVEVHNAKTKPREEQYN

STYRVVSVLTVLHQDWLNGKEYKCKVSNKALPAPIEKTISKAKGQPREPQ

VYTLPPSREEMTKNQVSLTCLVKGFYPSDIAVEWESNGQPENNYKTTPPV

LDSDGSFFLYSKLTVDKSRWQQGNVFSCSVMHEALHNHYTQKSLSLSPGK
```

The heavy chain constant region of h16f (S239C) contains a modified residue relative to its parent antibody. Specifically, residue 239 (Kabat numbering) was mutated from S to a C relative to the heavy chain of h16f. This residue is underlined/bolded above in SEQ ID NO: 1. It should be noted that S239C (Kabat numbering) corresponds to amino acid residue number 242 of SEQ ID NO: 1 (S242C).

The light chain amino acid sequence (SEQ ID NO: 6) of h16f (S239C) is provided below where CDRS 1, 2, and 3 (SEQ ID NOS: 8-10) are underlined, and the variable region (SEQ ID NO: 7) is italicized.

```
                                         (SEQ ID NO: 6)
DIQMTQSPSSVSASVGDRVTITCKASQYVGTAVAWYQQKPGKSPKLLIYS

ASNRYTGVPSRFSDSGSGTDFTLTISSLQPEDFATYFCQQYSSYPWTFGG

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
``` h16f (S239C) was further conjugated to a PBD dimer and tested as an ADC, as described in the examples below.

Figure 1:
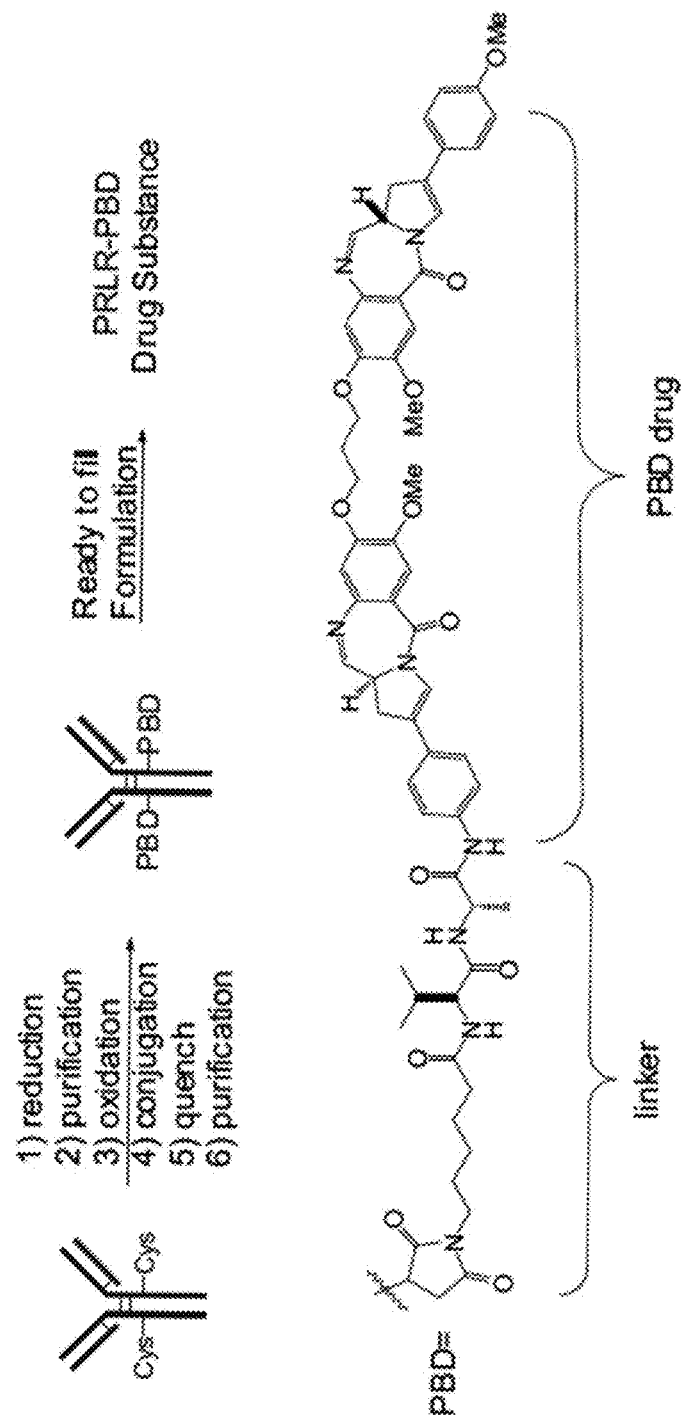
FIG. 1 shows preparation of h16f (S239C)-PBD. The conjugation process consists of reduction of the interchain disulfides, quantitative oxidation and conjugation with excess PBD drug linker, as described in Example 2.
Figure 2:
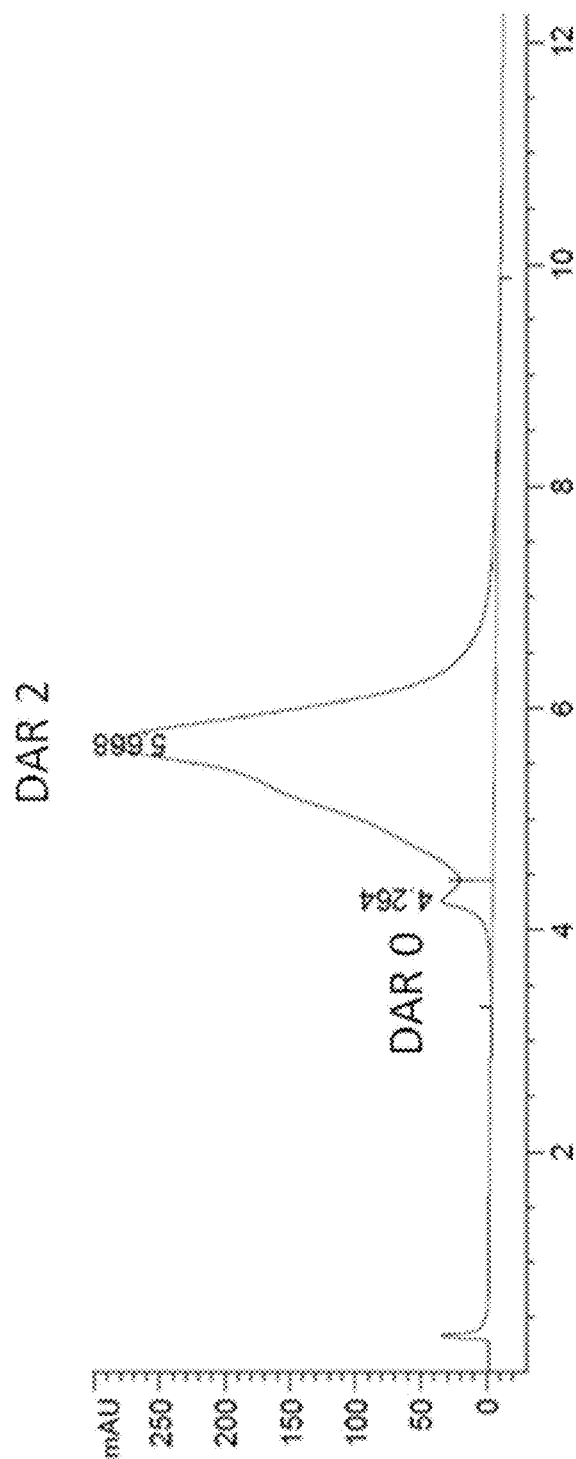
FIG. 2 is a graph that shows a hydrophobic interaction chromatography (HIC) of h16f (S239C)-PBD. Reaction parameters were identified to provide a conjugate with >80% DAR2 drug loading, as shown in Example 2.

Example 2. Generation and Physiochemical Characterization of PBD Conjugate h16f (S239C)-PBD is comprised of two PBD drug-linker molecules conjugated to Cys engineered anti-PRLR antibody h16f. The structure of the PBD and linker are described in FIG. 1. FIG. 1 also describes the process by which h16f (S239C)-PBD was prepared. The conjugation process consisted of reducing the interchain disulfides, quantitative oxidation and conjugation with excess PBD drug linker. The conjugation process consisted of a quantitative reduction of the engineered and interchain disulfides. The reduction mixture was then purified to remove the excess reagent and its byproducts, followed by quantitative oxidation of the interchain disulfides and then conjugation with excess PBD drug-linker. After quenching, the reaction mixture was purified and buffer-exchanged to yield h16f (S239C)-PBD with >80% DAR2 drug loading, as described in FIG. 2. The overall yield of the h16f (S239C)-PBD ADC after purification was approximately 80%. The conjugation process required the use of approximately 4% wt loading (~3.5 g) of the PBD drug linker.

Example 3. In Vitro Comparison of h16f (S239C)-PBD ADC Vs. h16f-MMAE ADC h16f-MMAE and h16f (S239C)-PBD conjugates were evaluated for their ability to inhibit the growth of a panel of 25 breast cancer cell lines expressing different levels of PRLR. The results of this comparative analysis are described below in Table 4 and FIG. 7. The h16f (S239C)-PBD conjugates used in this study had a DAR of 1.89 or 1.96. The 6 day proliferation assay $IC_{50}$ (nM) results are shown in Table 4 and FIG. 7.

TABLE 4

Breast Cancer Cell Line PRLR Expression and Proliferation Assay Summary with h16f (S239C)-PBD, h16f-MMAE and Control Antibody (Ab) 095 ADCs.

| | | Cell line (Receptor #) | | | | | |
|---|---|---|---|---|---|---|---|
| | | 6-Day Proliferation Assay $IC_{50}$ (nM)* | | | | | |
| Breast Cancer Line | PRLR RNA*** (Oncomine) | h16f (S239C)- PBD | Ab095- PBD | PBD Dimer | h16f- MMAE | Ab095- MMAE | Increase in PDB Potency**** |
| T47D (26,000) | 188 | 0.01 | 21.14 | 0.06 | 0.22 | >22 | 21 |
| MDAMB361+ | 38 | 0.64 | >22 | 0.21 | 0.96 | 9.7 | 1 |
| HCC1428 | 26 | 0.54 | >22 | 0.33 | 0.19 | 5.43 | 0.4 |
| BT-474.FP2 (10,000)+ | 24 | 0.27 | 14.13 | 0.38 | 0.56 | 13.09 | 2 |

TABLE 4-continued

Breast Cancer Cell Line PRLR Expression and Proliferation Assay Summary with h16f (S239C)-PBD, h16f-MMAE and Control Antibody (Ab) 095 ADCs.

| | | Cell line (Receptor #) | | | | | |
|---|---|---|---|---|---|---|---|
| | | 6-Day Proliferation Assay IC$_{50}$ (nM)* | | | | | |
| Breast Cancer Line | PRLR RNA*** (Oncomine) | h16f (S239C)- PBD | Ab095- PBD | PBD Dimer | h16f- MMAE | Ab095- MMAE | Increase in PDB Potency**** |
| MDAMB134VI | 22 | 0.11 | 26.2 | 0.16 | 0.42 | 11.75 | 4 |
| CAMA1 | 17 | 0.01 | 8.6 | 0.09 | 5.16 | 21.71 | 695 |
| MCF7 (8,000) | 12 | 0.12 | 14.53 | 0.07 | <u>>22</u> | >22 | >183 |
| HCC1500 | 8 | 0.28 | 17.43 | 0.1 | 0.97 | >22 | 3 |
| ZR751 | 8 | 0.04 | 11.31 | 0.05 | 4.07 | >22 | 92 |
| MDAMB415 | 4 | 0.9 | 13.44 | 0.06 | >22 | >22 | >24 |
| SKBR3+ | 4 | 0.26 | 12.91 | 0.04 | <u>3.67</u> | 4.64 | 14 |
| HCC70 | 3 | 0.25 | 7.18 | 0.03 | >22 | >22 | >88 |
| MDAMB175VII | 2 | <u>30</u> | >22 | 0.06 | >22 | >22 | — |
| HCC38 | 2 | <u>25.42</u> | 32.82 | 0.01 | >22 | >22 | — |
| UACC812 | 2 | <u>>22</u> | >22 | 0.44 | >22 | >22 | — |
| HCC1143 | 2 | 0.78 | 9.88 | 0.42 | 9.28 | 10.73 | 12 |
| MDAMB468 | 1 | 0.18 | 3.78 | 0.01 | 14.29 | 13.97 | 80 |
| BT549 | 1 | 8.36 | 19.49 | 0.02 | >22 | >22 | >3 |
| MDAMB436.FP9 (4,000) | 1 | <u>2.09</u> | 3.02 | 0.06 | 19.22 | 20.95 | — |
| MDAMB435SLM | 1 | >22 | >22 | 0.26 | >22 | >22 | n/a |
| MDAMB231LC3.LMC | 1 | >22 | >22 | 0.16 | >22 | >22 | n/a |
| JIMT-1 | 1 | 9.76 | 6.42 | 0.13 | 17.51 | 17.73 | n/a |
| HCC1187 | 0.7 | 0.09 | 8.06 | 0.05 | 13.93 | 8.06 | 157 |
| BT20 | 0.4 | 0.19 | 0.14 | 0.12 | >22 | >22 | n/a |
| SUM149PT | 0.2 | 9.82 | 12.03 | 0.08 | >22 | >22 | n/a |

*Breast cancer cell lines sensitive (bolded; >50% maximum inhibition), partially sensitive (underlined) and resistant (plain type). IC$_{50}$ values were determined in cell killing titration assays starting at a concentration of 3 μg/mL.
**+ denotes HER2+ cells lines; PRLR/cell determined by FACS-based antigen binding is shown for selected cell lines.
***Relative RNA expression based on microarray analysis.
****The increase in activity of the PBD conjugates relative to the MMAE conjugate is shown as fold-increase in potency as determined by the ratios of IC$_{50}$ values As described in Table 4, breast cancer cell lines that were shown to be sensitive to treatment with h16f (S239C)-PBD (>50% maximum inhibition) were: T47D (26,000), MDAMB361, HCC1428, BT474.FP2 (10,000), MDAMB134VI, CAMA1, MCF7 (8,000), HCC1500, ZR751, MDAMB415, SKBR3, HCC70, HCC1143, MDAMB468, BT549, and HCC1187. Breast cancer cell lines that were shown to be sensitive to treatment with h16f MMAE (>50% maximum inhibition) were: T47D (26,000), MDAMB361, HCC1428, BT474.FP2 (10,000), MDAMB134VI, CAMA1, HCC1500, ZR751. Breast cancer cell lines that were shown to be partially sensitive to treatment with h16f (S239C)-PBD were: MDAMB175VII, HCC38, UACC812 and MDAMB436.FP9 (4,000). Breast cancer cell lines that were shown to be partially sensitive to treatment with h16f MMAE-PBD were: MCF7 (8,000) and SKBR3.

The increase in activity of the PBD conjugate relative to the MMAE conjugate is shown as fold-increase in potency as determined by the ratios of IC$_{50}$ values. As shown in Table 6, the PBD conjugates showed an increase in potency compared to MMAE conjugates of antibody (h16f).

Measurement of PRLR receptor densities on these tumor cells permitted an assessment of the correlation between receptor expression and sensitivity to ADC-mediated killing. Results described in Table 4 and FIG. 7 indicated cell line sensitivity to killing by the ADC correlated with PRLR mRNA and protein expression. PRLR was overexpressed in both HER2+ and HER2− tumors. Every tumor cell line sensitive to killing by h16f-MMAE ADC was surprisingly equally or more sensitive to killing by h16f (S239C)-PBD. Additionally, several tumor cell lines with lower levels of PRLR were sensitive to killing by the PBD conjugate but were largely insensitive to h16f-MMAE. These results suggest that h16f (S239C)-PBD is more potent than h16f-MMAE and may provide additional treatment options for sensitive tumors.

BT-474 has ~10,000 PRLR per cell, which is lower than the expression typically required to mediate effective ADC killing for other receptors such as ERBB2, MET and EGFR, though similar to levels seen with other targets such as tissue factor and LGR5. The sensitivity of BT-474 to PRLR ADC-mediated cell killing suggests that efficient internalization and/or internal processing is a critical component for ADC activity. Immunofluorescence and warhead quantification studies have confirmed rapid internalization of the ADC.

Since the PRLR/PRL axis has been implicated in other tissues, including reproductive tissues and prostate (Martei et al. (2015) *Breast Cancer* 7:337-343; Damiano et al. (2013) *Clin Cancer Res* 19:1644-1650), h16f-MMAE and -PBD conjugates were evaluated for their ability to inhibit the growth of non-breast-derived tumor cell lines as described in Table 5 and FIG. 8. Although the levels of PRLR RNA in these cell lines was generally much lower than observed for many breast cancer cell lines, several cell lines were sensitive to killing by h16f (S239C)-PBD, but not h16f-MMAE. These results suggest that h16f (S239C)-PBD may be effective in treating in tumor types other than breast cancer.

TABLE 5

PRLR Expression and Proliferation Assay Data with h16f-PBD, h16f-MMAE and Control (Ab095) ADCs.

| Breast Cancer Line | PRLR RNA*** (Oncomine) | h16f (S239C)-PBD | Ab095-PBD | PBD Dimer | h16f-MMAE | Ab095-MMAE | Increase in PDB Potency**** |
|---|---|---|---|---|---|---|---|
| \multicolumn{8}{c}{Cell line (Receptor #)} | | | | | | | |
| \multicolumn{8}{c}{6-Day Proliferation Assay IC$_{50}$ (nM)*} | | | | | | | |
| \multicolumn{8}{c}{Ovarian Cancer} | | | | | | | |
| SMOV2 (2300) | n.d. | 0.16 | 17.44 | 0.02 | >22 | >22 | >138 |
| ES2.LMC | 1 | 15 | 21.52 | 0.18 | >22 | >22 | >1.5 |
| HeyA8.LMC | 0.4 | >22 | >22 | 0.39 | >22 | >22 | n/a |
| \multicolumn{8}{c}{Endometrial Cancer} | | | | | | | |
| AN3CA | 2 | 0.6 | 4.35 | 0.02 | 21.68 | 23.3 | 36 |
| \multicolumn{8}{c}{Prostate Cancer} | | | | | | | |
| 22Rv1 | 2 | 0.01 | 7.56 | 0.09 | >22 | >22 | >2200 |
| PC3 | 0.4 | >22 | >22 | 0.09 | >22 | 19.66 | n/a |
| \multicolumn{8}{c}{Colon Cancer} | | | | | | | |
| SW403 | 3 | 0.11 | 21.94 | 0.06 | 17.46 | 13.78 | 152 |
| LoVo | 2 | >22 | >22 | 0.13 | >22 | 15.54 | n/a |
| LS174T | 0.4 | 0.13 | 2.88 | 0.01 | >22 | >22 | 169 |
| SW48 | 0.4 | 1.97 | 2.24 | 0.02 | 21.62 | 20.37 | n/a |
| \multicolumn{8}{c}{Liver Cancer} | | | | | | | |
| HepG2 | 3 | 8.59 | 15.97 | 0.06 | >22 | >22 | — |
| HuH7 | 2 | 5.22 | 11.79 | 0.06 | >22 | >22 | 4 |
| Hep3B | 0.3 | 9.69 | 7.71 | 0.05 | >22 | >22 | — |
| \multicolumn{8}{c}{Gastric Cancer} | | | | | | | |
| IM95 | 2 | 5.67 | 18.18 | 0.17 | 19.85 | 24.15 | 4 |
| \multicolumn{8}{c}{Lung Cancer} | | | | | | | |
| NCI-H1048 | 2 | 3.09 | 5.32 | 0.03 | >22 | >22 | — |
| NCI-h1395 | 1 | >22 | >22 | 0.63 | >22 | >22 | n/a |
| \multicolumn{8}{c}{Recombinant Expression} | | | | | | | |
| HEK293/Human PRLR | | <0.01 | 1.92 | 0.02 | 0.15 | 64.72 | >15 |
| HEK293/Vector | 0.2 | 2.74 | 2.27 | 0.02 | >22 | >22 | n/a |

*Tumor cell line sensitivity: (bold (SMOV2 (2300), ES2.LMC, AN3CA, 22Rv1, SW403, LS174T, HuH7, HEK293/Human PRLR); >50% maximum inhibition), partially sensitive (underlined (HepG2, Hep3B, NCI-H1048)) and resistant (plain). IC$_{50}$ values were determined in cell killing titration assays starting at a concentration of 3 µg/mL.
**PRLR/cell determined by FACS-based antigen binding shown for select cell line.
***Relative RNA expression based on microarray analysis
****The increase in activity of the PBD conjugate relative to the MMAE conjugate is shown as fold-increase in potency as determined by the ratios of IC$_{50}$ values.

The increase in activity of the PBD conjugate relative to the MMAE conjugate is shown as fold-increase in potency as determined by the ratios of IC$_{50}$ values. As shown in Table 5, the h16f (S239C)-PBD conjugates showed an increase in potency compared to MMAE conjugates of h16f.

Example 4. In Vivo Characterization of PRLR ADCs

In vivo studies using the BT-474 xenograft model in mouse subjects were performed using both h16f conjugated auristatin payloads and PBD payloads in order to compare the activities of the two warheads in the context of a critically identical antibody.

Figure 3A:
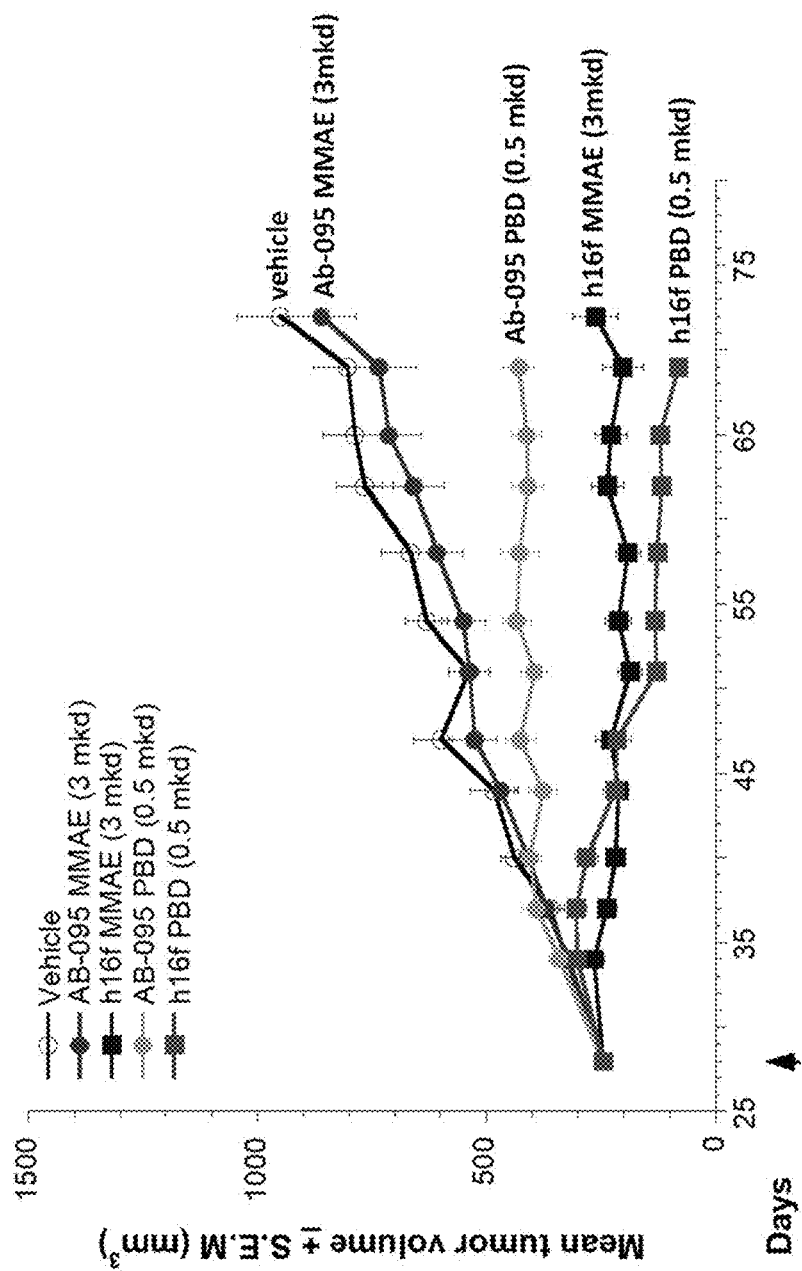
FIG. 3A is a graph that shows the comparison of in vivo efficacy of h16f (S239C)-PBD and h16f-MMAE using the BT-474 xenograft model. Mice were dosed with either vehicle only, Ab-095 MMAE (3 mkd (mg/kg/day)), h16f MMAE (3 mkd), Ab-095PBD (0.5 mkd) or h16f (0.5 mkd). Mean tumor volume was measured in $mm^3$. Arrows on the x-axis denote administration time points. Ab-05 is a human $IgG_1$ control that recognizes tetanus toxin, which is not present in the models used As shown and described in Example 4, the in vivo efficacy of h16f (S239C)-PBD at 0.5 mg/kg was significantly improved compared to h16f-MMAE at 3 mg/kg with a single dose (QDx1) dosing regimen.

BT-474 is an ER+, progesterone receptor (PR)-, HER2+ breast cancer cell line that expresses ~10,000 PRLR receptors per cell, and in vitro efficacy of h16f (S239C)-PBD (0.27 nM) was very similar to h16f-MMAE ADC (0.56 nM) (see Table 5). In contrast, and surprisingly, the in vivo efficacy of h16f (S239C)-PBD at 0.5 mg/kg was significantly improved compared to h16f-MMAE at 3 mg/kg with a single dose (QDx1) dosing regimen as described in FIG. 3A. In a subsequent Q7Dx3 study (where mice were dosed every 7 days for 3 weeks; Q7Dx3), 0.3 mg/kg and 0.2 mg/kg dosing of h16f (S239C)-PBD was superior to 3 mg/kg dosing of h16f-MMAE, as described in FIG. 3B.

To further assess the antitumor activity of h16f (S239C)-PBD, an "n of 3" targeted study in 15 breast cancer patient-derived xenograft (PDX) primarily, but not exclusively, triple negative breast cancer (TNB) tumor models (commercially available from Champions Oncology) that express a range from weak to moderate PRLR was performed. The study and results are described in Table 8. PRLR density in this table is reflected as a comparison to the PRLR number on the MCF7 tumor cell line (8,000 receptors per cell; see Table 4). As summarized in Table 6 and FIG. 9, results surprisingly indicated that h16f (S239C)-PBD is more active than h16f-MMAE in most of the PDX models that have been evaluated. One additional TNB PDX model, BR-0851 that was evaluated was insensitive to h16f (S239C)-PBD.

TABLE 6

Human Breast Cancer PDX Models with
h16f(S239C)-PBD vs. h16f-MMAE ADCs

|  | Species/ Strain | Doses and Regimen | Gender and No. per Group | Noteworthy Findings |
|---|---|---|---|---|
| CTG 1124 Breast PDX Model | Mouse/ Harlan; nu/nu | 0.2 mg/kg/day at Q7Dx3 | Female n = 3/group | Expression 0.77; Efficacy High |
| CTG 0012 Breast PDX Model | Mouse/ Harlan; nu/nu | 0.5 mg/kg/day at Q7Dx3 | Female n = 3/group | Expression 0.75; Efficacy High |
| CTG 00869 Breast PDX Model | Mouse/ Harlan; nu/nu | 0.5 mg/kg/day at Q7Dx3 | Female n = 3/group | Expression 0.8; Efficacy High |
| CTG 0670 Breast PDX Model | Mouse/ Harlan; nu/nu | 0.5 mg/kg/day at Q7Dx3 | Female n = 3/group | Expression 1.6; Efficacy High 96% |
| CTG 1019 Breast PDX Model | Mouse/ Harlan; nu/nu | 0.2 mg/kg/day at Q7Dx3 | Female n = 3/group | Expression 0.33; Efficacy High |
| CTG 1242 Breast PDX Model | Mouse/ Harlan; nu/nu | 0.2 mg/kg/day at Q7Dx3 | Female n = 3/group | Expression 1.9; Efficacy High |
| CTG 1171 Breast PDX Model | Mouse/ Harlan; nu/nu | 0.2 mg/kg/day at Q7Dx3 | Female n = 3/group | Expression 0.89; Efficacy High |
| CTG 0033 Breast PDX Model | Mouse/ Harlan; nu/nu | 0.2 mg/kg/day at Q7Dx3 | Female n = 6/group | Expression 1.1; Efficacy High |
| CTG 0017 Breast PDX Model | Mouse/ Harlan; nu/nu | 0.2 mg/kg/day at Q7Dx3 | Female n = 3/group | Expression 0.29; Efficacy Moderate |
| CTG 0052 Breast PDX Model | Mouse/ Harlan; nu/nu | 0.2 mg/kg/day at Q7Dx3 | Female n = 3/group | Expression 0.30; Efficacy Moderate | a. All in vivo efficacy studies were performed using human patient-derived xenograft models grown subcutaneously as xenografts in the mouse flank. PRLR expression level is expressed relative to MCF7, a low expressing tumor (approximately 8000 receptors/cell in culture) as a benchmark. TGI = maximum tumor growth inhibition relative to the control group. Efficacy was classified as: Low = 25-50% TGI, Moderate = 50-75% TGI or High >75% TGI.

Figure 4B:
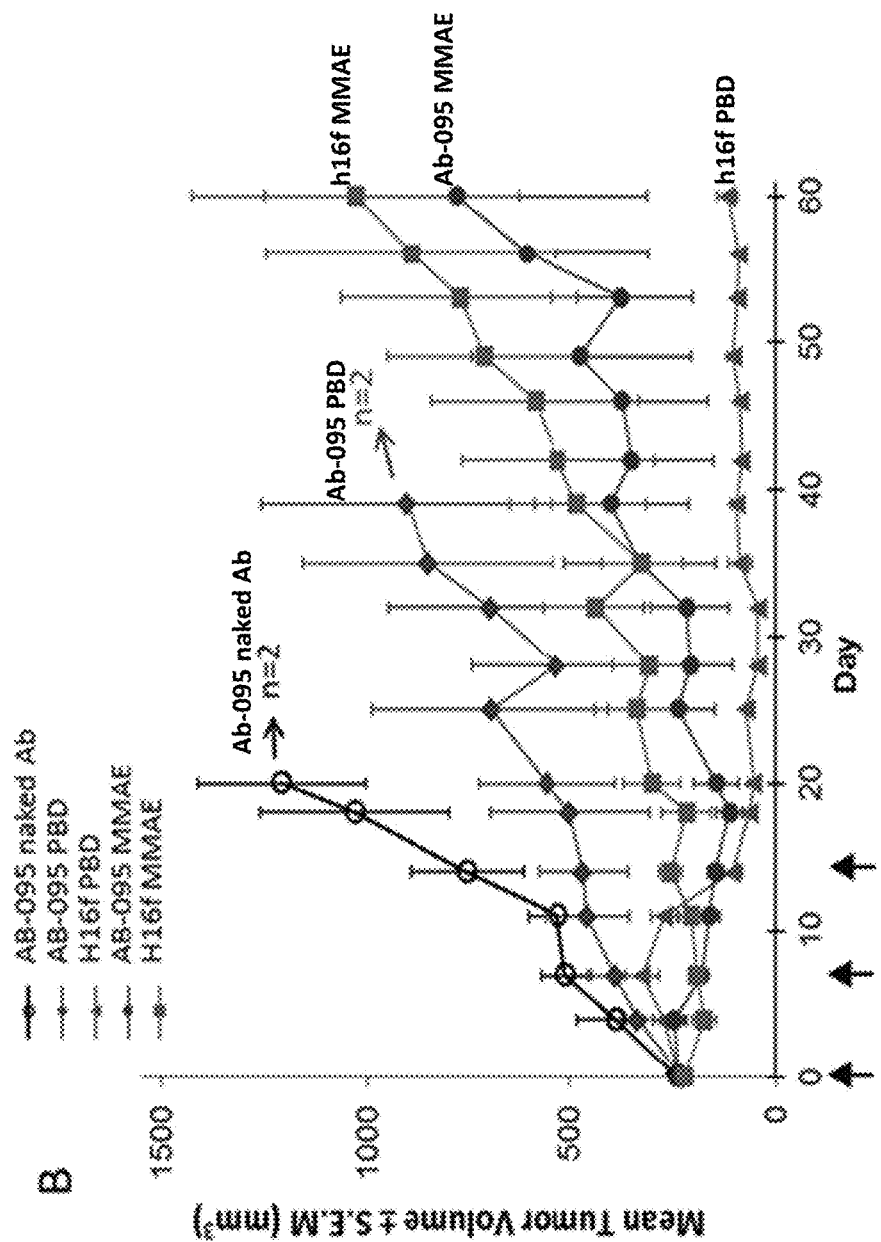
FIG. 4B is a graph that shows in vivo efficacy of h16f (S239C)-PBD with a TNB CTG-0670 tumor model. Mice were dosed with either Ab-095 naked antibody, Ab-095 PBD, h16f PBD, Ab-095 MMAE, or h16f MMAE. As shown and described in Example 4, h16f (S239C)-PBD is a more potent ADC conjugate than auristatin-based ADCs and its activity can extend to lower PRLR-expressing tumors.

Tumor growth inhibition for selected PDX models from the screen described in Table 6 is shown in FIG. 4A and FIG. 4B. CTG-0012 is an example of a TNB tumor model in which h16f (S239C)-PBD and h16 MMAE showed surprisingly similar efficacy although the PBD conjugate was dosed at a 10-fold lower concentration than is the MMAE conjugate, while CTG-0670 is an example of TNB tumor model where a 10-fold lower dose of h16f (S239C)-PBD has more effective than h16f-MMAE. The results from the comparative studies using the CTG-0012, CTG-0670, and CTG-0869 models are described in FIG. 4A, FIG. 4B, and FIG. 4C, respectively. Consistent with the results from the in vitro assay (Table 5), these data indicate that h16f (S239C)-PBD is a more potent ADC conjugate than auristatin-based ADCs and that its activity can extend to lower PRLR-expressing tumors.

Example 5. In Vitro Plasma Stability

Figure 5A:
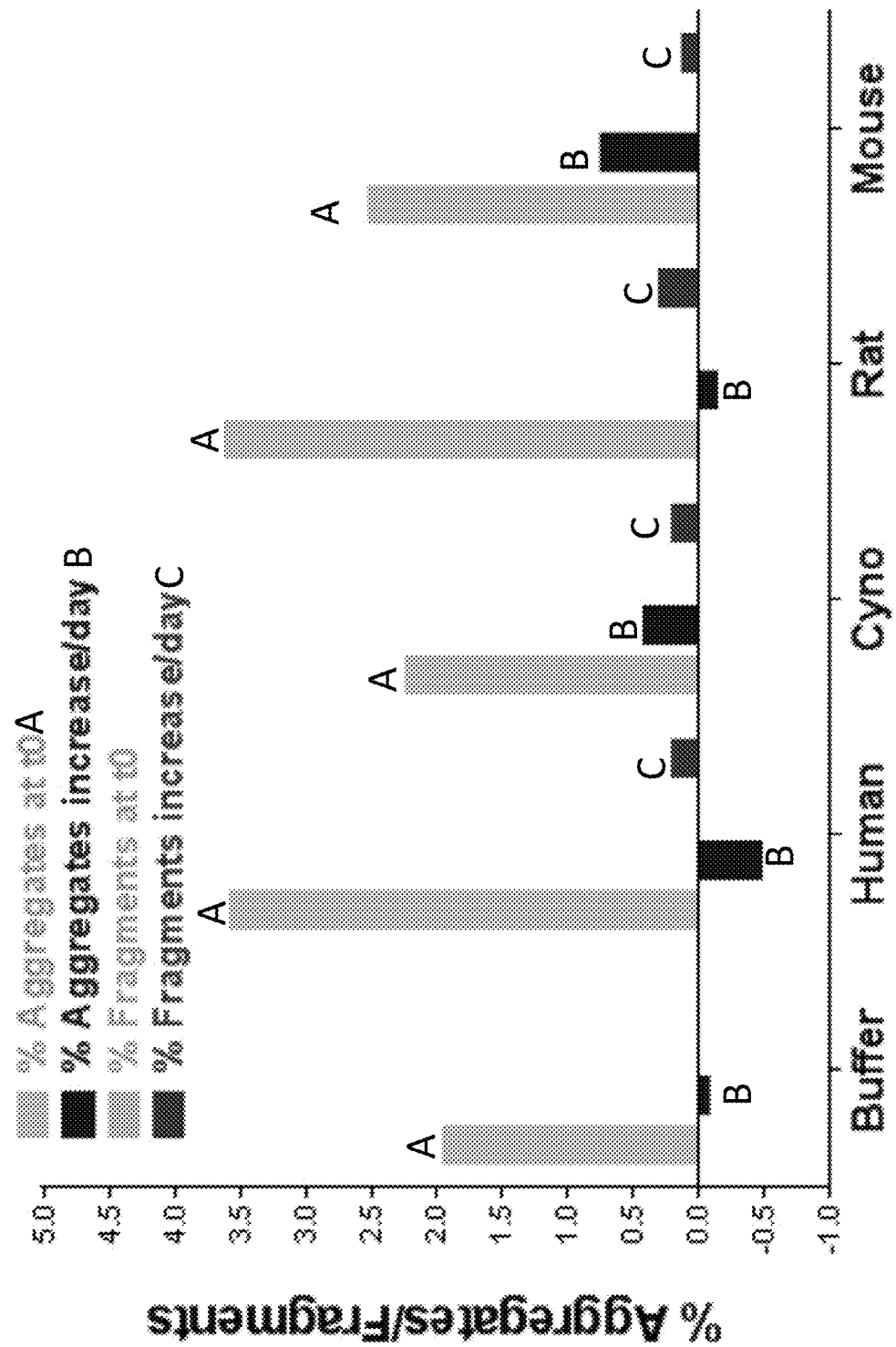
FIG. 5A is a graph that shows protein aggregation and fragmentation for h16f (S239C). Percent (%) aggregates and % fragments are shown at time "0" (t0) and as percent fragment increase per day and percent aggregate increase per day. As shown and described in Example 5, the in vitro plasma stability of the h16f (S239C) mAb and h16f (S239C)-PBD DAR2 was similar to, if not better than, h16f and h16f-vcMMAE DAR3p.

The stability of fluorescently labeled h16f (S239C) antibody and h16f (S239C)-PBD DAR2 was evaluated in vitro at 37° C. for 6 days in plasma from mouse, rat, cyno, and human as well as in buffer. Protein aggregation and fragmentation were measured by size exclusion chromatography (SEC); unconjugated PBD was determined by liquid chromatography-mass spectrometry (LC/MS/MS). h16f (S239C) mAb showed 2-4% initial aggregates at t0 with minimal percent increase/day (≤0.7%) for buffer and plasma. The antibody had 0% initial fragments at t0 and minimal % increase/day (≤0.3%) in all matrices tested. h16f (S239C)-PBD DAR2 ADC showed variable initial aggregates (0-4%) and fragments (0-1.4%) at t0 in buffer and plasma. The ADC had higher percentage aggregate increase/day in plasma (0.4-4%) compared to buffer with human>cyno>rat~mouse plasma. The percent fragment increase/day was minimal (≤0.2%) in all matrices as described in FIG. 5A and FIG. 5B. The PBD warhead itself was tested and found to be stable in plasma at 37° C. for 6 days in all species. The unconjugated warhead released from h16f (S239C)-PBD DAR2 was below the level of quantitation at all time points and in all matrices. This corresponds to <0.7% of warhead equivalent dosed. Overall the in vitro plasma stability of the h16f (S239C) mAb and h16f (S239C)-PBD DAR2 was similar to (if not better than) h16f and h16f-vcMMAE DAR3p.

These results support the surprising and unexpected finding that h16f (S239C)-PBD ADCs of the present invention having a low drug to antibody ratio (DAR), surprisingly provide a highly efficacious ADC. Taken together, the present invention describes ADC h16f (S239C)-PBD that is a more potent ADC conjugate than an auristatin-based ADC using essentially the same antibody backbone.

Example 6. Comparison of Specific Binding to PRLR Between S239C Mutants

Parental and S239C mutant antibodies were compared in a FACS titration experiment on control and PRLR-expressing HEK-293 cells. The four antibodies tested were h16f, h19e, h16f (S239C), and h19e (S239C). The results are shown in FIG. 10. Briefly, h16f (S239C) mAb had similar binding to PRLR-expressing HEK-293 cells as h16f. Surprisingly however, h19e (S239C) mAb showed a 7-fold decrease in binding affinity compared to its parent, h19e. Thus, comparatively, the S239C mutation did not affect the binding affinity of h16f (S239C), but dramatically affected the binding affinity of h19e (S239C). See Tables 7 and 8 infra for a comparison between sequences between h16f, h16f (S239C), h19e, and h19e (S239C). These results support the surprising and unexpected finding that h16f (S239C) does not have a reduced binding affinity to PRLR relative to parent h16f, unlike h19e.

Taken with the findings in the previous Examples supra, the ADC construct h16f (S239C)-PBD therefore (1) is stable under a variety of conditions (see Example 5); (2) is considerably more potent than an auristatin-based ADC using essentially the same antibody backbone (see Examples 3-4, both in vitro and in vivo); (3) displays little to no reduced binding affinity to PRLR relative to its parent antibody, unlike similar antibodies bearing an S239C mutation (see Example 6 and FIG. 10); and (4) has a surprisingly low drug to antibody ratio (DAR) of about 2, e.g. 1.89, 1.96 (see Example 3).

Antibody Sequence Tables

TABLE 7

AMINO ACID SEQUENCES OF ANTI-PRLR ANTIBODIES h16f and h16f (S239C)

| SEQ ID NO | Description | Sequence |
|---|---|---|
| 1 | h16f (S239C) heavy chain (HC) NOTE: h16f has the same HC sequence as h16f (S239C) only with a Ser at position 239; see SEQ ID NO: 11 | EVQLVQSGAEVKKPGSSVKVSCKASGYTFTTYWMHWVRQAPGQGLEWI GEIDPSDSYSNYNQKFKDRATLTVDKSTSTAYMELSSLRSEDTAVYYC ARNGGLGPAWFSYWGQGTLVTVSSASTKGPSVFPLAPSSKSTSGGTAA LGCLVKDYFPEPVTVSWNSGALTSGVHTFPAVLQSSGLYSLSSVVTVP SSSLGTQTYICNVNHKPSNTKVDKKVEPKSCDKTHTCPPCPAPELLGG P<u>C</u>VFLFPPKPKDTLMISRTPEVTCVVVDVSHEDPEVKFNWYVDGVEVH NAKTKPREEQYNSTYRVVSVLTVLHQDWLNGKEYKCKVSNKALPAPIE KTISKAKGQPREPQVYTLPPSREEMTKNQVSLTCLVKGFYPSDIAVEW ESNGQPENNYKTTPPVLDSDGSFFLYSKLTVDKSRWQQGNVFSCSVMH EALHNHYTQKSLSLSPGK (SEQ ID NO: 1) |
| 2 | h16f HC variable region | EVQLVQSGAEVKKPGSSVKVSCKASGYTFTTYWMHWVRQAPGQGLEW IGEIDPSDSYSNYNQKFKDRATLTVDKSTSTAYMELSSLRSEDTAVY YCARNGGLGPAWFSYWGQGTLVTVSS (SEQ ID NO: 2) |
| 3 | h16f HC CDR1 antibody | GYTFTTYWMH (SEQ ID NO: 3) |
| 4 | h16f HC CDR2 | EIDPSDSYSNYNQKFKD (SEQ ID NO: 4) |
| 5 | h16f HC CDR3 antibody | NGGLGPAWFSY (SEQ ID NO: 5) |
| 6 | h16f light chain (LC) | DIQMTQSPSSVSASVGDRVTITCKASQYVGTAVAWYQQKPGKSPKLL IYSASNRYTGVPSRFSDSGSGTDFTLTISSLQPEDFATYFCQQYSSY PWTFGGGTKVEIKRTVAAPSVFIFPPSDEQLKSGTASVVCLLNNFYP REAKVQWKVDNALQSGNSQESVTEQDSKDSTYSLSSTLTLSKADYEK HKVYACEVTHQGLSSPVTKSFNRGEC (SEQ ID NO: 6) |
| 7 | h16f LC variable region | DIQMTQSPSSVSASVGDRVTITCKASQYVGTAVAWYQQKPGKSPKLL IYSASNRYTGVPSRFSDSGSGTDFTLTISSLQPEDFATYFCQQYSSY PWTFGGGTKVEIK (SEQ ID NO: 7) |
| 8 | h16f LC CDR1 | KASQYVGTAVA (SEQ ID NO: 8) |
| 9 | h16f LC CDR2 | SASNRYT (SEQ ID NO: 9) |
| 10 | h16f LC CDR3 | QQYSSYPWT (SEQ ID NO: 10) |
| 11 | h16f heavy chain (HC) | EVQLVQSGAEVKKPGSSVKVSCKASGYTFTTYWMHWVRQAPGQGLEW IGEIDPSDSYSNYNQKFKDRATLTVDKSTSTAYMELSSLRSEDTAVY YCARNGGLGPAWFSYWGQGTLVTVSSASTKGPSVFPLAPSSKSTSGG TAALGCLVKDYFPEPVTVSWNSGALTSGVHTFPAVLQSSGLYSLSSV VTVPSSSLGTQTYICNVNHKPSNTKVDKKVEPKSCDKTHTCPPCPAP ELLGGP<u>S</u>VFLFPPKPKDTLMISRTPEVTCVVVDVSHEDPEVKFNWYV |

TABLE 7-continued

AMINO ACID SEQUENCES OF ANTI-PRLR ANTIBODIES h16f and h16f (S239C)

| SEQ ID NO | Description | Sequence |
|---|---|---|
| | | DGVEVHNAKTKPREEQYNSTYRVVSVLTVLHQDWLNGKEYKCKVSNK ALPAPIEKTISKAKGQPREPQVYTLPPSREEMTKNQVSLTCLVKGFY PSDIAVEWESNGQPENNYKTTPPVLDSDGSFFLYSKLTVDKSRWQQG NVFSCSVMHEALHNHYTQKSLSLSPGK (SEQ ID NO: 11) |

NOTE:
h16f (S239C) and h16f contain the same amino acid sequences in the light and heavy chain except for the single amino acid change in (S239C) in the constant region of the heavy chain, as described above.

TABLE 8

AMINO ACID SEQUENCES OF ANTI-PRLR ANTIBODIES h16e and h16e (S239C)

| SEQ ID NO | Description | Sequence |
|---|---|---|
| 21 | h19e (S239C) heavy chain (HC) NOTE: h19e has the same HC sequence as h16e (S239C) only with a Ser at position 239; see SEQ ID NO: 30 | EVQLVQSGAEVKKPGASVKVSCKASGYTFTDYNIHWVRQAPGQGLEWI GYIYPNNDGTGYNQKFKSRATLTVDNSTSTAYMELRSLRSDDTAVYYC ARGDGNYVGDMDYWGQGTTVTVSSASTKGPSVFPLAPSSKSTSGGTAA LGCLVKDYFPEPVTVSWNSGALTSGVHTFPAVLQSSGLYSLSSVVTVP SSSLGTQTYICNVNHKPSNTKVDKKVEPKSCDKTHTCPPCPAPELLGG PCVFLFPPKPKDTLMISRTPEVTCVVVDVSHEDPEVKFNWYVDGVEVH NAKTKPREEQYNSTYRVVSVLTVLHQDWLNGKEYKCKVSNKALPAPIE KTISKAKGQPREPQVYTLPPSREEMTKNQVSLTCLVKGFYPSDIAVEW ESNGQPENNYKTTPPVLDSDGSFFLYSKLTVDKSRWQQGNVFSCSVMH EALHNHYTQKSLSLSPGK (SEQ ID NO: 21) |
| 22 | h19e HC variable region | EVQLVQSGAEVKKPGASVKVSCKASGYTFTDYNIHWVRQAPGQGLEW IGYIYPNNDGTGYNQKFKSRATLTVDNSTSTAYMELRSLRSDDTAVY YCARGDGNYVGDMDYWGQGTTVTVSS (SEQ ID NO: 22) |
| 23 | h19e HC CDR1 antibody | GYTFTDYNIH (SEQ ID NO: 23) |
| 24 | h19e HC CDR2 | YIYPNNDGTGYNQKFKS (SEQ ID NO: 24) |
| 25 | h19e HC CDR3 antibody | GDGNYVGDMDY (SEQ ID NO: 25) |
| 26 | h19e light chain (LC) | DIQMTQSPSSLSASVGDRVTITCRASENIYSYLAWYQQKPGKPPKLL VYNAKTLAEGVPSRFSGSGSGTDFTLTISSLQPEDFATYYCQHHYAT PFTFGQGTKLEIKRTVAAPSVFIFPPSDEQLKSGTASVVCLLNNFYP REAKVQWKVDNALQSGNSQESVTEQDSKDSTYSLSSTLTLSKADYEK HKVYACEVTHQGLSSPVTKSFNRGEC (SEQ ID NO: 26) |
| 27 | h19e LC variable region | DIQMTQSPSSLSASVGDRVTITCRASENIYSYLAWYQQKPGKPPKLL VYNAKTLAEGVPSRFSGSGSGTDFTLTISSLQPEDFATYYCQHHYAT PFTFGQGTKLEIK (SEQ ID NO: 27) |
| 28 | h19e LC CDR1 | RASENIYSYLA (SEQ ID NO: 28) |
| 29 | h19e LC CDR2 | NAKTLAE (SEQ ID NO: 29) |
| 30 | h19e LC CDR3 | QHHYATPFT (SEQ ID NO: 30) |
| 31 | h19e heavy chain (HC) | EVQLVQSGAEVKKPGASVKVSCKASGYTFTDYNIHWVRQAPGQGLEW IGYIYPNNDGTGYNQKFKSRATLTVDNSTSTAYMELRSLRSDDTAVY YCARGDGNYVGDMDYWGQGTTVTVSSASTKGPSVFPLAPSSKSTSGG TAALGCLVKDYFPEPVTVSWNSGALTSGVHTFPAVLQSSGLYSLSSV VTVPSSSLGTQTYICNVNHKPSNTKVDKKVEPKSCDKTHTCPPCPAP ELLGGPSVFLFPPKPKDTLMISRTPEVTCVVVDVSHEDPEVKFNWYV |

TABLE 8-continued

AMINO ACID SEQUENCES OF ANTI-PRLR ANTIBODIES h16e and h16e (S239C)

| SEQ ID NO | Description | Sequence |
|---|---|---|
| | | DGVEVHNAKTKPREEQYNSTYRVVSVLTVLHQDWLNGKEYKCKVSNK ALPAPIEKTISKAKGQPREPQVYTLPPSREEMTKNQVSLTCLVKGFY PSDIAVEWESNGQPENNYKTTPPVLDSDGSFFLYSKLTVDKSRWQQG NVFSCSVMHEALHNHYTQKSLSLSPGK (SEQ ID NO: 31) |

NOTE:
h19e (S239C) and h19e contain the same amino acid sequences in the light and heavy chain except for the single amino acid change in (S239C) in the constant region of the heavy chain, as described above.

All publications, patents, patent applications and other documents cited in this application are hereby incorporated by reference in their entireties for all purposes to the same extent as if each individual publication, patent, patent application or other document were individually indicated to be incorporated by reference for all purposes.

While various specific embodiments have been illustrated and described, it will be appreciated that various changes can be made without departing from the spirit and scope of the invention(s).

What is claimed is:

1. An antibody-drug conjugate (ADC) comprising the structure of Formula (X), or a salt thereof,

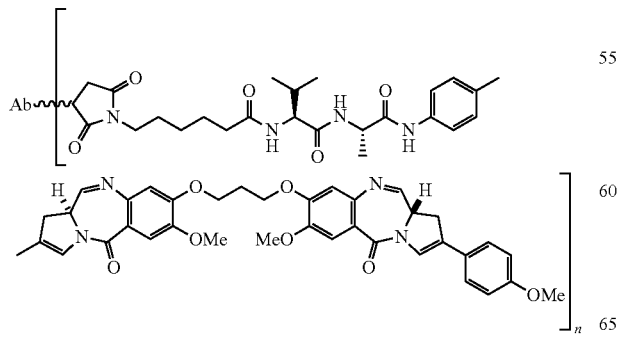

Formula (X)

wherein Formula (X) comprises a monoclonal anti-PRLR antibody (Ab) conjugated to "n" cytotoxic warheads, wherein said monoclonal anti-PRLR antibody comprises:

i. a heavy chain variable region comprising a CDRH1 sequence comprising SEQ ID NO: 3, a CDRH2 sequence comprising SEQ ID NO: 4, and a CDRH3 sequence comprising SEQ ID NO: 5;

ii. a light chain variable region comprising a CDRL1 sequence comprising SEQ ID NO: 8, a CDRL2 sequence comprising SEQ ID NO: 9, and a CDRL3 sequence comprising SEQ ID NO: 10; and iii. a mutation comprising S239C in a heavy chain constant region, wherein the numbering is in accordance with Kabat, wherein said monoclonal anti-PRLR antibody is conjugated to said cytotoxic warheads through said S239C mutation in said heavy chain constant region, and wherein "n" is 2.

2. An antibody-drug conjugate (ADC) comprising the structure of Formula (X), or a salt thereof,

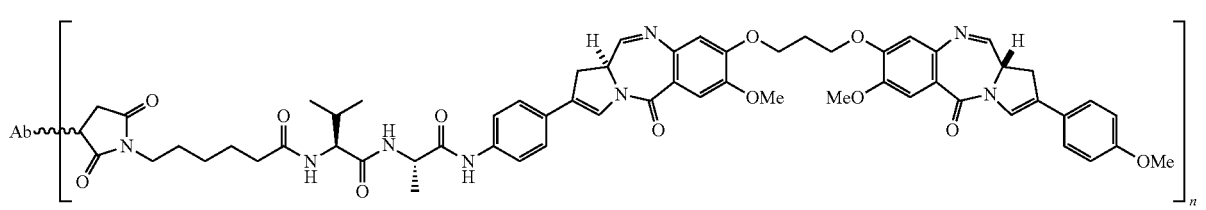

Formula (X)

wherein Formula (X) comprises a monoclonal anti-PRLR antibody (Ab) conjugated to "n" cytotoxic warheads,
wherein said monoclonal anti-PRLR antibody comprises:
i. a heavy chain variable region comprising SEQ ID NO: 2;
ii. a light chain variable region comprising SEQ ID NO: 7;
iii. a mutation comprising S239C in a heavy chain constant region, wherein the numbering is in accordance with Kabat,
wherein said monoclonal anti-PRLR antibody is conjugated to said cytotoxic warheads through said S239C mutation in said heavy chain constant region, and
wherein "n" is 2.

3. An antibody-drug conjugate (ADC) comprising the structure of Formula (X), or a salt thereof,

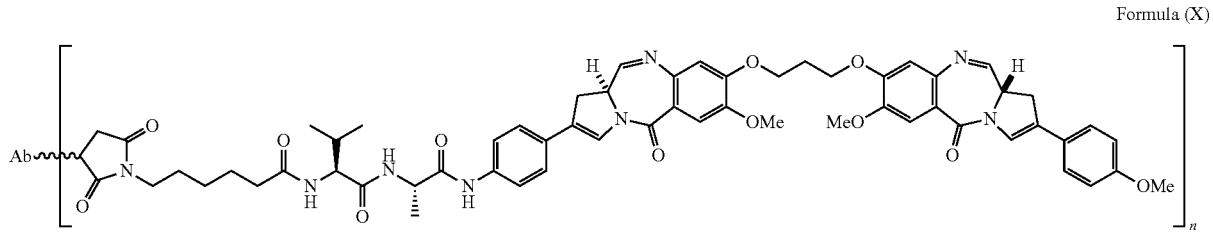

Formula (X)

wherein Formula (X) comprises a monoclonal anti-PRLR antibody (Ab) conjugated to "n" cytotoxic warheads,
wherein said monoclonal anti-PRLR antibody comprises:
i. a full heavy chain comprising SEQ ID NO: 1; and
ii. a full light chain comprising SEQ ID NO: 6,
wherein said monoclonal anti-PRLR antibody is conjugated to said cytotoxic warheads through amino acid residue 242 of SEQ ID NO: 1, and wherein "n" is 2.

4. The ADC of claim 1, wherein said monoclonal anti-PRLR antibody comprises an IgG1 isotype.

5. The ADC of claim 1, wherein said heavy chain constant region of said monoclonal anti-PRLR antibody either lacks a C-terminal lysine or comprises an amino acid other than lysine at a C-terminus of the heavy chain constant region.

6. The ADC of claim 1, wherein said monoclonal anti-PRLR antibody is a humanized antibody.

7. The ADC of claim 2, wherein the heavy chain constant region of the anti-PRLR antibody either lacks a C-terminal lysine or comprises an amino acid other than lysine at a C-terminus of the heavy chain constant region.

8. The ADC of claim 2, wherein said monoclonal anti-PRLR antibody comprises an IgG1 isotype.

9. The ADC of claim 3, wherein said heavy chain constant region of said monoclonal anti-PRLR antibody either lacks a C-terminal lysine or comprises an amino acid other than lysine at a C-terminus of the heavy chain constant region.

10. The ADC of claim 2, wherein said monoclonal anti-PRLR antibody is a humanized antibody.

11. An antibody-drug conjugate (ADC) comprising the structure of Formula (X)

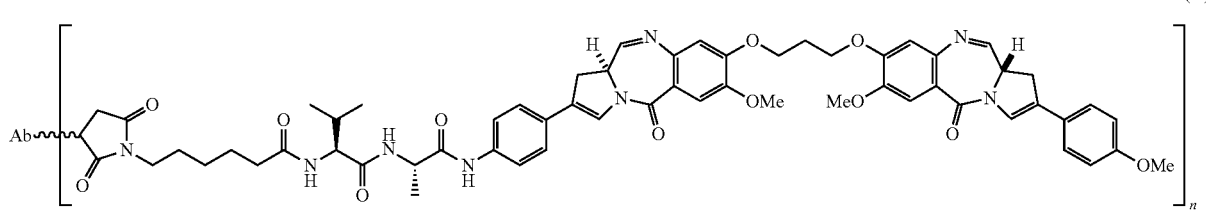

Formula (X)

wherein Formula (X) comprises a monoclonal anti-PRLR antibody (Ab) conjugated to "n" cytotoxic warheads,
wherein said monoclonal anti-PRLR antibody comprises:
i. a full heavy chain comprising SEQ ID NO: 1; and
ii. a full light chain comprising SEQ ID NO: 6, wherein said monoclonal anti-PRLR antibody is conjugated to said cytotoxic warheads through amino acid residue 242 of SEQ ID NO: 1, and
wherein "n" is 2.

* * * * *